United States Patent [19]

Michel et al.

[11] Patent Number: 5,908,629
[45] Date of Patent: *Jun. 1, 1999

[54] CONJUGATE VACCINE FOR GROUP B STREPTOCOCCUS

[75] Inventors: James L. Michel, Waban; Dennis L. Kasper, Newton Centre; Frederick M. Ausubel, Newton; Lawrence C. Madoff, Boston, all of Mass.

[73] Assignees: The General Hospital Corporation; Brigham and Women's Hospital, both of Boston, Mass.

[*] Notice: This patent is subject to a terminal disclaimer.

[21] Appl. No.: 08/467,147

[22] Filed: Jun. 6, 1995

Related U.S. Application Data

[62] Division of application No. 08/363,311, Dec. 22, 1994, Pat. No. 5,648,241, which is a continuation of application No. 07/968,866, Nov. 2, 1992, abandoned, which is a continuation-in-part of application No. 07/408,036, Sep. 15, 1989, abandoned.

[51] Int. Cl.$^6$ ............... A61K 39/385; A61K 39/09; C07K 14/315
[52] U.S. Cl. ............... 424/197.11; 424/244.1; 530/403
[58] Field of Search ............... 424/197.11, 237.1, 424/244.1; 435/69.3, 172.1; 530/350, 403, 825; 536/23.7

[56] References Cited

U.S. PATENT DOCUMENTS

| | | | |
|---|---|---|---|
| 4,207,414 | 6/1980 | Kasper | 536/53 |
| 4,284,537 | 8/1981 | Beachey | 524/17 |
| 4,324,887 | 4/1982 | Kasper | 536/53 |
| 4,356,170 | 10/1982 | Jennings et al. | 424/194.1 |
| 4,356,263 | 10/1982 | Kasper | 435/101 |
| 4,367,221 | 1/1983 | Kasper | 424/137.1 |
| 4,367,222 | 1/1983 | Kasper | 424/137.1 |
| 4,367,223 | 1/1983 | Kasper | 424/244.1 |
| 4,425,330 | 1/1984 | Norcross et al. | 424/203.1 |
| 4,619,828 | 10/1986 | Gordon | 424/194.1 |
| 4,673,574 | 6/1987 | Anderson | 424/194.1 |
| 4,757,134 | 7/1988 | Blake et al. | 530/350 |
| 4,761,283 | 8/1988 | Anderson | 424/194.1 |
| 4,789,735 | 12/1988 | Frank et al. | 424/197.11 |
| 4,830,852 | 5/1989 | Marburg et al. | 424/165.1 |
| 4,902,506 | 2/1990 | Anderson et al. | 424/194.1 |
| 5,302,386 | 4/1994 | Kasper et al. | 424/197.11 |
| 5,648,241 | 7/1997 | Michel et al. | 435/69.3 |

FOREIGN PATENT DOCUMENTS

| | | |
|---|---|---|
| 0 038 265 | 10/1981 | European Pat. Off. . |
| 0 175 261 | 3/1986 | European Pat. Off. . |
| 0 206 852 | 12/1986 | European Pat. Off. . |
| 0 245 045 | 11/1987 | European Pat. Off. . |
| WO 87/06267 | 10/1987 | WIPO . |
| WO 89/00583 | 1/1989 | WIPO . |
| WO 91/04049 | 4/1991 | WIPO . |
| WO 91/08772 | 6/1991 | WIPO . |
| WO 94/06467 | 3/1994 | WIPO . |

OTHER PUBLICATIONS

Baker, C. J. and Kasper, D. L., "Group B Streptococcal Vaccines," *Rev. Inf. Dis.* 7(4):458–467 (1985).

Paoletti et al. Immunogenicity of Group B Streptococcus type III polysaccharide–tetanus toxoid vaccine in baboons. Infection and Immunity vol. 64 677–679, 1996.

Madoff et al. Maternal immunization of mice with Group B Streptococcal type III polysaccharide–beta C protein conjugate elicits protective antibody to multiple serotypes. J. Clin. Invest. vol. 94 286–292, 1994.

Anderson, B. E. et al., "A Protective Protein Antigen of *Rickettsia rickettsii* Has Tandemly Repeated, Near–Identical Sequences", *Infect. Immun.* 58 (9):2760–2769 (Sep. 1990).

Avery, O. T. et al., "Chemo–Immunological Studies on Conjugated Carbohydrate–Proteins", *J. Exp. Med.* 54:437–447 (1931).

Baker, C. J. et al., "Immunization of Pregnant Women With A Polysaccharide Vaccine of Group B Streptococcus", *New Eng. J. Med.* 319(18):1180–1185 (Nov. 1988).

Baker, C. J., "Immunization to Prevent Group B Streptococcal Disease: Victories and Vexations," *J. Inf. Dis.* 161(5):917–921 (May 1990).

Bevanger, L. et al., "Complete and Incomplete Ibc Protein Fraction in Group B Streptococci", *Acta path. microbiol. scand. Sect. B* 87:51–54 (1979).

Bevanger, L. et al., "The Ibc Protein Fraction of Group B Streptococci: Characterization of Protein Antigens Extracted by HCl", *Acta path. microbiol. scand. Sect. B.* 89:205–209 (1981).

Bevanger, L., "Ibc Proteins as Serotype Markers of Group B Streptococci", *Acta path. microbiol. immunol. scand. Sect. B* 91:231–234 (1983).

Bevanger, L., "The Ibc Proteins of Group B Streptococci: Isolation of the α and β Antigens by Immunosorbent Chromatography and Test for Human Serum Antibodies Against the Two Antigens", *Acta path. microbiol. immunol. scand. Sect. B* 93:113–119 (1985).

Bevanger, L. et al., "Mouse–Protective Antibodies Against the Ibc Proteins of Group B Streptococci", *Acta path. microbiol. immunol. scand. Sect. B* 93:121–124 (1985).

(List continued on next page.)

*Primary Examiner*—James Ketter
*Assistant Examiner*—John S. Brusca
*Attorney, Agent, or Firm*—Sterne, Kessler, Goldstein & Fox P.L.L.C.

[57] ABSTRACT

A vaccine capable of protecting a recipient from infection caused by group B Streptococcus. The vaccine provides polysaccharide-protein moieties and contain (a) a group B Streptococcus polysaccharide conjugated to (b) a functional derivative of a group B Streptococcus C protein alpha antigen that retains the ability to elicit protective antibodies against group B Streptococcus. The vaccine may contain only one type of such polysaccharide-protein unit or may contain a mixture of more than one type of unit.

21 Claims, 11 Drawing Sheets

OTHER PUBLICATIONS

Bevanger, L. et al., "Characterization of the α antigen of the c proteins of group B streptococci (GBS) using a murine monoclonal antibody", Acta Pathol. Microbiol. Immunol. Scand. 100(1):57–62 (Jan. 1992).

Bittle, J. L. et al., "Vaccines Produced by Conventional Means to Control Major Infectious Diseases of Man and Animals", Adv. Vet. Sci. Comp. Med. 33:1–63 (Feb. 1989).

Brady, L. J. et al., "Identification of Non–Immunoglobulin A–Fc–Binding Forms and Low–Molecular–Weight Secreted Forms of the Group B Streptococcal β Antigen", Infect. Immun. 57(5):1573–1581 (May 1989).

Baker Immunization to prevent Group B Streptococcal disease: Victories and Vexations. J. Infectious Diseases vol. 161 917–921, 1990.

Madoff et al. Protection of neonatal mice from group B streptococcal infection by maternal immunization with Beta C protein. Infection and Immunity vol. 60 pp. 4989–4994, 1992.

Cleat, P. H. et al., "Cloning and Expression in Escherichia coli of the Ibc Protein Genes of Group B Streptococci: Binding of Human Immunoglobulin A to the Beta Antigen", Infect. Immun. 55(5):1151–1155 (1987).

Coleman, R. T. et al., "Prevention of Neonatal Group B Streptococcal Infections: Advances in Maternal Vaccine Development", Obst. Gynec. 80(2):301–309 (Aug. 1992).

Dailey, D. C. et al., "The Phenotypically Variable Surface Protein of Trichomonas vaginalis Has a Single, Tandemly Repeated Immunodominant Epitope", Infect. Immun. 59(6):2083–2088 (Jun. 1991).

Enea, V. et al., "DNA Cloning of Plasmodium falciparum Circumsporozoite Gene: Amino Acid Sequence of Repetitive Epitope", Science 225:628–630 (1984).

Feldman, R. G. et al., "The immune response to the group B streptococcus", Rev. Med. Microbiol. 3(1):52–58 (Jan. 1992).

Ferrieri, P., "Surface–Localized Protein Antigens of Group B Streptococci", Rev. Infect. Dis. 10(Suppl. 2):s363–s366 (Jul.–Aug. 1988).

Fischetti, V. A. et al., "Structure, Function, and Genetics of Streptococcal M Protein", Rev. Infect. Dis. 10(Suppl. 2):s356–s359 (Jul.–Aug. 1988).

Fischetti, V. A. et al., "Common Characteristics of the Surface Proteins from Gram–Positive Cocci", in: Genetics and Molecular Biology of Streptococci, Lactococci, and Enterococci, Dunny, G. M. et al., eds., American Society for Microbiology: Washington, D.C., pp. 290–294 (Jul. 1991).

Hedén, L.–O. et al., "Molecular characterization of an IgA receptor from group B streptococci: sequence of the gene, identification of a proline–rich region with unique structure and isolation of N–terminal fragments with IgA–binding capacity", Eur. J. Immunol. 21:1481–1490 (Jun. 1991).

Horensky, D. S. et al., "Generation and Analysis of Group B Streptococcal Alpha C Protein Gene Constructs Containing Variable Numbers of Tandem Repeats", Abstracts of the 93rd General Meeting of the American Society for Microbiology, Session 107, p. 107, Abstract D–68 (May 1993).

Insel, R. A., "Material Immunization to Prevent Neonatal Infections", New Eng. J. Med. 319(18):1219–1220 (Nov. 1988).

Jerlström, P. G. et al., "The IgA–binding β antigen of the c protein complex of Group B streptococci: sequence determination of its gene and detection of two binding regions", Mol. Microbiol. 5(4): 843–849 (Apr. 1991).

Kling, D. E. et al., "Group B Streptococus C Protein Alpha Antigen Peptide Heterogeneity", Abstracts of the 93rd General Meeting of the American Society for Microbiology, Session 166, p. 59, Abstract No. B–189 (May 1993).

Kuypers, J. M. et al., "Molecular Analysis of a Region of the Group B Streptococcus Chromosome Involved in Type III Capsule Expression", Infect. Immun. 57(10):3058–3065 (Oct. 1989).

Lagergard, T. et al., "Synthesis and Immunological Properties of Conjugates Composed of Group B Streptococcus Type III Capsular Polysaccharide Covalently Bound to Tetanus Toxoid", Infect. Immun. 58(3):687–694 (Mar. 1990).

Madoff, L. C. et al., "Phenotypic Diversity in the Alpha C Protein of Group B Streptococci", Infect. Immun. 59(8):2638–2644 (Aug. 1991).

Madoff, L. C. et al., "Protection of Neonatal Mice from Group B Streptococcal infection by Maternal Immunization with Beta C Protein", Clin. Res. 40(2):213A (Mar. 1992).

Lerner, R. A. et al., "The Development of Synthetic Vaccines", in: The Biology of Immunologic Disease, Dixon, F. J. et al., eds., Sinauer Associates: Sunderland, MA, pp. 331–338 (1983).

Madoff, L. C. et al., "Partial characterization of C protein antigens of group B Streptococcus", The Lancefield Society 1989 Meeting, Houston, Texas (Sep. 1989).

Madoff, L. C. et al., "A Monoclonal Antibody Identifies a Protective C–Protein Alpha–Antigen Epitope in Group B Streptococci", Infect. Immun., 59(1):204–210 (Jan. 1991).

Madoff, L. C. et al., "The Cloned and Native Beta Antigens of the Group B Streptococcal C Protein: Role in Protective Immunity", in: New Perspectives on Streptococci and Streptococcal Infections, Orefiel, G., ed., Gustav Fischer: New York, pp. 363–365 (Mar. 1992).

Michel, J. L. et al., "Group B Streptococcal Infections: An Update", Infect. Dis. Pract. 13(6):1–12 (Mar. 1990).

Michel, J. L. et al., "C Proteins of Group B Streptococci", in: Genetics and Molecular Biology of Streptococci, Lactococci, and Enterococci, Dunny, G. M. et al., eds., American Society for Microbiology: Washington, D.C., pp. 214–218 (Jul. 1991).

Michel, J. L. et al ., "Cloned Alpha and Beta C–Protein Antigens of Group B Streptococci Elicit Protective Immunity", Infect. Immun. 59(6):2023–2028 (Jun. 1991).

Michel, J. L. et al., "Nucleotide Sequence Analysis of the C Protein Alpha Antigen of Group B Streptococcus", Abstracts of 1992 American Society for Microbiology General Meeting, New Orleans, LA, p. 69, Abstract B–261 (Mar. 1992).

Michel, J. L. et al., "Characterization of the Native and Cloned C Protein Alpha Antigens of Group B Streptococcus", in: New Perspectives on Streptococci and Streptococcal Infections, Orefiel, G., ed., Gustav Fischer: New York, pp. 366–367 (Mar. 1992).

Michel, J. L. et al., "Large, identical, tandem repeating units in the C protein alpha antigen gene, bca, of group B streptococci", Proc. Natl. Acad. Sci. USA 89:10060–10064 (Nov. 1992).

Michel, J. L. et al., "Genotypic Diversity and Evidence for Two Distinct Classes of the C Protein Alpha Antigen of Group B Streptococcus", Twelfth Lancefield International Symposium on Streptococci and Streptococcal Diseases, St. Petersburg, Russia (Sep. 1993).

Michel, J. L. et al., "Two Distinct Classes of the C Protein Alpha Antigen of Group B Streptococcus Display Phenotypic and Genotypic Diveristy", Abstracts of the 1993 IDSA Annual Meeting, *Clin. Infect. Dis.* 17(3):Abstract No. 1 (Sep. 1993).

Paoletti, L. C. et al., "An Oligosaccharide–Tetanus Toxoid Conjugate Vaccine against Type III Group B Streptococcus", *J. Biol. Chem.* 265(30):18278–18283 (Oct. 1990).

Paoletti, L. C. et al., "Effects of Chain Length on the Immunogenicity in Rabbits of Group B Streptococcus Type III Oligosaccharide–Tetanus Toxoid Conjugates", *J. Clin. Invest.* 89:203–209 (Jan. 1992).

Paoletti, L. C. et al., "Group B Streptococcus Type III Glycoconjugate Vaccines", *Trends in Glycosci. Glycotech.* 4(17):269–278 (May 1992).

Paoletti, L. C. et al., "Group B Streptococcus Type II Polysaccharide–Tetanus Toxoid Conjugate Vaccine", *Infect. Immun.* 60(10):4009–4014 (Oct. 1992).

Rodewald, A. K. et al., "Neonatal Mouse Model of Group B Streptococcal Infection", *J. Infect. Dis.* 166(3):635–639 (Sep. 1992).

Ross, P. W. et al., "Group–B Streptococcus: Profile of an Organism", *J. Med. Microbiol.* 18:139–166 (1984).

Russell–Jones, G. J. et al., "Identification of Protein Antigens of Group B Streptococci, with Special Reference to the Ibc Antigens", *J. Exp. Med.* 160:1476–1484 (1984).

Valtonen, M. V. et al., "Isolation of a C (Ibc) protein from group B Streptococcus which elicits mouse protective antibody", *Microb. Path.* 1:191–204 (1986).

von Eichel–Streiber, C. et al., "*Clostridium difficile* toxin A carries a C–terminal repetitive structure homologous to the carbohydrate binding region of streptococcal glycosyltransferases", *Gene* 96:107–113 (Nov. 1990).

Ward, J. et al., "*Haemophilus influenzae* Vaccines", in: *Vaccines*, Plotkin, S. A. et al., eds., Saunders: Philadelphia, pp. 300–332 (Jun. 1988).

Wessels, M. R. et al., "Immunogenicity in Animals of a Polysaccharide–Protein Conjugate Vaccine against Type III Group B Streptococcus", *J. Clin. Invest.* 86:1428–1433 (Nov. 1990).

Wilkinson, H. W. et al., "Type–Specific Antigens of Group B Type Ic Streptococci", *Infect. Immun.* 4(5):596–604 (1971).

Young, J. F. et al., "Expression of *Plasmodium falciparum* Circumsporozoite Proteins in *Escherichia coli* for Potential Use in a Human Malaria Vaccine", *Science* 288:958–962 (1985).

Attachment A (Work Statement) from Request for Proposal No. NIH–NIAID–DMID–92–13, issued by the Department of Health and Human Services for the National Institutes of Health, on Jan. 21, 1992, entitled, "Prevention of Group B Streptococcal Infections in Neonatal and Infant Populations".

Abstract of Grant No. 2R37AI23339–08, "Immunochemistry of group B streptococcal polysaccharides (human, mice, rabbits)", Kasper, D. L., Principal Investigator, Dialog File 265/266, Fed. Research in Progress, printout of Jan. 26, 1993 for fiscal year 1992.

Abstract of Grant No. 5K11AI00981–03, "C proteins in immunity to group B streptococcus," Madoff, L. C., Principal Investigator, Dialog File 265/266, Fed. Research in Progress, printout of Jan. 26, 1993 for fiscal year 1992.

Abstract of Grant No. 5R01AI30628–02, "Prevention of perinatal group B streptococcal infections (human, mice, rabbits)", Kasper, D. L., Principal Investigator, Dialog File 265/266, Fed. Research in Progress, printout of Jan. 26, 1993 for fiscal year 1992.

Abstract of Grant No. 5R29AI8500–03, "Genetic analysis of C proteins in group B streptococcus (mice)," Michel, J. L., Principal Investigator, Dialog file 265/266, Fed. Research in Progress, printout of Jan. 26, 1993 for fiscal year 1992.

English Abstract of European Patent Document EP 0 206 852 (Ref. AM1), from Derwent World Patents Index, Dialog File 351.

Boyer, K.M. et al., "Human IgG Antibody to Group B Streptococcus Type II: Protection in a Mouse Model," *Clin. Res.* 34(4):962A (1986).

Devi, S.J.N. et al., "Antibodies to poly[(2→8)–α–N–acetylneuraminic acid] and poly[(2→9)–α–N–acetylneuraminic acid] are elicited by immunization of mice with *Escherichia coli* K92 conjugates: Potential vaccines for groups B and C meningococci and *E. coli* K1," *Proc. Natl. Acad. Sci. USA* 88:7175–7179 (Aug. 1991).

Dick, W.E. Jr. and Beurret, M., "Glycoconjugates of Bacterial Carbohydrate Antigens: A Survey and Consideration of Design and Preparation Factors," in *Contributions to Microbiology and Immunology*, vol. 10, Cruse, J.M. and Lewis R.E. Jr., eds., Karger, Basel, Switzerland (Jul. 1989), pp. 48–114.

Dintzis, R.Z., "Rational Design of Conjugate Vaccines," *Pediatr. Res.* 32(4):376–385 (Oct. 1992).

Heiman, H.S. and Weisman, L.E., "The Opsonic Antibody Response of Female Rats to Type III Group B Streptococcal Immunization: a Model for Maternal Immunity," *Veterin. Immunol. Immunopath.* 24:79–89 (Jan. 1990).

Jennings, H.J. et al., "Conformational Aspects Critical to the Immunospecificity of the Type III Group B Streptococcal Polysaccharide," *Biochemistry* 20(16):4511–4518 (1981).

Jennings, H.J. and Lugowski, C., "Immunochemistry of Groups A, B, and C Meningococcal Polysaccharide–Tetanus Toxoid Conjugates," *J. Immunol.* 127(3):1011–1018 (1981).

Jennings, H.J. et al., "Structural Determination of the Capsular Polysaccharide Antigen of Type II Group B Streptococcus," *J. Biol. Chem.* 258(3):1793–1798 (1983).

Jennings, H.J., "Capsular Polysaccharides as Human Vaccines," in *Advances in Carbohydrate Chemistry and Biochemistry*, vol. 41, Tipson, R.S. and Horton, D., eds., Academic Press, NY (1983), pp. 155–208.

Jennings, H.J. and Roy, R., "Enhancement of the Immune Response to the Group B Polysaccharide of *Neisseria meningitidis* by Means of Its Chemical Modification," in *The Pathogenic Neisseriae: Proc. 4th Intl. Symp.*, Schoolnik, G.K. et al., eds., Am. Soc. Microbiol., Washington, D.C. (1985), pp. 628–632.

Kasper, D.L. et al., "Immunochemical Analysis and Immunogenicity of the Type II Group B Streptococcal Capsular Polysaccharide," *J. Clin. Invest.* 72:260–269 (1983).

Pappenheimer, A.M. Jr. et al., "An Immunological Study of the Diphtheria Toxin Molecule," *Immunochemistry* 9:891–906 (1972).

Roy, R. and Pon, R.A., "Efficient Synthesis of α(2–8)–Linked N–Acetyl and N–Glycolylneuraminic Acid Disaccharides from Colominic Acid," *Glycoconjugate J.* 7(1):3–12 (Mar. 1990).

Timoney, J.F. et al., "The Genus Streptococcus," *Hagan and Bruner's Microbiology and Infectious Diseases of Domestic Animals, 8th Edition*, Comstock Publishing Associates, New York (1988), pp. 181–186.

Wessels, M.R. et al., "Structure and Immunochemistry of an Oligosaccharide Repeating Unit of the Capsular Polysaccharide of Type III Group B Streptococcus," *J. Biol. Chem.* 262(17):8262–8267 (1987).

Wessels, M.R. et al., "Isolation and Characterization of Type IV Group B Streptococcus Capsular Polysaccharide," *Infec. Immun.* 57(4):1089–1094 (Apr. 1989).

Wessels, M.R. et al., "Structural Determination and Immunochemical Characterization of the Type V Group B Streptococcus Capsular Polysaccharide," *J. Biol. Chem.* 266(11):6714–6719 (Apr. 1991).

Wessels, M.R. et al., "Immunogenicity and Protective Activity in Animals of a Type V Group B Streptococcal Polysaccharide–Tetanus Toxoid Conjugate Vaccine," *J. Infect. Dis.* 171(4):879–884 (Apr. 1995).

```
ACG    AATTCG                              CGAATTAATTCG
TGCTTAA    GC         FILL &               GCTTAATTAAGC
                      LIGATE
 EcoRI CUT           ─────────→           XmnI SITE CREATED
                                          EcoRI SITE DESTROYED
```

FIG. 3A

```
AATTCGAGCT   CGCCCGGGG                    AATTCGCGCCCGGGG
TTAAGC       TCGAGCGGGGCCCC               TTAAGCGCGGGGCCCC

SacI CUT         CUT BACK                FnuD2 SITE CREATED
                  & LIGATE                 SacI SITE DESTROYED
```

FIG. 3B

```
AATTCGAGCT   CGCCCGGGG              AATTC   GGGG            AATTCGGGG       10 BASE PAIRS DELETED
TTAAGC       TCGAGCGGGGCCCC         TTAAG   CCCC            TTAAGCCCC       SacI, XmaI, & SmaI
                                                                            SITES REMOVED
 SacI CUT         CUT BACK                       LIGATE
```

FIG. 3C

```
                                        -10
AGCATAGATA TTCTAATATT TGTTGTTTAA GCCTATAATT TACTCTGTAT AGAGTTATAC         60
     RBF          SIGNAL PEPTIDE
AGAGTAAAGG AGAATATT ATG TTT AGA AGG TCT AAA AAT AAC AGT TAT GAT          111
                   Met Phe Arg Arg Ser Lys Asn Asn Ser Tyr Asp
                    1               5                  10

ACT TCA CAG ACG AAA CAA CGG TTT TCA ATT AAG AAG TTC AAG TTT GGT          159
Thr Ser Gln Thr Lys Gln Arg Phe Ser Ile Lys Lys Phe Lys Phe Gly
         15              20                  25
                                                        MATURE
GCA GCT TCT GTA CTA ATT GGT CTT AGT TTT TTG GGT GGG GTT ACA CAA          207
Ala Ala Ser Val Leu Ile Gly Leu Ser Phe Leu Gly Gly Val Thr Gln
         30              35                  40
PROTEIN
GGT AAT CTT AAT ATT TTT GAA GAG TCA ATA GTT GCT GCA TCT ACA ATT          255
Gly Asn Leu Asn Ile Phe Glu Glu Ser Ile Val Ala Ala Ser Thr Ile
         45              50                  55

CCA GGG AGT GCA GCG ACC TTA AAT ACA AGC ATC ACT AAA AAT ATA CAA          303
Pro Gly Ser Ala Ala Thr Leu Asn Thr Ser Ile Thr Lys Asn Ile Gln 60              65              70              75

AAC GGA AAT GCT TAC ATA GAT TTA TAT GAT GTA AAA TTA GGT AAA ATA          351
Asn Gly Asn Ala Tyr Ile Asp Leu Tyr Asp Val Lys Leu Gly Lys Ile
                 80              85              90

GAT CCA TTA CAA TTA ATT GTT TTA GAA CAA GGT TTT ACA GCA AAG TAT         399
Asp Pro Leu Gln Leu Ile Val Leu Glu Gln Gly Phe Thr Ala Lys Tyr
             95              100             105

GTT TTT AGA CAA GGT ACT AAA TAC TAT GGG GAT GTT TCT CAG TTG CAG         447
Val Phe Arg Gln Gly Thr Lys Tyr Tyr Gly Asp Val Ser Gln Leu Gln
         110             115             120

AGT ACA GGA AGG GCT AGT CTT ACC TAT AAT ATA TTT GGT GAA GAT GGA         495
Ser Thr Gly Arg Ala Ser Leu Thr Tyr Asn Ile Phe Gly Glu Asp Gly
         125             130             135

CTA CCA CAT GTA AAG ACT GAT GGA CAA ATT GAT ATA GTT AGT GTT GCT         543
Leu Pro His Val Lys Thr Asp Gly Gln Ile Asp Ile Val Ser Val Ala
    140             145             150             155
```

FIG.6A

```
TTA ACT ATT TAT GAT TCA ACA ACC TTG AGG GAT AAG ATT GAA GAA GTT      591
Leu Thr Ile Tyr Asp Ser Thr Thr Leu Arg Asp Lys Ile Glu Glu Val
            160                 165                 170

AGA ACG AAT GCA AAC GAT CCT AAG TGG ACG GAA GAA AGT CGT ACT GAG      639
Arg Thr Asn Ala Asn Asp Pro Lys Trp Thr Glu Glu Ser Arg Thr Glu
            175                 180                 185

GTT TTA ACA GGA TTA GAT ACA ATT AAG ACA GAT ATT GAT AAT AAT CCT      687
Val Leu Thr Gly Leu Asp Thr Ile Lys Thr Asp Ile Asp Asn Asn Pro
            190                 195                 200

AAG ACG CAA ACA GAT ATT GAT AGT AAA ATT GTT GAG GTT AAT GAA TTA      735
Lys Thr Gln Thr Asp Ile Asp Ser Lys Ile Val Glu Val Asn Glu Leu
            205                 210                 215
                              REPEAT 1
GAG AAA TTG TTA GTA TTG TCA GTA CCG GAT AAA GAT AAA TAT GAT CCA      783
Glu Lys Leu Leu Val Leu Ser Val Pro Asp Lys Asp Lys Tyr Asp Pro
    220             225             230                 235

ACA GGA GGG GAA ACA ACA GTA CCC CAA GGG ACA CCA GTT TCA GAT AAA      831
Thr Gly Gly Glu Thr Thr Val Pro Gln Gly Thr Pro Val Ser Asp Lys
            240                 245                 250

GAA ATC ACA GAC TTA GTT AAG ATT CCA GAT GGC TCA AAA GGG GTT CCG      879
Glu Ile Thr Asp Leu Val Lys Ile Pro Asp Gly Ser Lys Gly Val Pro
            255                 260                 265

ACA GTT GTT GGT GAT CGT CCA GAT ACT AAC GTT CCT GGA GAT CAT AAA      927
Thr Val Val Gly Asp Arg Pro Asp Thr Asn Val Pro Gly Asp His Lys
            270                 275                 280

GTA ACG GTA GAA GTA ACG TAT CCA GAT GGA ACA AAG GAT ACA GTA GAA      975
Val Thr Val Glu Val Thr Tyr Pro Asp Gly Thr Lys Asp Thr Val Glu
            285                 290                 295
                                              (REPEAT 2-9)  PARTIAL REPEAT
GTA ACG GTT CAT GTG ACA CCA AAA CCA ((1003-2970)) GTA CCG GAT AAA GAT  2985
Val Thr Val His Val Thr Pro Lys Pro  ((309-964))  Val Pro Asp Lys Asp
            300                 305                           965
```

FIG.6B

```
                              C-TERMINUS
AAA TAT GAT CCA ACA GGT AAA GCT CAG CAA GTC AAC GGT AAA GGA AAT         3033
Lys Tyr Asp Pro Thr Gly Lys Ala Gln Gln Val Asn Gly Lys Gly Asn
970             975             980             985

AAA CTA CCA GCA ACA GGT GAG AAT GCA ACT CCA TTC TTT AAT GTT GCA         3081
Lys Leu Pro Ala Thr Gly Glu Asn Ala Thr Pro Phe Phe Asn Val Ala
                990             995             1000

GCT TTG ACA ATT ATA TCA TCA GTT GGT TTA TTA TCT GTT TCT AAG AAA         3129
Ala Leu Thr Ile Ile Ser Ser Val Gly Leu Leu Ser Val Ser Lys Lys
            1005            1010            1015

AAA GAG GAT TAATCTTTTG ACCTAAAATG TCACTAAATT TTTCACCATT TATTGGT         3185
Lys Glu Asp END
        1020

GTGAACACAT TAATAAAGTT ATGCATCTCT CTCCAACAAA ATTAATTAAA GTGTTTCAAT        3245
TTTTCGAGAT TAATTCTTGA AAAAAGCCTA TCGAGATTAT TAATTTCGAT AGGCTTTTGA        3305
TTTTGTGTAA GCGTCCAATA TACCTTGTTA TTGGACGCTT ACT                         3348
```

FIG.6C

1   MFRRSKNNSYDTSQTKQRFSIKKFK FGAASVLIGL SFLGGV TQGNLNIFEESIVAA

2   MFKSNYERKMRYSIRK FSVGVASVAVRSLFMG SVAHA

3   MARQQTKKNYSLRKLK TGTASVAVALTVLGAGFA NQTEVRA

4   MTKNNTNRHYSLRKLK TGTASVAVALTVLGAGLVV NTNEVSA

5   MAKNNTNRHYSLRKLK TGTASVAVALTVLGAGFA NQTEVKA

6   MAKNNTNRHYSLRKLK TGTASVAVALTVLGAGFA NQTEVKANGDGNPREV

FIG.7A

1   KAQQVNGKGNK | LPATGE | NAT | PFFNVAAL | TIISSVGLLSV SKKKE D

2   NKAPMKETKRQ | LPYTGV | TAN | PFFTAAAL | TVMATAGVAAVV KRKEE N

3   RPSQNKGNRSQ | LPSTGE | AAN | PFFTAAAA | TVMVSAGMLAL KRKEE N

4   AKKEDAKKAET | LPTTGE | GSN | PFFTAAAL | AVMAGAGALAVA SKRKE D

5   AKKDDAKKAET | LPTTGE | GSN | PFFTAAAL | AVMAGAGALAVA SKRKE D

6   SRSAMTQQKRT | LPSTGE | TAN | PFFTAAAA | TVMVSAGMLAL KRKEE N

7   NKAPNKETKRQ | LPSTGE | TAN | PFFTAAAL | TVM AAA

8   KGNPTSTTEKK | LPYTGV | ASN LVLEIMGLIGLIGTSFIAM KRRKS

FIG7B

```
                         SEQUENCE LISTING (1) GENERAL INFORMATION:

(iii) NUMBER OF SEQUENCES:  65

(2) INFORMATION FOR SEQ ID NO:1:

(i) SEQUENCE CHARACTERISTICS:
          (A) LENGTH: 8 amino acids
          (B) TYPE: amino acid
          (D) TOPOLOGY: both (ii) MOLECULE TYPE: peptide (xi) SEQUENCE DESCRIPTION: SEQ ID NO:1:

Pro Pro Phe Phe Xaa Xaa Ala Ala
     1               5

(2) INFORMATION FOR SEQ ID NO:2:

(i) SEQUENCE CHARACTERISTICS:
          (A) LENGTH: 6 amino acids
          (B) TYPE: amino acid
          (D) TOPOLOGY: both (ii) MOLECULE TYPE: peptide (xi) SEQUENCE DESCRIPTION: SEQ ID NO:2:

Leu Pro Xaa Thr Gly Glu
     1               5

(2) INFORMATION FOR SEQ ID NO:3:

(i) SEQUENCE CHARACTERISTICS:
          (A) LENGTH: 15 base pairs
          (B) TYPE: nucleic acid
          (C) STRANDEDNESS: single
          (D) TOPOLOGY: both (xi) SEQUENCE DESCRIPTION: SEQ ID NO:3:

GATCCATTGT GCTGG                                                  15

(2) INFORMATION FOR SEQ ID NO:4:
```

(i) SEQUENCE CHARACTERISTICS:
    (A) LENGTH: 11 base pairs
    (B) TYPE: nucleic acid
    (C) STRANDEDNESS: single
    (D) TOPOLOGY: both (xi) SEQUENCE DESCRIPTION: SEQ ID NO:4:

GTAACACGAC C                                                                                       11

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: both (xi) SEQUENCE DESCRIPTION: SEQ ID NO:5:

ACACGAGATT TC                                                                                  12

(2) INFORMATION FOR SEQ ID NO:6:

(i) SEQUENCE CHARACTERISTICS:
        (A) LENGTH: 57 base pairs
        (B) TYPE: nucleic acid
        (C) STRANDEDNESS: single
        (D) TOPOLOGY: both (xi) SEQUENCE DESCRIPTION: SEQ ID NO:6:

ATGACCATGA TTACGAATTC GAGCTCGCCC GGGGATCCAT TGTGCTGGAA AGCCACC        57

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: double
        (D) TOPOLOGY: both (xi) SEQUENCE DESCRIPTION: SEQ ID NO:7:

GGATCCATTG TGCTGG                                                                             16

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: double
        (D) TOPOLOGY: both (xi) SEQUENCE DESCRIPTION: SEQ ID NO:8:

GGATCCATTG TGCTGGCCAG CACAATGGAT CC                                32

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: both (xi) SEQUENCE DESCRIPTION: SEQ ID NO:9:

GGATCCATTG TG                                                                                 12

(2) INFORMATION FOR SEQ ID NO:10:

(i) SEQUENCE CHARACTERISTICS:
        (A) LENGTH: 20 base pairs

```
            (B) TYPE: nucleic acid
            (C) STRANDEDNESS: double
            (D) TOPOLOGY: both (xi) SEQUENCE DESCRIPTION: SEQ ID NO:10:

GGATCCATTG TGCTCTAAAG                                                    20

(2) INFORMATION FOR SEQ ID NO:11:

(i) SEQUENCE CHARACTERISTICS:
            (A) LENGTH: 12 base pairs
            (B) TYPE: nucleic acid
            (C) STRANDEDNESS: double
            (D) TOPOLOGY: both (xi) SEQUENCE DESCRIPTION: SEQ ID NO:11:

CGAATTAATT CG                                                            12

(2) INFORMATION FOR SEQ ID NO:12:

(i) SEQUENCE CHARACTERISTICS:
            (A) LENGTH: 13 base pairs
            (B) TYPE: nucleic acid
            (C) STRANDEDNESS: single
            (D) TOPOLOGY: both (xi) SEQUENCE DESCRIPTION: SEQ ID NO:12:

TCGAGCGGGC CCC                                                           13

(2) INFORMATION FOR SEQ ID NO:13:

(i) SEQUENCE CHARACTERISTICS:
            (A) LENGTH: 15 base pairs
            (B) TYPE: nucleic acid
            (C) STRANDEDNESS: double
            (D) TOPOLOGY: both (xi) SEQUENCE DESCRIPTION: SEQ ID NO:13:

AATTCGCGCC CGGGG                                                         15

(2) INFORMATION FOR SEQ ID NO:14:

(i) SEQUENCE CHARACTERISTICS:
            (A) LENGTH: 1380 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 79..1173

(ix) FEATURE:
            (A) NAME/KEY: misc_feature
            (B) LOCATION: 1004
            (D) OTHER INFORMATION: /note= "This feature is to signify
                that the nucleotide sequence from position 757
                through 1003 is inserted at position 1004 and can be
                repeated up to eight times (for a total of nine
                repeating copies of these sequences within the
                polynucleotide)."

(xi) SEQUENCE DESCRIPTION: SEQ ID NO:14:

AGCATAGATA TTCTAATATT TGTTGTTTAA GCCTATAATT TACTCTGTAT AGAGTTATAC         60

AGAGTAAAGG AGAATATT ATG TTT AGA AGG TCT AAA AAT AAC AGT TAT GAT         111
                    Met Phe Arg Arg Ser Lys Asn Asn Ser Tyr Asp
                      1               5                  10

ACT TCA CAG ACG AAA CAA CGG TTT TCA ATT AAG AAG TTC AAG TTT GGT         159
Thr Ser Gln Thr Lys Gln Arg Phe Ser Ile Lys Lys Phe Lys Phe Gly
```

-continued

|  |  |  | 15 |  |  |  |  | 20 |  |  |  |  | 25 |  |  |  |
|---|---|---|---|---|---|---|---|---|---|---|---|---|---|---|---|---|
| GCA | GCT | TCT | GTA | CTA | ATT | GGT | CTT | AGT | TTT | TTG | GGT | GGG | GTT | ACA | CAA | 207 |
| Ala | Ala | Ser | Val | Leu | Ile | Gly | Leu | Ser | Phe | Leu | Gly | Gly | Val | Thr | Gln |  |
|  |  | 30 |  |  |  |  | 35 |  |  |  |  | 40 |  |  |  |  |

| GGT | AAT | CTT | AAT | ATT | TTT | GAA | GAG | TCA | ATA | GTT | GCT | GCA | TCT | ACA | ATT | 255 |
| Gly | Asn | Leu | Asn | Ile | Phe | Glu | Glu | Ser | Ile | Val | Ala | Ala | Ser | Thr | Ile |  |
|  | 45 |  |  |  |  | 50 |  |  |  |  | 55 |  |  |  |  |  |

| CCA | GGG | AGT | GCA | GCG | ACC | TTA | AAT | ACA | AGC | ATC | ACT | AAA | AAT | ATA | CAA | 303 |
| Pro | Gly | Ser | Ala | Ala | Thr | Leu | Asn | Thr | Ser | Ile | Thr | Lys | Asn | Ile | Gln |  |
| 60 |  |  |  | 65 |  |  |  |  | 70 |  |  |  |  | 75 |  |  |

| AAC | GGA | AAT | GCT | TAC | ATA | GAT | TTA | TAT | GAT | GTA | AAA | TTA | GGT | AAA | ATA | 351 |
| Asn | Gly | Asn | Ala | Tyr | Ile | Asp | Leu | Tyr | Asp | Val | Lys | Leu | Gly | Lys | Ile |  |
|  |  |  | 80 |  |  |  |  | 85 |  |  |  |  | 90 |  |  |  |

| GAT | CCA | TTA | CAA | TTA | ATT | GTT | TTA | GAA | CAA | GGT | TTT | ACA | GCA | AAG | TAT | 399 |
| Asp | Pro | Leu | Gln | Leu | Ile | Val | Leu | Glu | Gln | Gly | Phe | Thr | Ala | Lys | Tyr |  |
|  |  | 95 |  |  |  |  | 100 |  |  |  |  | 105 |  |  |  |  |

| GTT | TTT | AGA | CAA | GGT | ACT | AAA | TAC | TAT | GGG | GAT | GTT | TCT | CAG | TTG | CAG | 447 |
| Val | Phe | Arg | Gln | Gly | Thr | Lys | Tyr | Tyr | Gly | Asp | Val | Ser | Gln | Leu | Gln |  |
|  | 110 |  |  |  |  | 115 |  |  |  |  | 120 |  |  |  |  |  |

| AGT | ACA | GGA | AGG | GCT | AGT | CTT | ACC | TAT | AAT | ATA | TTT | GGT | GAA | GAT | GGA | 495 |
| Ser | Thr | Gly | Arg | Ala | Ser | Leu | Thr | Tyr | Asn | Ile | Phe | Gly | Glu | Asp | Gly |  |
| 125 |  |  |  |  | 130 |  |  |  |  | 135 |  |  |  |  |  |  |

| CTA | CCA | CAT | GTA | AAG | ACT | GAT | GGA | CAA | ATT | GAT | ATA | GTT | AGT | GTT | GCT | 543 |
| Leu | Pro | His | Val | Lys | Thr | Asp | Gly | Gln | Ile | Asp | Ile | Val | Ser | Val | Ala |  |
| 140 |  |  |  | 145 |  |  |  |  | 150 |  |  |  |  | 155 |  |  |

| TTA | ACT | ATT | TAT | GAT | TCA | ACA | ACC | TTG | AGG | GAT | AAG | ATT | GAA | GAA | GTT | 591 |
| Leu | Thr | Ile | Tyr | Asp | Ser | Thr | Thr | Leu | Arg | Asp | Lys | Ile | Glu | Glu | Val |  |
|  |  |  | 160 |  |  |  |  | 165 |  |  |  |  | 170 |  |  |  |

| AGA | ACG | AAT | GCA | AAC | GAT | CCT | AAG | TGG | ACG | GAA | GAA | AGT | CGT | ACT | GAG | 639 |
| Arg | Thr | Asn | Ala | Asn | Asp | Pro | Lys | Trp | Thr | Glu | Glu | Ser | Arg | Thr | Glu |  |
|  |  | 175 |  |  |  |  | 180 |  |  |  |  | 185 |  |  |  |  |

| GTT | TTA | ACA | GGA | TTA | GAT | ACA | ATT | AAG | ACA | GAT | ATT | GAT | AAT | AAT | CCT | 687 |
| Val | Leu | Thr | Gly | Leu | Asp | Thr | Ile | Lys | Thr | Asp | Ile | Asp | Asn | Asn | Pro |  |
|  | 190 |  |  |  |  | 195 |  |  |  |  | 200 |  |  |  |  |  |

| AAG | ACG | CAA | ACA | GAT | ATT | GAT | AGT | AAA | ATT | GTT | GAG | GTT | AAT | GAA | TTA | 735 |
| Lys | Thr | Gln | Thr | Asp | Ile | Asp | Ser | Lys | Ile | Val | Glu | Val | Asn | Glu | Leu |  |
| 205 |  |  |  |  | 210 |  |  |  |  | 215 |  |  |  |  |  |  |

| GAG | AAA | TTG | TTA | GTA | TTG | TCA | GTA | CCG | GAT | AAA | GAT | AAA | TAT | GAT | CCA | 783 |
| Glu | Lys | Leu | Leu | Val | Leu | Ser | Val | Pro | Asp | Lys | Asp | Lys | Tyr | Asp | Pro |  |
| 220 |  |  |  |  | 225 |  |  |  |  | 230 |  |  |  |  | 235 |  |

| ACA | GGA | GGG | GAA | ACA | ACA | GTA | CCC | CAA | GGG | ACA | CCA | GTT | TCA | GAT | AAA | 831 |
| Thr | Gly | Gly | Glu | Thr | Thr | Val | Pro | Gln | Gly | Thr | Pro | Val | Ser | Asp | Lys |  |
|  |  |  | 240 |  |  |  |  | 245 |  |  |  |  | 250 |  |  |  |

| GAA | ATC | ACA | GAC | TTA | GTT | AAG | ATT | CCA | GAT | GGC | TCA | AAA | GGG | GTT | CCG | 879 |
| Glu | Ile | Thr | Asp | Leu | Val | Lys | Ile | Pro | Asp | Gly | Ser | Lys | Gly | Val | Pro |  |
|  |  | 255 |  |  |  |  | 260 |  |  |  |  | 265 |  |  |  |  |

| ACA | GTT | GTT | GGT | GAT | CGT | CCA | GAT | ACT | AAC | GTT | CCT | GGA | GAT | CAT | AAA | 927 |
| Thr | Val | Val | Gly | Asp | Arg | Pro | Asp | Thr | Asn | Val | Pro | Gly | Asp | His | Lys |  |
|  | 270 |  |  |  |  | 275 |  |  |  |  | 280 |  |  |  |  |  |

| GTA | ACG | GTA | GAA | GTA | ACG | TAT | CCA | GAT | GGA | ACA | AAG | GAT | ACA | GTA | GAA | 975 |
| Val | Thr | Val | Glu | Val | Thr | Tyr | Pro | Asp | Gly | Thr | Lys | Asp | Thr | Val | Glu |  |
|  | 285 |  |  |  |  | 290 |  |  |  |  | 295 |  |  |  |  |  |

| GTA | ACG | GTT | CAT | GTG | ACA | CCA | AAA | CCA | GTA | CCG | GAT | AAA | GAT | AAA | TAT | 1023 |
| Val | Thr | Val | His | Val | Thr | Pro | Lys | Pro | Val | Pro | Asp | Lys | Asp | Lys | Tyr |  |
| 300 |  |  |  | 305 |  |  |  |  | 310 |  |  |  |  | 315 |  |  |

| GAT | CCA | ACA | GGT | AAA | GCT | CAG | CAA | GTC | AAC | GGT | AAA | GGA | AAT | AAA | CTA | 1071 |
| Asp | Pro | Thr | Gly | Lys | Ala | Gln | Gln | Val | Asn | Gly | Lys | Gly | Asn | Lys | Leu |  |
|  |  |  | 320 |  |  |  |  | 325 |  |  |  |  | 330 |  |  |  |

| CCA | GCA | ACA | GGT | GAG | AAT | GCA | ACT | CCA | TTC | TTT | AAT | GTT | GCA | GCT | TTG | 1119 |
| Pro | Ala | Thr | Gly | Glu | Asn | Ala | Thr | Pro | Phe | Phe | Asn | Val | Ala | Ala | Leu |  |

5,908,629

49

50

-continued

```
                335                 340                 345
ACA ATT ATA TCA TCA GTT GGT TTA TTA TCT GTT TCT AAG AAA AAA GAG    1167
Thr Ile Ile Ser Ser Val Gly Leu Leu Ser Val Ser Lys Lys Lys Glu
            350                 355                 360

GAT TAATCTTTTG ACCTAAAATG TCACTAAATT TTTCACCATT TATTGGTGTG         1220
Asp
365

AACACATTAA TAAAGTTATG CATCTCTCTC CAACAAAATT AATTAAAGTG TTTCAATTTT  1280

TCGAGATTAA TTCTTGAAAA AAGCCTATCG AGATTATTAA TTTCGATAGG CTTTTGATTT  1340

TGTGTAAGCG TCCAATATAC CTTGTTATTG GACGCTTACT                       1380
```

(2) INFORMATION FOR SEQ ID NO:15:

(i) SEQUENCE CHARACTERISTICS:
        (A) LENGTH: 364 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 310
        (D) OTHER INFORMATION: /note= "This feature indicates that
            the amino acid sequence from position 227 through
            309 is inserted at position 310 and may repeat up to
            eight times (for a total of nine repeating copies of
            these sequences within the polypeptide)."

(xi) SEQUENCE DESCRIPTION: SEQ ID NO:15:

```
Met Phe Arg Arg Ser Lys Asn Asn Ser Tyr Asp Thr Ser Gln Thr Lys
 1               5                  10                  15

Gln Arg Phe Ser Ile Lys Lys Phe Lys Phe Gly Ala Ala Ser Val Leu
                20                  25                  30

Ile Gly Leu Ser Phe Leu Gly Gly Val Thr Gln Gly Asn Leu Asn Ile
            35                  40                  45

Phe Glu Glu Ser Ile Val Ala Ala Ser Thr Ile Pro Gly Ser Ala Ala
        50                  55                  60

Thr Leu Asn Thr Ser Ile Thr Lys Asn Ile Gln Asn Gly Asn Ala Tyr
65                  70                  75                  80

Ile Asp Leu Tyr Asp Val Lys Leu Gly Lys Ile Asp Pro Leu Gln Leu
                85                  90                  95

Ile Val Leu Glu Gln Gly Phe Thr Ala Lys Tyr Val Phe Arg Gln Gly
            100                 105                 110

Thr Lys Tyr Tyr Gly Asp Val Ser Gln Leu Gln Ser Thr Gly Arg Ala
        115                 120                 125

Ser Leu Thr Tyr Asn Ile Phe Gly Glu Asp Gly Leu Pro His Val Lys
    130                 135                 140

Thr Asp Gly Gln Ile Asp Ile Val Ser Val Ala Leu Thr Ile Tyr Asp
145                 150                 155                 160

Ser Thr Thr Leu Arg Asp Lys Ile Glu Glu Val Arg Thr Asn Ala Asn
                165                 170                 175

Asp Pro Lys Trp Thr Glu Glu Ser Arg Thr Glu Val Leu Thr Gly Leu
            180                 185                 190

Asp Thr Ile Lys Thr Asp Ile Asp Asn Asn Pro Lys Thr Gln Thr Asp
        195                 200                 205

Ile Asp Ser Lys Ile Val Glu Val Asn Glu Leu Glu Lys Leu Leu Val
    210                 215                 220

Leu Ser Val Pro Asp Lys Asp Lys Tyr Asp Pro Thr Gly Gly Glu Thr
```

```
            225                 230                 235                 240
Thr Val Pro Gln Gly Thr Pro Val Ser Asp Lys Glu Ile Thr Asp Leu
                245                 250                 255
Val Lys Ile Pro Asp Gly Ser Lys Gly Val Pro Thr Val Gly Asp
            260                 265                 270
Arg Pro Asp Thr Asn Val Pro Gly Asp His Lys Val Thr Val Glu Val
        275                 280                 285
Thr Tyr Pro Asp Gly Thr Lys Asp Thr Val Glu Val Thr Val His Val
    290                 295                 300
Thr Pro Lys Pro Val Pro Asp Lys Asp Tyr Asp Pro Thr Gly Lys
305                 310                 315                 320
Ala Gln Gln Val Asn Gly Lys Gly Asn Lys Leu Pro Ala Thr Gly Glu
                325                 330                 335
Asn Ala Thr Pro Phe Phe Asn Val Ala Ala Leu Thr Ile Ile Ser Ser
            340                 345                 350
Val Gly Leu Leu Ser Val Ser Lys Lys Glu Asp
            355                 360
```

(2) INFORMATION FOR SEQ ID NO:16:

(i) SEQUENCE CHARACTERISTICS:
        (A) LENGTH: 56 amino acids
        (B) TYPE: amino acid
        (D) TOPOLOGY: both (ii) MOLECULE TYPE: peptide (xi) SEQUENCE DESCRIPTION: SEQ ID NO:16:

```
Met Phe Arg Arg Ser Lys Asn Asn Ser Tyr Asp Thr Ser Gln Thr Lys
1               5                   10                  15
Gln Arg Phe Ser Ile Lys Lys Phe Lys Phe Gly Ala Ala Ser Val Leu
                20                  25                  30
Ile Gly Leu Ser Phe Leu Gly Gly Val Thr Gln Gly Asn Leu Asn Ile
            35                  40                  45
Phe Glu Glu Ser Ile Val Ala Ala
        50                  55
```

(2) INFORMATION FOR SEQ ID NO:17:

(i) SEQUENCE CHARACTERISTICS:
        (A) LENGTH: 37 amino acids
        (B) TYPE: amino acid
        (D) TOPOLOGY: both (ii) MOLECULE TYPE: peptide (xi) SEQUENCE DESCRIPTION: SEQ ID NO:17:

```
Met Phe Lys Ser Asn Tyr Glu Arg Lys Met Arg Tyr Ser Ile Arg Lys
1               5                   10                  15
Phe Ser Val Gly Val Ala Ser Val Ala Val Arg Ser Leu Phe Met Gly
                20                  25                  30
Ser Val Ala His Ala
            35
```

(2) INFORMATION FOR SEQ ID NO:18:

(i) SEQUENCE CHARACTERISTICS:
        (A) LENGTH: 41 amino acids
        (B) TYPE: amino acid
        (D) TOPOLOGY: both (ii) MOLECULE TYPE: peptide (xi) SEQUENCE DESCRIPTION: SEQ ID NO:18:

Met Ala Arg Gln Gln Thr Lys Lys Asn Tyr Ser Leu Arg Lys Leu Lys
1               5                   10                  15

Thr Gly Thr Ala Ser Val Ala Val Ala Leu Thr Val Leu Gly Ala Gly
                20                  25                  30

Phe Ala Asn Gln Thr Glu Val Arg Ala
            35                  40

(2) INFORMATION FOR SEQ ID NO:19:

(i) SEQUENCE CHARACTERISTICS:
        (A) LENGTH: 42 amino acids
        (B) TYPE: amino acid
        (D) TOPOLOGY: both (ii) MOLECULE TYPE: peptide (xi) SEQUENCE DESCRIPTION: SEQ ID NO:19:

Met Thr Lys Asn Asn Thr Asn Arg His Tyr Ser Leu Arg Lys Leu Lys
1               5                   10                  15

Thr Gly Thr Ala Ser Val Ala Val Ala Leu Thr Val Leu Gly Ala Gly
                20                  25                  30

Leu Val Val Asn Thr Asn Glu Val Ser Ala
            35                  40

(2) INFORMATION FOR SEQ ID NO:20:

(i) SEQUENCE CHARACTERISTICS:
        (A) LENGTH: 41 amino acids
        (B) TYPE: amino acid
        (D) TOPOLOGY: both (ii) MOLECULE TYPE: peptide (xi) SEQUENCE DESCRIPTION: SEQ ID NO:20:

Met Ala Lys Asn Asn Thr Asn Arg His Tyr Ser Leu Arg Lys Leu Lys
1               5                   10                  15

Thr Gly Thr Ala Ser Val Ala Val Ala Leu Thr Val Leu Gly Ala Gly
                20                  25                  30

Phe Ala Asn Gln Thr Glu Val Lys Ala
            35                  40

(2) INFORMATION FOR SEQ ID NO:21:

(i) SEQUENCE CHARACTERISTICS:
        (A) LENGTH: 50 amino acids
        (B) TYPE: amino acid
        (D) TOPOLOGY: both (ii) MOLECULE TYPE: peptide (xi) SEQUENCE DESCRIPTION: SEQ ID NO:21:

Met Ala Lys Asn Asn Thr Asn Arg His Tyr Ser Leu Arg Lys Leu Lys
1               5                   10                  15

Thr Gly Thr Ala Ser Val Ala Val Ala Leu Thr Val Leu Gly Ala Gly
                20                  25                  30

Phe Ala Asn Gln Thr Glu Val Lys Ala Asn Gly Asp Gly Asn Pro Arg
            35                  40                  45

Glu Val
50

(2) INFORMATION FOR SEQ ID NO:22:

(i) SEQUENCE CHARACTERISTICS:
    (A) LENGTH: 45 amino acids
    (B) TYPE: amino acid
    (D) TOPOLOGY: both (ii) MOLECULE TYPE: peptide (xi) SEQUENCE DESCRIPTION: SEQ ID NO:22:

```
Lys Ala Gln Gln Val Asn Gly Lys Gly Asn Lys Leu Pro Ala Thr Gly
1               5                  10                  15
Glu Asn Ala Thr Pro Phe Phe Asn Val Ala Ala Leu Thr Ile Ile Ser
            20                  25                  30
Ser Val Gly Leu Leu Ser Val Ser Lys Lys Lys Glu Asp
        35                  40                  45
```

(2) INFORMATION FOR SEQ ID NO:23:

(i) SEQUENCE CHARACTERISTICS:
       (A) LENGTH: 46 amino acids
       (B) TYPE: amino acid
       (D) TOPOLOGY: both (ii) MOLECULE TYPE: peptide (xi) SEQUENCE DESCRIPTION: SEQ ID NO:23:

```
Asn Lys Ala Pro Met Lys Glu Thr Lys Arg Gln Leu Pro Tyr Thr Gly
1               5                  10                  15
Val Thr Ala Asn Pro Phe Phe Ala Ala Ala Leu Thr Val Met Ala
            20                  25                  30
Thr Ala Gly Val Ala Ala Val Val Lys Arg Lys Glu Glu Asn
        35                  40                  45
```

(2) INFORMATION FOR SEQ ID NO:24:

(i) SEQUENCE CHARACTERISTICS:
       (A) LENGTH: 45 amino acids
       (B) TYPE: amino acid
       (D) TOPOLOGY: both (ii) MOLECULE TYPE: peptide (xi) SEQUENCE DESCRIPTION: SEQ ID NO:24:

```
Arg Pro Ser Gln Asn Lys Gly Met Arg Ser Gln Leu Pro Ser Thr Gly
1               5                  10                  15
Glu Ala Ala Asn Pro Phe Phe Thr Ala Ala Ala Thr Val Met Val
            20                  25                  30
Ser Ala Gly Met Leu Ala Leu Lys Arg Lys Glu Glu Asn
        35                  40                  45
```

(2) INFORMATION FOR SEQ ID NO:25:

(i) SEQUENCE CHARACTERISTICS:
       (A) LENGTH: 46 amino acids
       (B) TYPE: amino acid
       (D) TOPOLOGY: both (ii) MOLECULE TYPE: peptide (xi) SEQUENCE DESCRIPTION: SEQ ID NO:25:

```
Ala Lys Lys Glu Asp Ala Lys Lys Ala Glu Thr Leu Pro Thr Thr Gly
1               5                  10                  15
Glu Gly Ser Asn Pro Phe Phe Thr Ala Ala Leu Ala Val Met Ala
            20                  25                  30
Gly Ala Gly Ala Leu Ala Val Ala Ser Lys Arg Lys Glu Asp
```

35          40          45

(2) INFORMATION FOR SEQ ID NO:26:

(i) SEQUENCE CHARACTERISTICS:
       (A) LENGTH: 46 amino acids
       (B) TYPE: amino acid
       (D) TOPOLOGY: both (ii) MOLECULE TYPE: peptide (xi) SEQUENCE DESCRIPTION: SEQ ID NO:26:

Ala Lys Lys Asp Asp Ala Lys Lys Ala Glu Thr Leu Pro Thr Thr Gly
1               5                   10                  15

Glu Gly Ser Asn Pro Phe Phe Thr Ala Ala Ala Leu Ala Val Met Ala
            20                  25                  30

Gly Ala Gly Ala Leu Ala Val Ala Ser Lys Arg Lys Glu Asp
            35                  40                  45

(2) INFORMATION FOR SEQ ID NO:27:

(i) SEQUENCE CHARACTERISTICS:
       (A) LENGTH: 45 amino acids
       (B) TYPE: amino acid
       (D) TOPOLOGY: both (ii) MOLECULE TYPE: peptide (xi) SEQUENCE DESCRIPTION: SEQ ID NO:27:

Ser Arg Ser Ala Met Thr Gln Gln Lys Arg Thr Leu Pro Ser Thr Gly
1               5                   10                  15

Glu Thr Ala Asn Pro Phe Phe Thr Ala Ala Ala Ala Thr Val Met Val
            20                  25                  30

Ser Ala Gly Met Leu Ala Leu Lys Arg Lys Glu Glu Asn
            35                  40                  45

(2) INFORMATION FOR SEQ ID NO:28:

(i) SEQUENCE CHARACTERISTICS:
       (A) LENGTH: 34 amino acids
       (B) TYPE: amino acid
       (D) TOPOLOGY: both (ii) MOLECULE TYPE: peptide (xi) SEQUENCE DESCRIPTION: SEQ ID NO:28:

Asn Lys Ala Pro Met Lys Glu Thr Lys Arg Gln Leu Pro Ser Thr Gly
1               5                   10                  15

Glu Thr Ala Asn Pro Phe Phe Thr Ala Ala Ala Leu Thr Val Met Ala
            20                  25                  30

Ala Ala (2) INFORMATION FOR SEQ ID NO:29:

(i) SEQUENCE CHARACTERISTICS:
       (A) LENGTH: 44 amino acids
       (B) TYPE: amino acid
       (D) TOPOLOGY: both (ii) MOLECULE TYPE: peptide (xi) SEQUENCE DESCRIPTION: SEQ ID NO:29:

Lys Gly Asn Pro Thr Ser Thr Thr Glu Lys Lys Leu Pro Tyr Thr Gly
1               5                   10                  15

Val Ala Ser Asn Leu Val Leu Glu Ile Met Gly Leu Leu Gly Leu Ile

```
            20                  25                  30
Gly Thr Ser Phe Ile Ala Met Lys Arg Arg Lys Ser
        35                  40
```

(2) INFORMATION FOR SEQ ID NO:30:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

CCTAG                                                                5

(2) INFORMATION FOR SEQ ID NO:31:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GATCC                                                                 5

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GATCCATTGT GCTGG                                     15

(2) INFORMATION FOR SEQ ID NO:33:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GTAACACGAC C                                              11

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CCTAGGTAAC ACGACC                                    16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CCAGCACAAT GGATCC                            16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GGTCGTGTTA CCTAGG                            16

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

CCTAGGTAAC ACGACCGGTC GTGTTACCTA GG             32

(2) INFORMATION FOR SEQ ID NO:38:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CCTAGGTA                                       8

(2) INFORMATION FOR SEQ ID NO:39:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

ATGGATCC                                       8

(2) INFORMATION FOR SEQ ID NO:40:

(i) SEQUENCE CHARACTERISTICS:
        (A) LENGTH: 12 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GTGTTACCTA GG                                                        12

(2) INFORMATION FOR SEQ ID NO:41:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

CTTTAGAGCA CA                                                        12

(2) INFORMATION FOR SEQ ID NO:42:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GAAATCTC                                                              8

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

CTTTAGAGCA CAATGGATCC                                                20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GAAATCTCGT GTTACCTAGG                                                20

(2) INFORMATION FOR SEQ ID NO:45:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

CTCTAAAG                                                                                    8

(2) INFORMATION FOR SEQ ID NO:46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

ACACGAGATT TC                                                                              12

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

CCTAGGTAAC ACGAGATTTC                                                                      20

(2) INFORMATION FOR SEQ ID NO:48:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

AATTCG                                                                                      6

(2) INFORMATION FOR SEQ ID NO:49:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

TGCTTAA                                                                                     7

(2) INFORMATION FOR SEQ ID NO:50:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GCTTAATTAA GC                                                                              12

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

AATTCGAGCT                                                10

(2) INFORMATION FOR SEQ ID NO:52:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

CGCCCGGGG                                                 9

(2) INFORMATION FOR SEQ ID NO:53:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

TTAAGC                                                      6

(2) INFORMATION FOR SEQ ID NO:54:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

TCGAGCGGGC CCC                                        13

(2) INFORMATION FOR SEQ ID NO:55:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

TTAAGCGCGG GCCCC                                     15

(2) INFORMATION FOR SEQ ID NO:56:

(i) SEQUENCE CHARACTERISTICS:
        (A) LENGTH: 10 base pairs

-continued (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

AATTCGAGCT                                                                10

(2) INFORMATION FOR SEQ ID NO:57:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CGCCCGGGG                                                                 9

(2) INFORMATION FOR SEQ ID NO:58:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

TTAAGC                                                                    6

(2) INFORMATION FOR SEQ ID NO:59:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

TCGAGCGGGC CCC                                                           13

(2) INFORMATION FOR SEQ ID NO:60:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

AATTC                                                                     5

(2) INFORMATION FOR SEQ ID NO:61:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: cDNA

```
        (xi) SEQUENCE DESCRIPTION: SEQ ID NO:61:

TTAAG                                                                        5

(2) INFORMATION FOR SEQ ID NO:62:

(i) SEQUENCE CHARACTERISTICS:
             (A) LENGTH: 4 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:62:

GGGG                                                                         4

(2) INFORMATION FOR SEQ ID NO:63:

(i) SEQUENCE CHARACTERISTICS:
             (A) LENGTH: 4 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:63:

CCCC                                                                         4

(2) INFORMATION FOR SEQ ID NO:64:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:64:

AATTCGGGG                                                                    9

(2) INFORMATION FOR SEQ ID NO:65:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:65:

TTAAGCCCC                                                                    9
```

CONJUGATE VACCINE FOR GROUP B STREPTOCOCCUS

CROSS REFERENCE TO RELATED APPLICATIONS

This application is a division of application Ser. No. 08/363,311, filed Dec. 22, 1994, now U.S. Pat. No. 5,648, 241 which is a continuation of application Ser. No. 07/968, 866, filed Nov. 2, 1992, now abandoned, which is a continuation-in-part of U.S. application Ser. No. 07/408, 036, filed Sep. 15, 1989, now abandoned.

This invention was made with government support; the government has certain rights in this invention.

FIELD OF THE INVENTION

The invention relates to the fields of microbiology and vaccine technology, and concerns the development of a vaccine capable of conferring immunity to infection by group B Streptococcus.

BACKGROUND OF THE INVENTION

Bacteria of the Streptococcus genus have been implicated as causal agents of disease in humans and animals. The Streptococci have been divided into immunological groups based upon the presence of specific carbohydrate antigens on their cell surfaces. At present, groups A through O are recognized (Davis, B. D. et al., In: *Microbiology*, 3rd. Edition, page 609, (Harper & Row, 1980). Streptococci are among the most common and important bacteria causing human disease. Although Streptococci of the B group are associated with animal disease (such as mastitis-in cattle), *Streptococcus agalactiae* (a group B Streptococd) has emerged as the most common cause of human neonatal sepsis in the United States and is thought to be responsible for over 6000 deaths annually (Hill, H. R. et al., *Sexually Transmitted Diseases*, McGraw Hill, pp. 397–407). Group B Streptococcus is also an important pathogen in late-onset meningitis in infants, in postpartum endometritis, and in infections in immunocompromised adults (Patterson, M. J. et al., *Bact. Rev.* 40:774–792 (1976)). Although the organism is sensitive to antibiotics, the high attack rate and rapid onset of sepsis in neonates and meningitis in infants results in both high morbidity (50%) and mortality (20%) (Baker, C. J. et al., *New Eng. J. Med.* (Editorial) 314(26):1702–1704 (1986); Baker, C. J. et al., *J. Infect. Dis.* 136:137–152 (1977)).

Group B Streptococcus is a common component of normal human vaginal and colonic flora. While the most common route of neonatal infection is intrapartum from vaginal colonization, nosocomial spread in newborn nurseries has also been described (Patterson, M. J. et al., *Bact. Rev.* 40:774–792 (1976)). However, only a small percentage of infants colonized with group B Streptococcus develop serious infections. The role of both host factors and bacterial virulence determinants in the transition from colonization to infection is not well understood.

Several proteins from group B Streptococcus are thought to have a role in virulence and immunity (Ferrieri, P, *Rev. Infect. Dis.* 10:S363 (1988)). In 1975, Lancefield defined the C proteins of group B Streptococcus by their ability to elicit protective immunity (Lancefield, R. C, et at., *J. Exp. Med.* 142:165–179 (1975)). This group of proteins is thought to contain several different polypeptides and antigenic determinants. In view of these findings, efforts to prevent infections with group B Streptococcus have been directed towards the use of prophylactic antibiotics and the development of a vaccine against group B Streptococcus (Baker, C. J, et al., *Rev. of Infec. Dis.* 7:458–467 (1985), Baker, C. J. et al., *New Eng. J. Med. (Editorial)* 314(26):1702–1704 (1986)). Polysaccharide vaccines against group B Streptococcus are described by Kasper, D. L. (U.S. Pat. No. 4,207,414 and U.S. Pat. No. RE31672, and U.S. Pat. Nos. 4,324,887, 4,356,263, 4,367,221, 4,367,222, and 4,367, 223), by Carlo, D. J. (U.S. Pat. No. 4,413,057, European Patent Publication 38,265), and by Yavordios, D. et al (European Patent Publication 71,515), all of which references are incorporated herein by reference.

Except for the small sub-population of infants in whom both maternal colonization with group B Streptococcus and other perinatal risk factors can be identified, the use of prophylactic antibiotics has not been practical or efficacious in preventing the majority of cases (Boyer, K. M, et al., *New Eng. J. Med.* 314(26):1665–1669 (1986)). Intrapattum chemoprophylaxis has not gained wide acceptance for the following reasons: (1) It has not been possible to identify maternal colonization by group B Streptococcus in a fast, reliable and cost-effective manner; (2) About 40% of neonatal cases occur in low-risk settings; (3) It has not been considered practical to screen and/or treat all mothers or infants who are potentially at risk; and (4) antibiotic prophylaxis has not appeared to be feasible in preventing late-onset meningitis (7200 cases per year in the United States) or postpartum endometritis (45,000 cases annually) (Baker, C. J. et al., *New Eng. J. Med.* (Editorial) 314:1702–1704 (1986)).

DEPOSIT OF MICROORGANISMS

Plasmids pJMS1 and pJMS23 are derivatives of plasmid pUX12 which contain DNA capable of encoding antigenic Streptococci proteins that may be used in accordance with the present invention. Plasmid pUX12 is a derivative of plasmid pUC12. Plasmids pJMS1 and pJMS23 were deposited on Sep. 15, 1989, at the American Type Culture Collection, Rockville, Md. and given the designations ATCC 40659 and ATCC 40660, respectively.

SUMMARY OF THE INVENTION

Streptococcus agalactiae is the most common cause of neonatal sepsis in the United States and is responsible for between 6,000 and 10,000 deaths per year. While the type-specific polysaccharide capsule of group B Streptococcus is immunogenic and carries important protective antigens, clinical trials of a polysaccharide vaccine have shown a poor response rate (Baker, C. J. et al., *New Engl. J. Med.* 319:1180 (1980); Insel, R. A, et al., *New Eng. J. Med.* (Editorial) 319(18):1219–1220 (1988)).

The present invention concerns the development of a conjugate vaccine to group B Streptococcus, (i.e. *Streptococcus agalactiae*) that utilizes to a protective protein antigen expressed from a gene cloned from group B Streptococcus. This novel conjugate vaccine has the advantages both of eliciting T-cell dependent protection via the adjuvant action of the carrier protein and also providing additional protective epitopes that are present on the cloned group B Streptococcus protein (Insel, R. A, et al., *New Eng. J. Med.* (Editorial) 319(18):1219–1220 (1988); Baker, C. J, et al., *Rev. of Infec. Dis.* 7:458–467 (1985)).

In detail, the invention provides a conjugate vaccine capable of conferring host immunity to an infection by group B Streptococcus which comprises (a) a polysaccharide conjugated to (b) a protein; wherein both the polysaccharide and the protein are characteristic molecules of the group B Streptococcus, and wherein the protein is a derivative of the C protein alpha antigen that retains the ability to elicit protective antibodies against the group B Streptococcus.

The invention also concerns a method for preventing or attenuating an infection caused by a group B Streptococcus which comprises administering to an individual, suspected of being at risk for such an infection, an effective amount of the conjugate vaccine of the invention, such that it provides host immunity against the infection.

The invention further concerns a method for preventing or attenuating infection caused by a group B Streptococcus which comprises administering to a pregnant female an effective amount of a conjugate vaccine of the invention, such that it provides immunity to the infection to an unborn offspring of the female.

The invention also provides a method for preventing or attenuating an infection caused by a group B Streptococcus which comprises administering to an individual suspected of being at risk for such an infection an effective amount of an antisera elicited from the exposure of a second individual to a conjugate vaccine of the invention, such that is provides host immunity to the infection.

BRIEF DESCRIPTION OF THE FIGURES

FIGS. 3A–3C SEQ ID NOS. 48–65 shows the modifications which were made to pUX12 in order to produce the +1 reading frame plasmid pUX12+1 FIG. 3A and which produce the −1 reading frame plasmid pUX12−1 FIG. 3C. FIG 3B shows a construction which is additionally capable of resulting in a −1 reading frame plasmid.

FIG. 6A–6C shows the nucleotide [SEQ ID NO: 14] and deduced amino acid sequences [SEQ ID NO: 15] of bca and the flanking regions. The DNA strand is shown 5' to 3', and nucleotides are listed on the upper line beginning 78 base pairs upstream from the open reading frame. The deduced amino acid sequence for the open reading frame is below the nucleic acid sequence. The G+C content of 40% and the codon usage are similar to other streptococcal genes (Hollingshead, S. K. et al., *J. Biol. Chem.* 261:1677–1686 (1986)). Highlighted features include the −10 (TATAAT) promoter consensus site, ribosomal binding site (RBS), signal sequence, repeat region 1, the C terminus, with the termination codon (TAA) at position 3161, and two regions of dyad symmetry that are potential transcriptional terminators.

FIG. 7A–7B show homologies to the putative signal sequences and C-terminal membrane anchor of the C protein alpha antigen, respectively. FIG. 7A: the N terminus of the C protein alpha antigen on the top line (sequence 1) [SEQ ID NO: 16] and is compared with the following Gram-positive signal sequences (accession codes are listed for each of the sequence numbers): sequence 2 [SEQ ID NO: 17], the C protein beta antigen (S 15330; STRBAGBA) and four M proteins of group A Streptococcus; sequence 3 [SEQ ID NO: 18], ennX (STRENNX); sequence 4 [SEQ ID NO: 19], emm24 (STREMM24); sequence 5 [SEQ ID NO: 20], M1 (S06767); sequence 6 [SEQ ID NO: 21], S01260. Lysine (K) and arginine (R) residues preceding the underlined hydrophobic stretch are in boldface type, as are serine (S) and threonine (T) residues preceding the probable signal cleavage sites. The probable cleavage site for the alpha signal is following the valine at position 41; however, alternative cleavage sites exist at positions 53–56. FIG. 7B: The C terminus of the C protein alpha antigen is shown on the top line (sequence 1) [SEQ ID NO: 22] and compared with the following Gram-positive membrane anchor peptides: sequence 2 [SEQ ID NO: 23], M5 (A28616, M6 (A26297), and M24 (A28549); sequence 3 [SEQ ID NO: 24], ennX (STREENX); sequence 4 [SEQ ID NO: 25], S00128, STRPROTG, and A26314; sequence 5 [SEQ ID NO: 26], spg (A24496); sequence 6 [SEQ ID NO: 27], arp4 (S05568) and emm49 (STRM49NX, STRMM24); and sequence 7 [SEQ ID NO: 28], emm12 (STR12M), M5, M6, M24, emm12, emm49, and ennX are all M proteins; arp4 is a binding protein of group A Streptococcus. S00128, STRPROTG, spg, and A26314 are IgG binding proteins of group G Streptococcus. Sequence 8 [SEQ ID NO: 29] illustrates the membrane anchor for the beta antigen, which lacks the PPFFXXAA [SEQ ID NO: 1] motif. Highlighted areas include lysine residues (K) preceding the LPXTGE [SEQ ID NO: 2] motif (boxed), the hydrophobic region (underlined) with the PPFFXXAA [SEQ ID NO: 1] consensus (boxed and underlined), and the terminal amino acid aspartic acid (D) or asparagine (N).

DESCRIPTION OF THE PREFERRED EMBODIMENTS

Significance and Clinical Perspective

Figure 1:
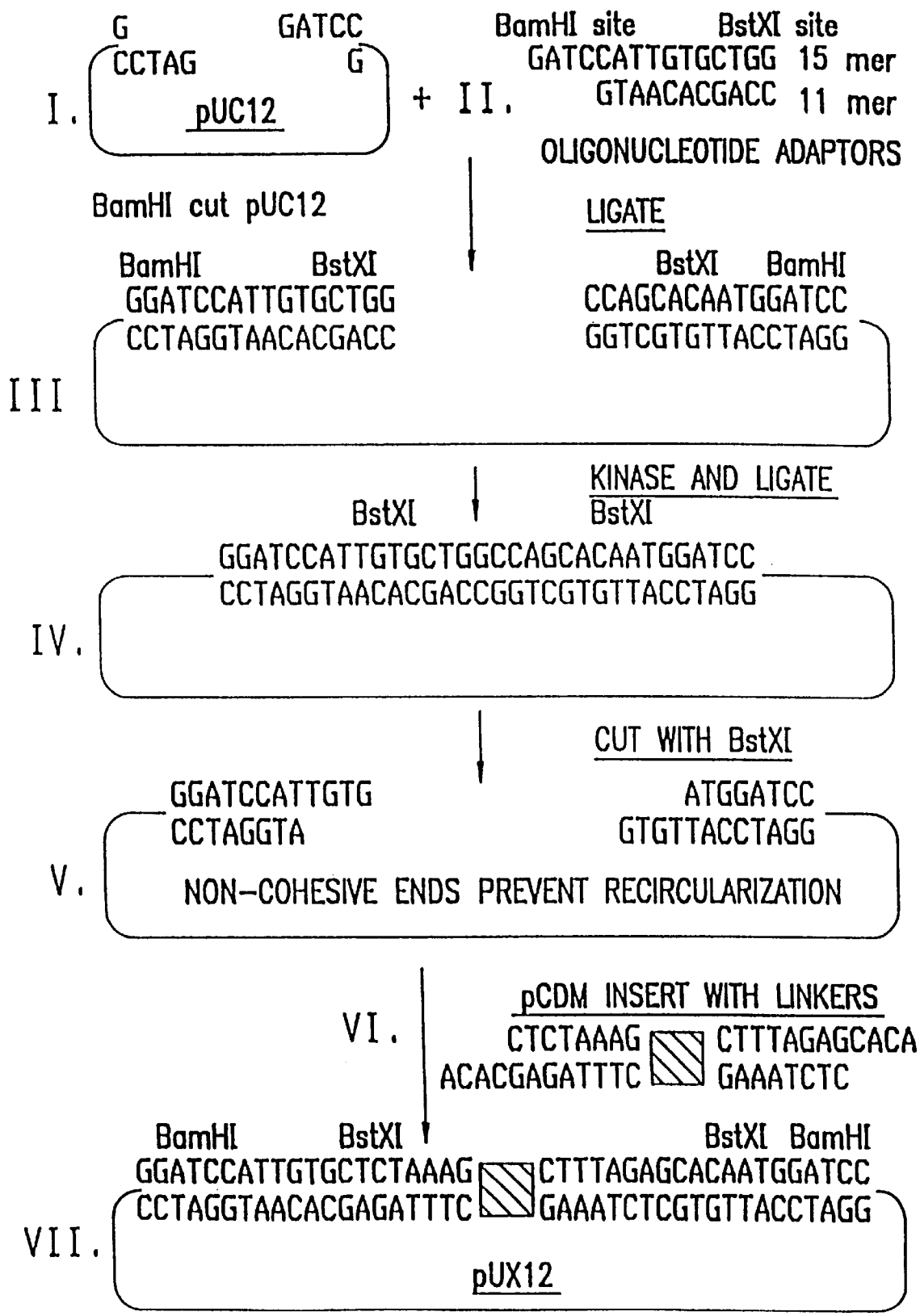
FIG. 1 SEQ ID NOS. 30–47 shows the modifications of pUC12 to create the plasmid pUX12.

Maternal immunoprophylaxis with a vaccine to group B Streptococcus has been proposed as a potential route for protecting against infection both in the mother and in the young infant through the peripartum transfer of antibodies (Baker, C. J. et al., *New Eng. J. Med.* (Editorial) 314(26) :1702–1704 (1986); Baker, C. J. et al., *New Eng. J. Med.* 319:1180 (1988); Baker, C. J. et al., *J. Infect. Dis.* 7:458 (1985)). As is the case with other encapsulated bacteria, susceptibility to infection correlates with the absence of type-specific antibody (Kasper, D. L., et al., *J. Clin. Invest.* 72:260–269 (1983), Kasper, D. L., et al., *Antibiot. Chemother.* 35:90–100 (1985)). The lack of opsonically active type-specific anti-capsular antibodies to group B Streptococcus is a risk factor for the development of disease following colonization with group B Streptococcus (Kasper, D. L. et al., *J. Infec. Dis.* 153:407–415 (1986)).

One approach has been to vaccinate with purified type-specific capsular polysaccharides. Methods of producing such vaccines, and the use of such vaccines to immunize against group B Streptococcus are disclosed by Kasper, D. L. (U.S. Pat. No. 4,207,414 and U.S. Pat. No. RE31672, and U.S. Pat. Nos. 4,324,887, 4,356,263, 4,367,221, 4,367,222, and 4,367,223), by Carlo, D. J. (U.S. Pat. No. 4,413,057, European Patent Publication 38,265), and by Yavordios, D. et al. (European Patent Publication 71,515), all of which references are incorporated herein by reference.

Although the polysaccharide capsule of group B Streptococcus is well characterized and has been shown to play a role in both virulence and immunity (Kasper, D. L. *J. Infect. Dis.* 153:407 (1986)), these capsular components have been found to vary in their immunogenicity depending both on the specific capsular type and on factors in the host's immune system (Baker, C. J, et al., *Rev. of Infec. Dis.* 7:458467 (1985)). A recently completed clinical trial evaluating a capsular polysaccharide vaccine of group B Streptococcus showed an overall response rate of 63% and indicated that such a vaccine was not optimally immunogenic (Baker C. J, et al., *New Eng. J. Med.* 319(18) :1180–1185 (1988)).

Differences in immunogenicity have also been observed with the capsular polysaccharides of other bacteria. For example, the vaccine against the type C meningococcal capsule is highly active while the group B meningococcal polysaccharide vaccine is not immunogenic (Kasper, D. L. et al., *J. Infec. Dis.* 153:407415 (1986)). T-cell independent functions of the host's immune system are often required for mounting an antibody response to polysaccharide antigens. The lack of a T-cell independent response to polysaccharide antigens may be responsible for the low levels of antibody against group B Streptococcus present in mothers whose children subsequently develop an infection with group B Streptococcus. In addition, children prior to 18 or 24 months of age have a poorly developed immune response to T-cell independent antigens.

Determinants of Virulence and Immunity in group B Streptococcus

There are five serotypes of group B Streptococcus that share a common group specific polysaccharide antigen. However, antibody of the group antigen is not protective in animal models. Lancefield originally classified group B Streptococcus into four serotypes (Ia, Ib, II and III) using precipitin techniques. The composition and structure of the unique type-specific capsular polysaccharides for each of the serotypes was subsequently determined (Jennings, H. J, et al., *Biochem.* 22:1258–1264 (1983), Kasper, D. L. et al., *J. Infec. Dis.* 153:407–415 (1986), Wessels, M. R, et al., *Trans. Assoc. Amer. Phys.* 98:384–391 (1985)). Wilkinson defined a fifth serotype, Ic, by the identification of a protein antigen (originally called the Ibc protein) present on all strains of serotype Ib and some strains with the type Ia capsule (Wilkinson, H. W, et al., *J. Bacteriol.* 97:629–634 (1969), Wilkinson, H. W, et al., *Infec. and Immun.* 4:596604 (1971)). This protein was later found to vary in prevalence between the different serotypes of group B Streptococcus but was absent in serotype Ia (Johnson, D. R, et al., *J. Clin. Microbiol* 19:506–510 (1984)).

The nomenclature has recently been changed to classify the serotypes of group B Streptococcus solely by the capsular type-specific polysaccharides, and a fifth capsular type has also been described (type IV) (Pritchard, D. G, et al., *Rev. Infec. Dis.* 10(8):5367–5371 (1988)). Therefore, the typing of group B Streptococus strains is no longer based on the antigenic Ibc protein, which is now called the C protein. The type Ic strain is reclassified as serotype Ia on the basis of its capsular polysaccharide composition, with the additional information that it also carries the C protein.

Immunological, epidemiological and genetic data suggest that the type-specific capsule plays an important role in immunity to group B Streptococcus infections. The composition and structure of the type-specific capsular polysaccharides and their role in virulence and immunity have been the subjects of intensive investigation (Ferrieri, P. et al., *Infec. Immun.* 27:1023–1032 (1980), Krause, R. M, et al., *J. Exp. Med.* 142:165–179 (1975), Levy, N. J, et al., *J. Infec. Dis.* 149:851–860 (1984), Wagner, B, et al., *J. Gen. Microbiol.* 118:95–105 (1980), Wessels, M. R, et al., *Trans. Assoc. Amer. Phys.* 98:384–391 (1985)).

Controversy has existed regarding the structural arrangement of the type-specific and group B streptococcal polysaccharides on the cell surface, on the immunologically important determinants with in the type-specific polysaccharide, and on the mechanisms of capsule determined virulence of group B Streptococcus (Kasper, D. L. et al., *J. Infec. Dis.* 153:407–415 (1986)). To study the role of the capsule in virulence, Rubens et al. used transposon mutagenesis to create an isogeneic strain of type III group B Streptococcus that is unencapsulated (Rubens, C. E, et al., *Proc. Natl. Acad. Sci. USA* 84:7208–7212 (1987)). They demonstrated that the loss of capsule expression results in significant loss of virulence in a neonatal rat model. However, the virulence of clinical isolates with similar capsular composition varies widely. This suggests that other bacterial virulence factors, in addition to capsule, play a role in the pathogenesis of group B Streptococcus.

A number of proteins and other bacterial products have been described in group B Streptococcus whose roles in virulence and immunity have not been established, CAMP (Christine Atkins-Much Peterson) factor, pigment (probably carotenoid), R antigen, X antigen, anti-phagocytic factors and poorly defined "pulmonary toxins" (Ferrieri, P, et al., *J. Exp. Med.* 151:56–68 (1980); Ferrieri, P. et al., *Rev. Inf. Dis.* 10(2):1004–1071 (1988); Hill, H. R. et al., *Sexually Transmitted Diseases*, McGraw-Hill, pp. 397–407). The C proteins are discussed below.

Isogeneic strains of group B Streptococcus lacking hemolysin show no decrease in virulence in the neonatal rat model (Weiser, J. N, et al., *Infec. and Immun.* 55:2314–2316 (1987)). Both hemolysin and neuraminidase are not always present in clinical isolates associated with infection. The CAMP factor is an extracellular protein of group B Streptococcus with a molecule weight of 23,500 daltons that in the presence of staphylococcal beta-toxin (a sphingomyelinase) leads to the lysis of erythrocyte membranes. The gene for the CAMP factor in group B Streptococcus was recently cloned and expressed in *E. coli* (Schneewind, O, et al., *Infec. and Immun.* 56:2174–2179 (1988)). The role, if any, of the CAMP factor, X and R antigens, and other factors listed above in the pathogenesis of group B Streptococcus is not disclosed in the prior art (Fehrenbach, F. J, et al., In: *Bacterial Protein Toxins*, Gustav Fischer Verlag, Stuttgart (1988); Hill, H. R. et al., *Sexually Transmitted Diseases*, McGraw-Hill, NY, pp. 397–407 (1984)).

The C protein(s) are a group of a cell surface associated protein antigens of group B Streptococcus that were originally extracted from group B Streptococcus by Wilkinson et al. (Wilkinson, H. W, et al., *J. Bacteriol.* 97:629–634 (1969), Wilkinson, H. W, et al., *Infec. and Immun.* 4:596–604 (1971)). They used hot hydrochloric acid (HCl) to extract the cell wall and trichloroacetic acid TCA) to precipitate protein antigens. Two antigenically distinct populations of C proteins have been described: (1) A group of proteins that are sensitive to degradation by pepsin but not by trypsin, and called either TR (trypsin resistant) or alpha (α). (2) Another group of group B Streptococcus proteins that are sensitive to degradation by both pepsin and trypsin, and called TS (trypsin sensitive) or beta (β) (Bevanger, L, et al., *Acta Path. Microbiol. Scand Sect. B.* 87:51–54 (1989), Bevanger, L, et al., *Acta Path. Microbiol. Scand. Sect. B.* 89:205–209 (1981), Bevanger, L. et al., *Acta Path. Microbiol. Scand. Sect. B.* 91:231–234 (1983), Bevanger, L. et al., *Acta Path. Microbiol. Scand. Sect. B.* 93:113–119 (1985), Bevanger, L, et al., *Acta Path. Microbiol. Immunol. Scand. Sect. B.* 93:121–124 (1985), Johnson, D. R, et al., *J. Clin. Microbiol.* 19:506–510 (1984), Russell-Jones, G. J, et al., *J. Exp. Med.* 160:1476–1484 (1984)).

In 1975, lancefield et al. used mouse protection studies with antisera raised in rabbits to define the C proteins functionally for their ability to confer protective immunity against group B Streptococcus strains carrying similar protein antigens (Lancefield, R. C, et al., *J. Exp. Med.* 142:165–179 (1975)). Numerous investigators have obtained crude preparations of antigenic proteins from group B Streptococcus, that have been called C proteins, by chemical extraction from the cell wall using either HCl or detergents (Bevanger, L, et al., *Acta Path. Microbiol. Scand. Sect. B.* 89:205–209 (1981), Bevanger, L. et al., *Acta Path. Microbiol. Scand. Sect. B.* 93:113–119 (1985), Russell-Jones, G. J, et al., *J. Exp. Med.* 160:14761484 (1984), Valtonen, M. V, et al., *Microb. Path.* 1:191–204 (1986), Wilkinson, H. W, et al., *Infec. and Immun.* 4:596–604 (1971)). The reported sizes for these antigens have varied between 10 and 190 kilodaltons, and a single protein species has not been isolated or characterized (Ferrieri, P. et al., *Rev. Inf. Dis.* 10(2):1004–1071 (1988)).

By screening with protective antisera, C proteins can be detected in about 60% of clinical isolates of group B Streptococcus, and are found in all serotypes but with differing frequencies (Johnson, D. R, etal., *J. Clin. MicrobioL* 19:506–510 (1984)). Individual group B Streptococcus isolates may have both the TR and TS antigens, or only one, or neither of these antigens. Except for the ability of the partially purified antigens to elicit protective immunity, the role of these antigens in pathogenesis has not been studied in vitro. In Wvo studies with group B Streptococcus strains that carry C proteins provides some evidence that the C proteins may be responsible for resistance to opsonization (Payne, N. R, et al., *J. Infec. Dis.* 151:672–681 (1985)), and the C proteins may inhibit the intracellular killing of group B Streptococcus following phagocytosis (Payne, N. R, et al., *Infect. and Immun.* 55:1243–1251 (1987)). It has been shown that type II strains of group B Streptococcus carrying the C proteins are more virulent in the neonatal rat sepsis model (Ferrieri, P, et al., *Infect. Immun.* 27:1023–1032 (1980), Ferrieri, P. et al., *Rev. Inf. Dis.* 10(2):1004–1071 (1988)). Since there is no genetic data on the C proteins, isogeneic strains lacking the C proteins have not previously been studied. There is evidence that one of the TS, or β, C proteins binds to IgA (Russell-Jones, G. J, et al., *J. Exp. Med.* 160:1476–1484 (1984)). The role, if any, that the binding of IgA by the C proteins has on virulence is, however, not disclosed.

In 1986, Valtonen et al. isolated group B Streptococcus proteins from culture supernatants that elicit protection in the mouse model (Valtonen, M. V, et al., *Microb. Path.* 1:191–204 (1986)). They identified, and partially purified, a trypsin resistant group B Streptococcus protein with a molecular weight of 14,000 daltons. Antisera raised to this protein in rabbits protected mice against subsequent challenge with type Ib group B Streptococcus (89% protection). This protein is, by Lancefield's definition, a C protein. However, when antisera raised against this protein were used to immunoprecipitate extracts of group B Streptococcus antigens, a number of higher molecular weight proteins were found to be reactive. This suggested that the 14,000 m.w. protein may represent a common epitope of several group B Streptococcus proteins, or that it is a degradation product found in the supernatants of group B Streptococcus cultures. The diversity in the sizes in C proteins isolated from both the bacterial cells and supernatants suggests that the C proteins may represent a gene family, and maintain antigenic diversity as a mechanism for protection against the immune system.

The range of reported molecular weights and difficulties encountered in purifying individual C proteins are similar to the problems that many investigators have faced in isolating the M protein of group A Streptococcus (Dale, J. B, et al., *Infec. and Inmun.* 46(1):267–269 (1984), Fischetti, V. A, et al., *J. Exp. Med.* 144:32–53 (1976), Fischetti, V. A, et al., *J. Exp. Med* 146:1108–1123 (1977)). The gene for the M protein has now been cloned and sequenced, and found to contain a number of repeated DNA sequences (Hollingshead, S. K, et al., *J. Biol. Chem.* 261:1677–1686 (1986), Scott, J. R, et al., *Proc. Natl. Acad. Sci USA* 82:1822–1826 (1986), Scott, J. R, et al., *Infec. and Inmunn.* 52:609–612 (1986)). These repeated sequences may be responsible for post-transcriptional processing that results in a diversity in the size of M proteins that are produced. The mechanism by which this occurs is not understood. The range of molecular weights described for the C proteins of group B Streptococcus might result from a similar process.

Cleat et al. attempted to clone the C proteins by using two preparations of antisera to group B Streptococcus obtained from Bevanger (α and β) to screen a library of group B Streptococcus DNA in *E. coli* (Bevanger, L. et al., *Acta Path. Microbiol. Immunol. Scand. Sect. B.* 93:113–119 (1985), Cleat, P. H, et al., *Infec. and Innun.* 55(5): 1151–1155 (1987), which references are incorporated herein by reference). These investigators described two clones that produce proteins that bind to antistreptococcal antibodies. However, they failed to determine whether either of the cloned proteins had the ability to elicit protective antibody, or whether the prevalence of these genes correlated the with group B Streptococcus strains known to carry the C proteins. The role of the cloned gene sequences in the virulence of group B Streptococcus was not investigated. Since the C proteins are defined by their ability to elicit protective antibodies, this work failed to provide evidence that either of the clones encodes a C protein.

The Conjugated Vaccine of the Present Invention

The present invention surmounts the above-discussed deficiencies of prior vaccines to group B Streptococcus through the development of a conjugate vaccine in which the capsular polysaccharides are covalently linked to a protein backbone. This approach supports the development of a T-cell dependent antibody response to the capsular polysaccharide antigens and circumvents the T-cell independent requirements for antibody production (Baker, C. J, et al., *Rev. of Infec. Dis.* 7:458–467 (1985), Kasper, D. L. et al., *J. Infec. Dis.* 153:407415 (1986), which references are incorporated herein by reference).

In a conjugate vaccine, an antigenic molecule, such as the capsular polysaccharides of group B Streptococcus (discussed above), is covalently linked to a "carrier" protein or polypeptide. The linkage serves to increase the antigenicity of the conjugated molecule. Methods for forming conjugate vaccines from an antigenic molecule and a "carrier" protein or polypeptide are known in the art (Jacob, C. O, et al., *Eur. J. Immunol.* 16:1057–1062 (1986); Parker J. M. R. et al., In: *Modern Approaches to Vaccines*, Chanock, R. M. et al., eds, pp. 133–138, Cold Spring Harbor Laboratory, Cold Spring Harbor, N.Y. (1983); Zurawski, V. R, et al., *J. Immunol.* 121:122–129 (1978); Klipstein, F. A, et al., *Infect. Immun.* 37:550–557 (1982); Bessler, W. G, Immunobiol. 170:239–244 (1985); Posnett, D. N, et al., *J. Biol. Chem.* 263:1719–1725 (1988); Ghose, A. C, et al., *Molec. Immunol.* 25:223–230 (1988); all of which references are incorporated herein by reference).

A prototype model for conjugate vaccines was developed against Hemophilus influenzae (Anderson, P, *Infec. and Immun.* 39:223–238 (1983); Chu, C, et al., *Infect. Immun.* 40:245–256 (1983); Lepow, M, Pediat. *Infect. Dis. J.* 6:804–807 (1987), which references are incorporated herein by reference), and this model may be employed in constructing the novel vaccines of the present invention. Additional methods for producing such a conjugate vaccine are disclosed by Anderson, P. W, et al., European Patent Publication 245,045; Anderson, P. W, et al., U.S. Pat. Nos. 4,673,574 and 4,761,283; Frank, R. et al., U.S. Pat. No. 4,789,735; European Patent Publication No. 206,852; Gordon, L. K, U.S. Pat. No. 4,619,828; and Beachey, E. H, U.S. Pat. No. 4,284,537, all of which references are incorporated herein by reference.

The protein backbones for conjugate vaccines such as the Hemophilus influenzae vaccine have utilized proteins that do not share antigenic properties with the target organism from which the bacterial capsular polysaccharides were obtained (Ward, J. et al., In: *Vaccines*, Plotkin, S. A, et al., eds, Saunders, Philadelphia, page 300 (1988).

In contrast, the conjugate vaccine of the present invention employs immunogenic proteins of group B Streptococcus as the backbone for a conjugate vaccine. Such an approach is believed to lead to more effective vaccines (Insel, R. A, et al., *New Eng. J. Med.* (Editorial) 319(18):1219–1220 (1988)). The conjugate, protein-polysaccharide vaccine of the present invention is the first to specifically characterize group B Streptococcus proteins that may be used in a conjugate vaccine. Any protein which is characteristic of group B Streptococcus may be employed as the protein in the conjugate vaccines of the present invention. It is, however, preferred to employ a C protein of a group B Streptococcus for this purpose. As discussed more fully below, plasmids pJMS1 and pJMS23 contain DNA which encode Streptococcus C protein. The most preferred C proteins are those obtained upon the expression of such DNA in bacteria.

As indicated above, the present invention concerns the cloning and expression of genes which encode the protective group B Streptococcus protein antigens. Such proteins are preferably used as the protein backbone to which the one or more of the polysaccharides of the group B Streptococcus can be conjugated in order to form a conjugate vaccine against these bacteria. Alternatively, one or more proteins as described herein may be conjugated to the structure of a polysaccharide of the group B Streptococcus.

The role of these proteins in the virulence and immunity of group B Streptococcus may be exploited to develop an additional therapy against group B Streptococcus infection. The isolation and characterization of these genes of a bacterial origin allows the manipulation of the gene products to optimize both the adjuvant and antigenic properties of the polypeptide backbone/carrier of the conjugate vaccine.

Genetic Studies of the C Proteins

The present invention thus concerns the cloning of the C proteins of group B Streptococcus, their role in virulence and immunity, and their ability to serve as an immunogen for a conjugate vaccine against group B Streptococcus.

Despite the extensive literature available on cloning in many groups of Streptococci, only limited genetic manipulations have been accomplished in group B Streptococcus (Macrina, F. L, *Ann. Rev. Microbiol.* 38:193–219 (1984), Wanger, A. R, et al., *Infec. and Immun.* 55:1170–1175 (1987)). The most widely used technique in group B Streptococcus has been the development of Tn916 and its use in transposon mutagenesis (Rubens, C. E, et al., *Proc. Natl. Acad. Sci. USA* 84:7208–7212 (1987), Wanger, A. R, et al., *Res. Vet. Sci.* 38:202–208 (1985)). However, since it would appear that there is more than one gene for the C proteins and the protective antisera bind to several proteins, screening for the C protein genes by transposon mutagenesis is impractical.

The present invention accomplishes the cloning of the C proteins (and of any other proteins which are involved in the virulence of the group B Streptococcus, or which affect host immunity to the group B Streptococcus) through the use of a novel plasmid vector. For this purpose, it is desirable to employ a cloning vector that could be rapidly screened for expression of proteins which bind to naturally elicited antibodies to group B Streptococcus. Since such antibodies are heterologous polyclonal antibodies and not monoclonal antibodies, it was necessary that a vector be employed which could be easily screened through many positive clones to identify genes of interest.

A number of techniques were available for screening clones for the expression of antigens that bind to a specific antisera (Aruffo, A, et al., *Proc. Natl. Acad. Sci. USA* 84:8573–8577 (1987)). The most widely used system, λgt11, was developed by Young and Davis (Huynh, T. V. et al., In: *DNA Cloning, A Practical Approach*, Vol. 1 (Glover, D. M, Ed.) IRL Press, Washington pp. 49–78 (1985); Wong, W. W, et al., *J. Immunol. Methods.* 82:303–313 (1985), which references are incorporated herein by reference). This technique allows for the rapid screening of clones expressed in the lysogenic phage whose products are released by phage lysis. Commonly faced problems with this system include the requirement for subcloning DNA fragments into plasmid vectors for detailed endonuclease restriction mapping, preparing probes and DNA sequencing. In addition, the preparation of DNA from phage stocks is cumbersome and limits the number of potentially positive clones that can be studied efficiently. Finally, the preparation of crude protein extracts from cloned genes is problematic in phage vector hosts.

To circumvent these problems, the present invention provides a plasmid vector which was developed for screening cloned bacterial chromosomal DNA for the expression of proteins involved in virulence and/or immunity. The present invention thus further concerns the development and use of an efficient cloning vector that can be rapidly screened for expression of proteins which bind to naturally elicited antibodies to group B Streptococcus. The vector was prepared by modifying the commonly used plasmid cloning vector, pUC12 (Messing, J, et al., *Gene* 19:269–276 (1982); Norrander, J, et al., *Gene* 26: 101–106 (1983); Vieira, J, et al., *Gene* 19:259–268 (1982); which references are incorporated herein by reference). The invention concerns the vector described below, and its functional equivalents.

Using this system, plasmid clones can be easily manipulated, mapped with restriction endonucleases and their DNA inserts sequences, probes prepared and gene products studied without the necessity for subcloning. pUC12 is a 2.73 kilobase (kb) high copy number plasmid that carries a ColE1 origin of replication, ampicillin resistance and a polylinker in the lacZ gene (Ausubel, F. M, et al., *Current Topics in Molecular Biology; Greene Publ. Assn./ Wiley Interscience, NY* (1987) which reference is incorporated herein by reference).

Several modifications were made in the polylinker of pUC12 (Aruffo, A, et al., *Proc. Natl. Acad. Sci. USA* 84:8573–8577 (1987) which reference is incorporated herein by reference). The overall plan in altering pUC12 was to modify the polylinker to present identical but non-cohesive BstXI sites for cloning, to add a "stuffer" fragment to allow for easy separation of the linear host plasmid, and to provide for expression from the lac promoter in all three translational reading frames.

In order to provide a site for the insertion of foreign DNA with a high efficiency and to minimize the possibility for self-ligation of the plasmid, inverted, non-cohesive BstXI ends were added to the polylinker. As shown in FIG. 1, pUC12 was first cut with BamHI (Step 1) and the plasmid was mixed with two synthetic oligonucleotide adaptors that are partially complementary: a 15-mer (GATCCATTGTGCTGG) [SEQ ID NO: 3] and an 11-mer (GTAACACGACC) [SEQ ID NO: 4] (Step 2). When the adaptors are ligated into pUC12, two new BstI sites are created but the original BamHI sites are also restored (Step 3). The plasmid was then treated with polynucleotide kinase and ligated to form a closed circular plasmid (Step 4). When this plasmid is treated with BstXI, the resulting ends are identical and not cohesive (both have GTGT overhangs) (Step 5).

Figure 2:
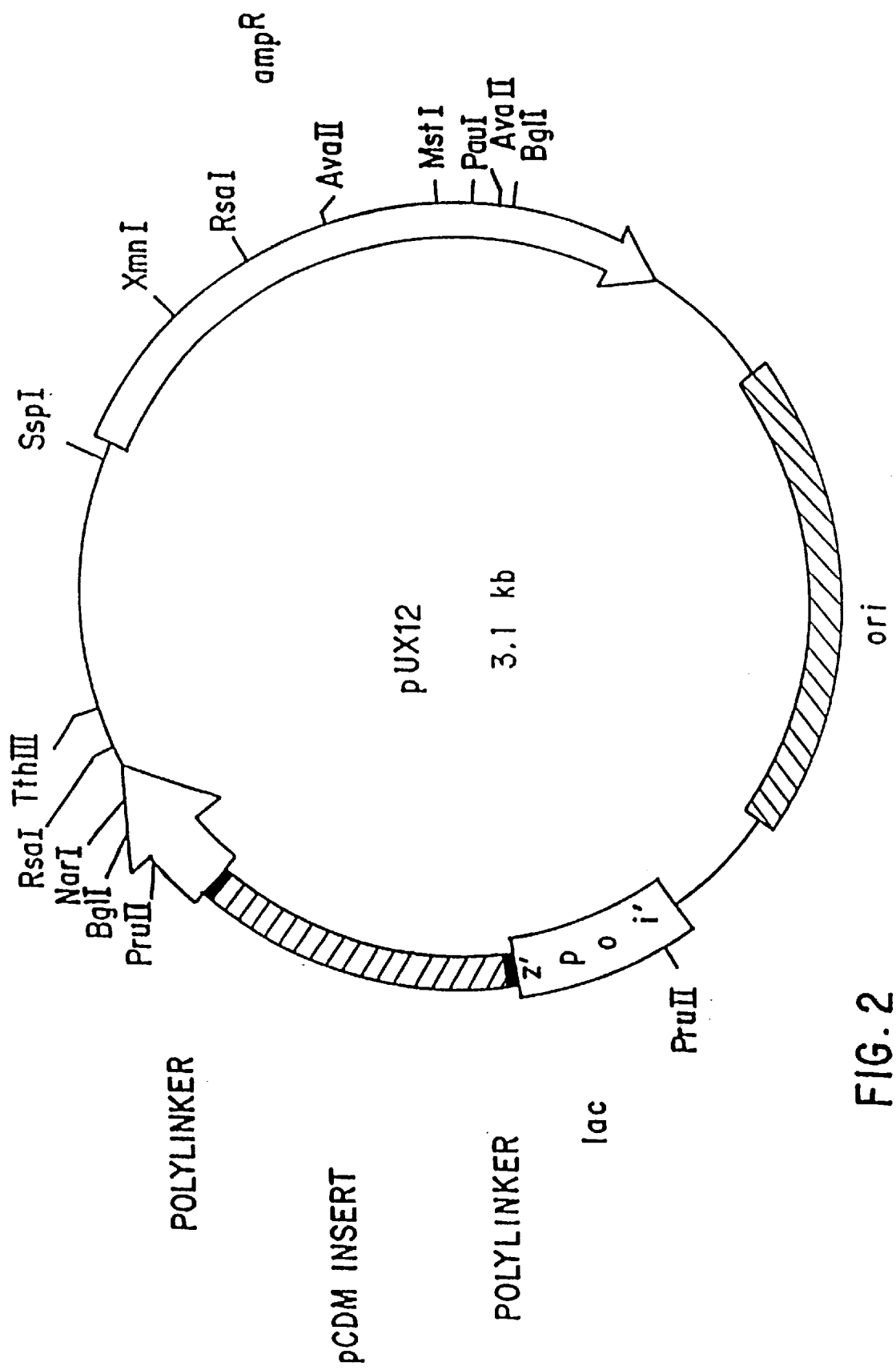
FIG. 2 shows the restriction and transcriptional map of the plasmid pUX12.

A second modification in the polylinker was done to allow for the purification of the linear plasmid for cloning without contamination from partially cut plasmid that can self-ligate. A blunt end, 365 base pair (bp), FnuD2 fragment was obtained from the plasmid pCDM. This cassette or "stuffer" fragment, which does not contain a BstXI site, was blunt end ligated to two synthetic oligonucleotides that are partially complementary: a 12-mer (ACACGAGATTTC) [SEQ ID NO: 5] and an 8-mer (CTCTAAAG) (Step 6). The resulting fragment with adaptors has 4 bp overhangs (ACAC) that are complementary to the ends of the modified pUC12 plasmid shown in Step 5. The modified pUC12 plasmid was ligated to the pCDM insert with adaptors; the resulting construct, named pUX12, is shown in FIG. 2. The pUX12 plasmid can be recreated from plasmids pJMS1 or pJMS23 by excision of the introduced Streptococcus DNA sequences. Alternatively, it may be formed by recombinant methods (or by homologous recombination), using plasmid pUC12.

Since pUX12 is to be used as an expression vector, it is preferable to further modified the polylinker such that it will contain all three potential reading frames for the lac promoter. These changes allow for the correct translational reading frame for cloned gene fragments with a frequency of one in six. For example, a cloned fragment can insert in the vector in one of two orientations and one of three reading frames. To construct a +1 reading frame, the pUX12 plasmid was cut with the restriction enzyme EcoRI which cleaves at a unique site in the polylinker. The single stranded 5' sticky ends were filled in using the 5'-3' polymerase activity of T4 DNA polymerase, and the two blunt ends ligated. This resulted in the loss of the EcoRI site, and the creation of a new XmnI site (FIG. 3A). This construction was confirmed by demonstrating the loss of the EcoRI site and confirming the presence of a new XmnI site in the polylinker. In addition, double stranded DNA sequencing on the +1 modified pUX12 plasmid was performed using standard sequencing primers (Ausubel, F. M, et al., *Current Topics in Molecular Biology*; Greene Publ. Assn./ Wiley Interscience, NY (1987)). The DNA sequence showed the addition of 4 base pairs to the polylinker and confirmed the modification of pUX12 to a +1 reading frame. This plasmid is called pUX12+1.

In order to construct a −1 reading frame, the pUX12 vector was cut with the restriction enzyme SacI which cuts at a unique site in the polylinker of pUX12. The single stranded 3' sticky ends were cut back to blunt ends using the 3'-5' exonuclease activity of T4 polymerase, and the resulting blunt ends ligated. The resulting sequence should eliminate the SacI site while resulting in a new FnuD2 site (FIG. 3B). However, restriction mapping of the pUX12-1 plasmids showed that while the SacI site was absent, there was no FnuD2 site present. In addition, the SmaI/XmaI sites on the polylinker were no longer present. Several potential pUX12-1 constructs were sequenced from mini-prep, double-stranded DNA. Of the six modified plasmids sequenced, one was found with ten nucleotides absent, thereby creating a −1 reading frame (FIG. 3C). This suggests that the T4 DNA polymerase has additional exonuclease activity and cuts back additional double stranded portions of the polylinker. Nevertheless, the resulting plasmid had a −1 reading frame. The plasmid was named pUX12-1.

The use of the pUX12 vectors in the cloning of antigenic proteins of group B Streptococcus are discussed in detail in the Examples below. In brief, DNA derived from group B Streptococcus, or complementary to such DNA is introduced into the pUX12, pUX12+1 or pUX12-1 vectors and transformed into *Eschelichia coli*. The cloned DNA is expressed in *E. coli* and the cellular lysate is tested to determine whether it contains any protein capable of binding to antisera to group B Streptococcits.

There are a number of potentially interesting modifications of pUX12 that could increase its utility. For example, the lac promoter could be replaced by another promoter, the origin of replication could be modified to produce a lower copy number vector and the drug resistance marker could be changed.

Any vector capable of providing the desired genetic information to the desired host cell may be used to provide genetic sequences encoding the alpha antigen derivatives of the invention to a host cell. For example, in addition to plasmids, such vectors include linear DNA, cosmids, transposons, and phage.

The host cell is not limited to *E. coli*. Any bacterial or yeast (such as *S. cerewsiae*) host that is capable of expressing the derivatives of the invention may be used as an appropriate host. For example, *B. subtilis* and the group B Streptococcus may be used as hosts. Methods for cloning and into such hosts are known. For example, for Gram-positive hosts, see Harwood, C. R., et al., eds., "*Molecular Biological Methods for Bacillus,*" Wiley-Interscience, New York, 1991) for a description of culture methods, genetic analysis plasmids, gene cloning techniques, the use of transposons, phage, and integrational vectors for mutagenesis and the construction of gene fusions, and methods of measuring gene expression. Appropriate hosts are available from stock centers such as the American Type Culture Collection (Rockville, Md., USA) and the Bacillus Genetic Stock Center (Ohio State Univ., Columbus, Ohio, USA).

The present invention concerns a vaccine comprising a polysaccharide (such as the capsular polysaccharide) which is characteristic of the group B Streptococcus conjugated to a protein which is also characteristic of the group B Streptococcus. The "polysaccharide" and "protein" of such a conjugated vaccine mnay be identical to a molecule which is characteristic of the group B Streptococcus, or they may be functional derivatives of such molecules.

For the purposes of the present invention, a group B Streptococcus polysaccharide is any group B-specific or type-specific polysaccharide. Preferably, such polysaccharide is one which, when introduced into a mammal (either animal or human) elicits antibodies which are capable of reacting with group B Streptococcus may be employed. Examples of the preferred polysaccharides of the present invention include the capsular polysaccharide of the group B Streptococcus, or their equivalents. For the purposes of the present invention, any protein which when introduced into a mammal (either animal or human) either elicits antibodies which are capable of reacting a protein expressed by group B Streptococcus, or which increases the immunogenicity of a polysaccharide to elicit antibodies to a polysaccharide of the group B Streptococcus may be employed. Examples of the preferred proteins of the present invention include the C proteins of the group B Streptococcus, or their equivalents.

Examples of functional derivatives of the peptide antigens include fragments of a natural protein, such as N-terminal fragment, C-terminal fragment or internal sequence fragments of the group B Streptococcus C protein alpha antigen that retain their ability to elicit protective antibodies against the group B Streptococcus. The term functional derivatives is also intended to include variants of a natural protein (such as proteins having changes in amino acid sequence but which retain the ability to elicit an immunogenic, virulence or antigenic property as exhibited by the natural molecule), for example, the variants of the alpha antigen recited below that possess fewer of the internal repeats than does the native alpha antigen, and/or an altered flanking sequence.

The peptide antigen that is conjugated to the polysaccharide in the vaccine of the invention may be a peptide encoding the native amino acid sequence of the alpha antigen, as encoded on plasmid pJMS23 (with or without the signal peptide sequence) or it may be a functional derivative of the native sequence. The native group B Streptococcus C protein alpha antigen as encoded on pJMS23 contains an open reading frame of 3060 nucleotides and encodes a precursor protein of 108,705 daltons. Cleavage of the putative signal sequence of 41 amino acids yields a mature protein of 104,106 daltons. The 20,417 dalton N-terminal region of the alpha antigen shows no homology to previously described protein sequences and is followed by a series of nine tandem repeating units that make up 74% of the mature protein. Each repeating unit (denoted herein as "R") is identical and consists of 82 amino acids with a molecular mass of 8665 daltons, which is encoded by 246 nucleotides. The size of the repeating units corresponds to the observed size differences in the heterogeneous ladder of alpha C proteins naturally expressed by the group B Streptococcus. The C-terminal region of the alpha antigen contains a membrane anchor domain motif that is shared by a number of Gram-positive surface proteins. The large region of identical repeating units in this gene, (termed the bca gene, for group B Streptococcus, C protein, alpha antigen) defines protective epitopes and may be used to generate diversity of alpha antigen functional derivatives that are useful in the vaccines of the invention.

Preferably, the sequence of such a functional alpha antigen derivative contains 1–9 copies of the 82 amino acid repeat (246 nucleotides) that begin at amino acid 227 of the DNA sequence of FIG. 6A–6C, (as used herein, the partial repeat designed as repeat 9' therein is also useful in this regard). The functional derivative may lack the 185 amino acid 5' flanking sequence (555 nucleotides) that is found in the native protein prior to the repeating sequence or it may retain this sequence and/or the derivative may lack the 45 amino acid (246 nucleotides) C-terminal anchor sequence or it may retain this sequence. The functional derivative may be the N-terminal fragment that precedes the start of the alpha antigen repeating unit(s) or the functional derivative may be only the C-terminal fragment that follows the end of the alpha antigen repeating unit(s) or the function derivative may be a hybrid of the N-terminal fragment and C-terminal fragment with no copies of the "R" units as defined below. The amino terminal sequence of the native alpha antigen may or may not contain the signal sequence. Either of the alpha antigen's amino terminal sequence or carboxy terminal sequence may be used in the conjugate vaccines of the invention, with or without one or more copies of the sequence that is repeated in the core of the native alpha antigen protein.

As used herein, "R" represents one copy of the 82 amino acid repeat that beings at amino acid 227 of the alpha antigen DNA sequence of FIG. 6A–6C, "$R_x$" represents "X" number of tandem copies of this repeat, tandemly joined at the carboxyl end of one R unit to the amino terminal end of the adjoining R unit, "N" represents the 5' amino acid flanking sequence that is found in the sequence shown on FIG. 6A–6C, with or without the signal sequence; when the signal sequence is lacking, "N" is a 185 amino acid 5' flanking sequence that is found in the native protein as shown on FIG. 6A–6C; when the signal sequence is present, "N" is a 226 amino acid 5' flanking sequence as shown in FIG. 6A–6C. "C" represents the 45 amino acid C-terminal anchor sequence as shown on FIG. 6. Using this notation, the following species are examples of derivatives of the native protein that may be constructed according to the invention:

1. $R_1$
2. N
3. C
4. N—C
5. N—$R_1$
6. R—C
7. N—$R_1$—C
8. $R_2$
9. N—$R_2$
10. $R_2$—C
11. N—$R_2$—C
12. $R_3$

13. N—$R_3$
14. $R_3$—C
15. N—$R_3$—C
16. $R_4$
17. N—$R_4$
18. $R_4$—C
19. N—$R_4$—C
20. $R_5$
21. N—$R_5$
22. $R_5$—C
23. N—$R_5$—C
24. $R_6$
25. N—$R_6$
26. $R_6$—C
27. N—$R_6$—C
28. $R_7$
29. N—$R_7$
30. $R_7$—C
31. N—$R_7$—C
32. $R_8$
33. N—$R_8$
34. $R_8$—C
35. N—$R_8$—C
36. $R_9$
37. N—$R_9$
38. $R_9$—C
39. N—$R_9$—C
40. $R_{10}$
41. N—$R_{10}$
42. $R_{10}$—C
43. N—$R_{10}$—C.

Greater than 10 repeating R units, including, for example, 11, 12, 13, 14, 15, 16, 17, 18, 19 or 20 R units, may be constructed in a similar manner. In addition, fragments of R, N, or C may be used if such fragments enhance the functional ability of the derivative to elicit protective antibodies against the group B Streptococcus, or if such fragment provides another desired property to the construct, such as a secretion signal or membrane localization signal.

Alpha antigens from other strains of the group B Streptococcus may be prepared and used in a similar manner as a slight variability in the sequence of the protein, such as in the N terminus or C terminus or R repeat would not alter the biological properties and their functional ability to elicit protective antibodies. For example, a group B Streptococcus alpha antigen isolated from a different strain of the group B Streptococcus and having the same repeat unit but a different N-terminal amino acid sequence is intended to be within the scope of the invention.

The peptides of the invention, whether encoding a native protein or a functional derivative thereof, are conjugated to a group B Streptococcus carbohydrate moiety by any means that retains the ability of these proteins to induce protective antibodies against the group B Streptococcus.

Heterogeneity in the vaccine may be provided by mixing specific conjugated species. For example, the vaccine preparation may contain one or more copies of one of the peptide forms conjugated to the carbohydrate, or the vaccine preparation may be prepared to contain more than one form of the above functional derivatives and/or the native sequence, each conjugated to a polysaccharide used therein. Conjugates providing a peptide (such as one of the peptides exemplified in group numbers 1–43) can be mixed with conjugates providing any other peptide (such as a second example from group numbers 1–43) to arrive at a "compound" conjugate vaccine. A multivalent vaccine may also be prepared by mixing the group B-specific conjugates as prepared above with other proteins, such as diphtheria toxin or tetanus toxin, and/or other polysaccharides, using techniques known in the art.

Heterogeneity in the vaccine may also be provided by utilizing group B Streptococcal preparations from group B Streptococcal hosts (especially into *Streptococcus agalactine*), that have been transformed with the recombinant constructs of the invention such that the streptococcal host expresses the alpha antigen protein or functional derivative thereof. In such cases, homologous recombination between the genetic sequences encoding the repeating R units will result in spontaneous mutation of the host, such that a population of hosts is easily generated and such hosts express a wide range of antigenic alpha antigen functional derivatives useful in the vaccines of the invention. Such spontaneous mutation usually results in the deletion of R units, or portions thereof, although mutation of other regions of the alpha antigen may also occur.

As used herein, a polysaccharide or protein is "characteristic" of a bacteria if it is substantially similar in structure or sequence to a molecule naturally associated with the bacteria. The term is intended to include both molecules which are specific to the organism, as well as molecules which, though present on other organisms, are involved in the virulence or antigenicity of the bacteria in a human or animal host.

The vaccine of the present invention may confer resistance to group B Streptococcus by either passive immunization or active immunization. In one embodiment of passive immunization, the vaccine is provided to a host (i.e. a human or mammal) volunteer, and the elicited antisera is recovered and directly provided to a recipient suspected of having an infection caused by a group B Streptococcus.

The ability to label antibodies, or fragments of antibodies, with toxin labels provides an additional method for treating group B Streptococcus infections when this type of passive immunization is conducted. In this embodiment, antibodies, or fragments of antibodies which are capable of recognizing the group B Streptococcus antigens are labeled with toxin molecules prior to their administration to the patient. When such a toxin derivatized molecule binds to a group B Streptococcus cell, the toxin moiety will cause the death of the cell.

In a second embodiment, the vaccine is provided to a female (at or prior to pregnancy or parturition), under conditions of time and amount sufficient to cause the production of antisera which serve to protect both the female and the fetus or newborn (via passive incorporation of the antibodies across the placenta).

The present invention thus concerns and provides a means for preventing or attenuating infection by group B Streptococcus, or by organisms which have antigens that can be recognized and bound by antisera to the polysaccharide and/or protein of the conjugated vaccine. As used herein, a vaccine is said to prevent or attenuate a disease if its administration to an individual results either in the total or partial attenuation (i.e. suppression) of a symptom or condition of the disease, or in the total or partial immunity of the individual to the disease.

The administration of the vaccine (or the antisera which it elicits) may be for either a "prophylactic" or "therapeutic"

purpose. When provided prophylactically, the compound(s) are provided in advance of any symptom of group B Streptococcus infection. The prophylactic administration of the compound(s) serves to prevent or attenuate any subsequent infection. When provided therapeutically, the compound(s) is provided upon the detection of a symptom of actual infection. The therapeutic administration of the compound(s) serves to attenuate any actual infection.

The protective-antibody-eliciting agents of the present invention may, thus, be provided either prior to the onset of infection (so as to prevent or attenuate an anticipated infection) or after the initiation of an actual infection.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

As would be understood by one of ordinary skill in the art, when the vaccine of the present invention is provided to an individual, it may be in a composition which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from Mycobacterium tuberculosis, as well as substances found in *Corynebactenium parvum*, or *Bordetella pertussis*, and members of the genus Brucella. Among those substances particularly useful as adjuvants are the saponins such as, for example, Quil A. (Superfos A/S, Denmark). Examples of materials suitable for use in vaccine compositions are provided in *Remington's Pharmaceutical Sciences* (Osol, A, Ed, Mack Publishing Co, Easton, Pa., pp. 1324–1341 (1980), which reference is incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

Having now generally described the invention, the same will be more readily understood through reference to the following examples which are provided by way of illustration, and are not intended to be limiting of the present invention, unless specified.

EXAMPLE 1

Cloning Efficiency of the pUX12 Vectors

Several experiments were designed to test the cloning efficiency of the pUX12 vectors and to determine whether the modified reading frames transcribed correctly. The results of these experiments will be briefly summarized below:

1. To clone a DNA fragment into pUX12, the three constructs, pUX12 (the original "zero" reading frame construction), pUX12+1 and pUX12−1, were mixed in equimolar concentrations. The plasmids were then cut with BstXI to cleave the stuffer fragment within the polylinker. The stuffer fragment was separated from the plasmid using either low melting point agarose or a potassium acetate gradient (Aruffo, A, et al., *Proc. Natl. Acad. Sci. USA* 84:8573–8577 (1987), Ausubel, F. M, et al., *Current Topics in Molecular Biology*; Greene Publ. Assn./ Wiley Interscience, NY (1987)). The DNA to be cloned was cut with a restriction enzyme that gives blunt ends (any such restriction enzyme may be employed). If necessary, double stranded DNA with signal stranded ends can be modified to create blunt ends. The blunt ends of the DNA fragments were mixed with the two synthetic oligonucleotide adaptors. These are the same 12-mer and 8-mer used in preparing the stuffer fragment. The modified DNA fragments were separated from the unincorporated synthetic oligonucleotides on a potassium acetate gradient. These fragments were then ligated into the linear pUX12 family of plasmids and used to transform *E. coli*.

To verify that the pUX12 vectors self-ligate at a low frequency under conditions optimize for the cloning of inserts with adaptors, a second drug resistance marker was cloned into pUX12. As shown in FIG. 1, pUX12 has a β-lactamase gene and carriers resistance to ampicillin ($amp^R$). The rationale for cloning a second marker was to compare the ratio of clones that contained both drug resistance markers to those pUX12 plasmids that self-ligated under typical cloning conditions and therefore only expressed resistance to ampicillin. The tetracycline resistance gene ($tet^R$) from the plasmid pBR322 was cloned into the polylinker of pUX12 with the adaptors described above. A group of test ligations were run to establish the optimal concentration of oligonucleotide adaptor to fragment ends, and the ratio of modified insert to linear pUX12 plasmid for ligation and transformation. By using the tet$^R$ gene as a marker, we were able to determine cloning parameters so that greater than 99% of the transformants selected on ampicillin containing plates also carried the tet$^R$ marker. Thus, the frequency of self-ligation is very low in this system and it is not necessary to screen for the presence of an insert in the polylinker prior to screening a library in pUX12.

2. To confirm the position of the translational reading frame in the polylinker of pUX12, a structural gene whose sequence and product are known, and that lacks its own promoter, was cloned.

For this purpose, a mutant of the tox structural gene carried on the plasmid (Costa, J. J, et al., *J. Bacteriol.* 148(1):124–130 (1981), Michel, J. L, et al., *J. virol.* 42:510–518 (1982) which references are incorporated herein by reference) was chosen. The plasmid, pABC402, was treated simultaneously with the restriction endonucleases ApaI and HindIII (Bishai, W. R, et al., *J. Bacteriol.* 169:1554–1563 (1987), Bishai, W. R., et al., *J. Bacteriol.* 169:5140–5151 (1987) which references are incorporated herein by reference). The ApaI site is within the structural gene near the N-terminal and the HindIII site lies just outside of the C-terminal of the tox gene. This 1.2 kb restriction fragment was separated from the remaining 4.1 kb of the pABC402 vector using low melting point agarose.

To create blunt ends for cloning, the tox fragment was treated with T4 DNA polymerase. The exonuclease activity of the polymerase cut back the ApaI 3' ends and the polymerase activity filled in the 5' overhand at the HindIII site (Maniatis, T. et al., *Molecular Cloning*, A Laboratory Manual, Cold Spring Harbor Press, Cold Spring Harbor, N.Y. (1982)). This purified fragment with blunt ends was ligated into the mixture of pUX12 that contains all three reading frames. Individual transformants were randomly picked and screened by restriction mapping to determine the orientation and reading frame of the inserts. In addition, the nucleotide sequences of the polylinker/adaptor/insert regions were determined. All six potential orientation and reading frame combinations were identified. Finally, extracts from these clones were screened using Western blots probed with antisera to diphtheria toxin (Blake, M. S., et al., *Anal. Biochem.* 136:175–179 (1984), Murphy, J. R., et al., *Curr. Topics Microbiol. and Immun.* 118:235–251 (1985)).

Reactive toxin related proteins were only detected from clones that contained the structural gene in the correct orientation and reading frame. This plasmid is called pUDTAH-1; the DNA sequence of the polylinker and beginning of the tox structural gene is shown in Table 1. The depicted sequence is the DNA sequence of the beginning of the tox' structural gene in pUDTAH-1. ATG is the start signal for the transcript (lacZ'), GAT begins the modified polylinker of pUX12 and GCC starts the correct translational reading frame for the tox' gene.

TABLE 1

| SEQUENCES OF PLASMID pUDTAH | | | |
|---|---|---|---|
| ATGACCATGATTACGAATTCGAGCTCGCCCGGG | GATCCATTGTGCTGGAAAG | CCACC | [SEQ ID NO: 6] |
| POLYLINKER (ATG = LacZ Translation Initiation Codon) | OLIGONUCLEOTIDE ADAPTORS | DIPHTHERIA TOX' GENE | |

EXAMPLE 2

Purification of Chromosomal DNA from Group B Streptococcus

To accomplish the purification of chromosomal DNA from group B Streptococcus chromosomal DNA was isolated from the A909 strain of group B Streptococcus (Lancefield, R. C., et al., *J. Exp. Med.* 142:165–179 (1975)) by the method of Hull et al., (Hull, R. A., et al., *Infect. and Immun.* 33:933–938 (1981)) as modified by Rubens et al., (Rubens, C. E., et al., *Proc. Natl. Acad. Sci USA* 84:7208–7212 (1987) both of which references are incorporated herein by reference). In brief, mutanolysin was used to convert the group B Streptococcus strain A909 (Ia/c) strain into protoplasts. The resulting surface extract was found to contain numerous proteins that immunoreact with protective antisera raised to the intact bacteria. An insoluble protein fraction was partially purified using conventional column chromatography. Two fractions, including one which was highly concentrated for a single 14 kilodalton (kd) species, were used to immunize rabbits. Antisera raised against these partially purified group B Streptococcus proteins were found to be able to confer passive protection in a mouse virulence assay against a heterologous capsule type of group B Streptococcus which carries the C proteins.

Group B Streptococcus DNA was purified by centrifugation in a buoyant-density cesium chloride (CsCl) gradient, and the chromosomal DNA was dialyzed exhaustively against TAE buffer, pH 8.0 (Maniatis, T. et al., *Molecular Cloning, A Laboratory Manual*, Cold Spring Harbor Press, Cold Spring Harbor, N.Y. (1982). The A909 strain of group B Streptococcus has a type 1 capsule, expresses the C proteins and has been used previously in studies of the C proteins (Valtonen, M. V., et al., *Microb. Path.* 1:191–204 (1986)). It is also the strain of group B Streptococcus that was used in preparing the protective antisera for screening.

The yield of Group B Streptococcus chromosomal DNA averages 3 to 5 mg for each 500 ml of an overnight culture of group B Streptococcus. The purified DNA was digested separately with 24 commonly used restriction endonucleases and the resulting fragments were run on a 1.0% agarose gel. A wide range of enzymes were chosen, including those that have unique sites on the polylinkers commonly used in cloning vectors. Ethidium bromide (EtBr) staining of the gel showed that all of the restriction enzymes yielded a distribution of discrete fragment sizes of group B Streptococcus DNA. This suggests that group B Streptococcus DNA is not modified for any of the restriction enzymes tested.

In order to determine whether there were any inhibitors present to block ligation of the DNA, the restriction endonuclease digestions described above were ethanol precipitated, placed in a ligation buffer and incubated overnight at 14° C. with DNA ligase. These samples were again run on a 1.0% agarose gel and stained with EtBr. The resulting restriction patterns showed a higher molecular weight distribution. Therefore, there was no inhibition of the ligation of group B Streptococcus DNA.

EXAMPLE 3

Preparation of a Library of Group B Streptococcus Chromosomal DNA

The preparation of a library of group B Streptococcus chromosomal DNA in pUX12 and its transformation into *E. coli* was performed as follows. To cleave the group B Streptococcus chromosomal DNA for cloning, four restriction enzymes were chosen that give a broad distribution of restriction fragment sizes. The pUX12 vector and adaptors are most efficient when blunt ended fragments are cloned. The enzymes chosen recognize four base pair sites and leave blunt ends. Group B Streptococcus DNA was partially digested individually with AluI, FunD2, HaeIII and RsaI.

The resulting fragments were mixed, purified with phenol/chloroform, ethanol precipitated and resuspended in a ligation buffer (Maniatis, T. et al., *Molecular Cloning, A Laboratory Manual*, Cold Spring Harbor Press, Cold Spring Harbor, N.Y. (1982)). One μg of the group B Streptococcus DNA fragments was mixed with 3 μg of the 12-mer and 2 μg of the 8-mer oligonucleotide adaptors. Three microliters of T4 DNA ligase (600 units, New England Biolabs), were added and the reaction was maintained overnight at 14° C. The free linkers were separated from the group B Streptococcus DNA fragments on a potassium acetate velocity gradient (Aruffo, A., et al., *Proc. Natl. Acad. Sci. USA* 84:8573–8577 (1987)).

The pUX12 plasmid containing all three translational reading frames was digested with BstXI and the stuffer fragment was removed using a low melting point agarose gel. The group B Streptococcus library was prepared by mixing 10 ng of the adapted group B Streptococcus fragments with 100 ng of the linear pUX12 vector in 100 μl of ligation buffer to which 0.1% T4 DNA ligase was added. The ligation reaction was maintained overnight at 14° C. and then used to transform the MC1061 strain of *E. coli* on plates containing ampicillin (Ausubel, F. M., et al., *Current Topics in Molecular Biology* (1987)).

Sixteen of the resulting transformants were isolated, grown overnight in LB and plasmid DNA isolated by mini-preps. The plasmid DNA was digested with BamHI, and run on a 1.0% agarose gel. All of the plasmids screened contained inserts in the pUX12 vector, and the average insert size was 1.4 kb. To date, the plasmid DNA obtained from over 200 clones have been screened and only one clone was found that appeared to lack an insert in the polylinker.

EXAMPLE 4

Characterization of Protective Antisera to be Used in Screening the Library

As discussed earlier, the C proteins have been partially purified by a variety of techniques and protective antisera have been prepared by a number of investigators (Bevanger, L., et al., *Acta Path. Microbiol. Scand. Sect. B.* 93:113–119 (1985), Russell-Jones, G. J., et al., *J. Exp. Med.* 160:1476–1484 (1984), Wilkinson, H. W., et al., *Infec. and Immun.* 4:596–604 (1971)).

A set of experiments was performed to duplicate the work of Valtonen, Kasper and Levy who isolated a 14,000 mw protein from supernatants of group B Streptococcus that elicits protective antibody (Valatonen, M. V., et al., *Microb. Path.* 1:191–204 (1982) which reference is incorporated herein by reference). This experiment revealed that when proteolytic inhibitors to the supernatants of group B Streptococcus cultures are added prior to the concentration and purification of the C proteins (Wong, W. W., et al., *J. Immunol. Methods.* 82:303–313 (1985)), the 14,000 mw protein was no longer a prominent protein in the supernatant; This indicated that this protein results from the proteolysis of larger molecular weight C proteins in the supernatants of group B Streptococcus cultures.

EXAMPLE 5

Optimizin Conditions for Screening for Expression in a Plasmid-Based Vector

As discussed above, the most commonly used vectors for the detection of expression are based on λgt11 (Young, R. A., et al., *Proc. Natl. Acad. Sci. USA* 80:1194–1198 (1983)). We were able to increase the sensitivity of detection of expression from the pUX12 plasmid vector by combining two previously described procedures for antibody screening of bacterial colonies. The transformants from the library were plated overnight and the resulting colonies transferred to nitrocellulose filters (Bio-Rad). The colonies were lysed by placing the filters in an atmosphere saturated with chloroform ($CHCl_3$) in a closed container for 30 minutes. The filters were then placed in a lysis buffer and incubated overnight as described by Helfman etal. (Helfman, D. M., etal., *Proc. Natl. Acad. USA* 80:31–35 (1983)). The antibody screening was done utilizing commercially prepared *E. coli* lysate (ratio 1:200) and Horseradish Peroxidase Conjugated, Affinity Purified Goat Anti-Rabbit IgG (ratio 1:3000) in the Express-Blot Assay Kit prepared by Bio-Rad Laboratories. By pretreating the colonies with chloroform and the overnight incubation with DNase and lysozyme described above, it was possible to reduce the ratio of primary antibody required from 1:500 to 1:5000.

EXAMPLE 6

Initial Analysis of Positive Clones and their Protein Products

The library of group B Streptococcus chromosomal DNA in the pUX12 vector was screened with the above-discussed protective anti-C proteins antisera. The group B Streptococcus library had an average fragment size of 1.4 kb. Transformants were screened as described above, and then subcloned and rescreened with the antisera three times. Of 20,000 clones screened, there were 35 independently isolated clones that reacted with the protective antisera. The clones were denominated S1-S35, and the plasmids containing the clones were denominated pJMS1-pJMS35. The clones ranged in size from 0.9 to 13.7 kb and have an average size of 4.5 kb.

Plasmid DNA was isolated from the clones by minipreps and the inserts surveyed with four restriction endonucleases. Fourteen of the clones can be divided into three groups based on sharing identical insert sizes and common restriction endonuclease mapping patterns within each group. Clones S1 and S23, discussed below, were found to be members of different groups.

By further comparing the restriction patterns of the individual clones it was possible to identify 24 clones that shared common restriction fragments. Clones S1 and S23 were not found to share any common restriction fragments.

Extracts of the clones were prepared, run on Western blots and probed with the antisera used in screening the library. Six size classes of protein antigens were identified (A–F). By combining data from the restriction endonuclease mapping and the Western blots it was possible to classify 24 of the 35 clones into 6 different protein antigen patterns (Table 2). This initial classification was done only to get a rough survey of the potential number of genes involved. S1 was found to be 3.5 kd in size, and to belong to antigen protein pattern A. S23 was found to be 13.7 kd in size, and to belong to antigen protein pattern D.

TABLE 2

PRELIMINARY CLASSIFICATION OF THE GROUP B STREPTOCOCCUS C PROTEIN CLONES

| Protein Profile | Number of clones | Molecular Weight of insert (kb) | Coding Capacity of DNA insert | Size of Antigen (in daltons) |
|---|---|---|---|---|
| A | 6 | 3.5 | 136,000 | 115,000 |
| B | 3 | 1.9 | 76,000 | 50,000 |
| C | 7 | 4.4 | 174,000 | 130,000 |
| D | 6 | 13.7 | >500,000 | 110,000 |
| E | 1 | 1.7 | 67,000 | 50,000 |
| F | 1 | 0.9 | 36,000 | 15,000 |

When Western blots of extracts of the clones were probed with antisera to a group B Streptococcus strain that does not express the C proteins, only one group of clones was positive (Protein Profile B). This indicates that the majority of positive clones express proteins that are unique to strains that carry the C proteins; these proteins are not common to all strains of group B Streptococcus.

EXAMPLE 7

Characterization of the Cloned Gene Sequences

The actual number of C proteins that are expressed by group B Streptococcus has not been determined. Recent immunological studies by Brady et al characterizing C protein typing antisera from the C.D.C. identified four separate antigens (Brady, L. J., et al., *J. Infect. Dis.* 158(5):965–972 (1988)). Preliminary genetic and immunological characterization of the putative C protein clones of group B Streptococcus suggests that four or five genes encode proteins that are present on strains of group B Streptococcus that are known to carry the C proteins. Two groups of experiments were conducted to determine whether the cloned gene products represent C proteins.

As discussed above, studies of the C proteins had defined two phenotypes: one group of proteins that was sensitive to degradation by pepsin but not trypsin (called TR or α) and another group of proteins that was sensitive to degradation by both pepsin and trypsin (called TS or β) (Johnson, D. R., et al., *J. Clin. Microbiol.* 19:506–510 (1984), Russell-Jones, G. J., et al., *J. Exp. Med.* 160:1476–1484 (1984)).

The typing antisera, α and β, were used to screen the cloned gene products on Western blots (Bevanger, L., et al., *Acta Path. Microbiol. Scand. Sect. B.* 87:51–54 (1979); Bevanger, L., et al., *Acta. Path. Microbiol. Scand. Sect. B.* 89:205–209 (1981); Bevanger, L., et al., *Acta. Path. Microbiol. Scand. Sec. B.* 91:231–234 (1983); Bevanger, L., et al., *Acta. Path. Microbiol. Scand. Sect. B.* 93:113–119 (1985); Bevanger, L., et al., *Acta. Path. MicrobioL Immuol. Scand. Sec. B.* 93:121–124 (1985) which references are incorporated herein by reference).

The α typing sera identified Protein Profile D, and the β typing antisera identified Protein Profile A. These proteins were subjected to digestion with pepsin and trypsin. Protein Profile D is sensitive to pepsin but not trypsin, and Protein Profile A is sensitive to both pepsin and trypsin. These results are consistent with previous studies and confirm that at least two of the C protein genes have been cloned.

The most important and characteristic property of the C proteins is their ability to elicit protective antibodies against group B Streptococcus strains that express C proteins. Several approaches could be used to prepare antisera against the cloned gene products. For example, lysates of the *E. coli* clones could be directly injected into rabbits in order to determine if the lysates contain proteins capable of eliciting antibodies to any of the *E. coli* or group B Streptococcus proteins introduced. The resulting antisera can be preabsorbed with a lysate of *E. coli* prior to testing the antisera to reduce the number of cross-reacting antibodies. Such a lysate can be used to reduce the number of cross-reacting antibodies in both colony blots used for screening the clones for expression and in Western blots used to study both cellular extracts of group B Streptococcus and partially purified group B Streptococcus proteins.

Representative clones from Protein Profiles A, B and D are sonicated and injected into rabbits to raise antisera against the cloned group B Streptococcus protein antigens (Lancefield, R. C., et al., *J. Exp. Med.* 142:165–179 (1975), Valtonen, M. V., et al., *Microb. Path.* 1:191–204 (1986)). The control rabbits are injected with *E. coli* that carries pUX12 without an insert in the polylinker. The antisera is preadsorbed with an *E. coli* lysate and screened first on Western blots against extracts of the clones in the library. Therefore, it is possible to determine if there are cross-reacting epitopes between the clones and to confirm that these antisera are directed against the cloned proteins identified during the preliminary round of screening.

Alternatively, the preadsorbed antisera may be tested in the mouse protection model. In this classic model, the mice are injected intraperitoneally with rabbit antisera (Lancefield, R. C., et al., *J. Exp. Med.* 142:165–179 (1975)). The following day they are again injected intraperitoneally with an $LD_{90}$) of viable group B Streptococcus that are known to carry C proteins. The endpoint is the death of the mice over a 48 hour period.

In order to test the immunogenicity of the proteins expressed by the cloned gene sequences, *Escherichia coli* cells containing pJMS1 and pJMS23 were grown, and used to prepare cellular extracts. These extracts were then used to immunize rabbits. Antisera raised in response to immunization with the S1 and the S23 extracts were tested using the mouse protection model.

When the mouse protection model experiment was performed, the antisera raised from the clones representing Protein Profiles A and D (S1 and S23, respectively), were each found to be protective. Antisera from a clone representing Protein Profile C was not protective and the control antisera also did not show protection. The antisera raised against the clones expressing Protein Profile C also binds to proteins extracted from strains of group B Streptococcus that do not carry the C protein. Therefore, this group of clones do not encode C proteins. In summary, five of the six groups of clones do not encode proteins that are unique to strains of group B Streptococcus that express C proteins.

The initial biochemical, immunological and functional analysis of two of the groups of clones demonstrates that at least two C proteins genes (S1 and S23) have been successfully cloned. This is the first demonstration that single polypeptide gene products cloned from group B Streptococcus can elicit protective immunity. Antibodies to S1 were found to be able to bind two bands of the A909 extract at 50 and 60 kd. Antibodies to S23 were found to be able to bind to a regularly repeating pattern of bands in the group B Streptococcus surface extract which ranged in MW from >180 kd to 40 kd. A monoclonal antibody derived from the A909 extract showed this same repeating pattern of immunoreactivity. This indicates that a single epitope was recognized in different molecular weight proteins and suggests a regularly repeating structure. The proteins recognized by the S1 antiserum were susceptible to pepsin and trypsin degradation whereas those recognized by the S23 antiserum were susceptible to pepsin but not to trypsin. This experiment shows that these proteins partially purified from group B Streptococcus and expressed from the group B Streptococcus cloned genes represent the alpha and beta antigens of the C protein of group B Streptococcus.

The 35 potential C protein clones described above may be evaluated both genetically and immunologically to determine the number of genes that are present. In addition, the isolation of these clones permits the genes which confer protective immunity to group B Streptococcus infection may be identified. It is likely that the protective antisera used to obtain the initial clones also detected proteins other than the C proteins. The use of such other proteins in a therapy against Streptococcus B infection is also contemplated by the present invention. Since a major goal of the present invention is the isolation and identification of the proteins involved in immunity, antisera prepared against the proteins expressed by these clones may be studied in the mouse protection model. Those genes that express proteins that are protective are preferred proteins for a conjugate vaccine.

As discussed above, the initial screening of group B Streptococcus chromosomal DNA in an *E. coli*/pUX12 vector library with protective antisera resulted in 35 independently isolated clones. By combining data from restriction endonuclease mapping of the cloned fragments and Western blots of protein extracts from the clones, it was possible to tentatively classify 24 of the 35 clones into 6 different protein antigen patterns (Table 2). This survey permitted a determination of the potential number of genes isolated.

To further characterize such clones, colony blots are preferably used to determine which clones share common DNA sequences. For such blots, a single colony of each of the clones is placed in a well of microtiter dish containing LB broth and grown at 37° C. overnight. Control colonies include the host *E. coli* strain and the *E. coli* strain containing pUX12. The overnight cultures are transferred onto a nitrocellulose filter on an agar plate containing the same culture medium. These plates are grown up over 8 hours at 37° C. and the nitrocellulose filter containing the freshly grown colonies is prepared to be screened for DNA-DNA hybridization. The probes are prepared from the group B Streptococcus DNA inserts in the pUX12 library. Mini-preps are used to obtain plasmid DNA from the clones. The polylinker in pUX12 has both a BamHI and BstXI site on either side of the insert; therefore, the group B Streptococcus insert is excised from the plasmid using either BamHI or BstXI. Fortunately, the chromosomal DNA of group B Streptococcus contains few BamHl sites and many of the inserts are removed from the vector in one fragment as the result of digestion with BamHI. Low melting point agarose is used to separate the plasmid vector from the inserts. The inserts will be cut from the agarose gel and directly labeled by random prime labeling. The labeled inserts are then used to probe the colony blots. This results in the identification of clones that share DNA sequences.

Thus, on the basis of the information obtained from the colony blots described above, the 35 clones are placed into groups that share DNA sequences. These groups are mapped with multiple restriction endonucleases to determine the relationship of each clone to the others within that region of the DNA. Since the host plasmid, pUX12, contains many unique restriction endonucleases sites that are present only in the polylinker, much of the restriction mapping can be done utilizing the plasmid mini-prep DNA without needing to purify the inserts separately. By combining the colony blot data with detailed restriction mapping it is possible to get a reasonable assessment of the number of genetic loci involved. If some of the groups of clones do not represent the genes of interest in their entirety, it may be necessary to use these clones to isolate other more complete copies of the genes from the chromosomal library. However, given the large average size distribution of the initial 35 clones isolated, it is likely that some may represent a complete open reading frame.

Before proceeding with a genetic analysis, antisera is preferably prepared against the cloned gene products, and utilized in the mouse protection model to determine the ability of these antisera to protect against infection with group B Streptococcus (Lancefield, R. C., et al., *J. Exp. Med.* 142:165–179 (1975), Valtonen, M. V., et al., *Microb. Path.* 1:191–204 (1986)).

A clone whose expressed protein is able to elicit protective antibodies is a preferred candidate for use in a conjugate vaccine. Clones whose expressed protein fails to elicit protective antibodies may be further analyzed to determine whether they are also candidates for a vaccine. Since the C proteins are membrane associated, a failure of protein expressed by a clone to elicit protective antibodies may reflect the fact that the protein may not be stable in *E. coli*, and in a high copy number vector. This problem has occurred in cloning other membrane proteins from both group A and group B Streptococcus (Kehoe, M. et al., Kehoe, M., et al., *Infect. and Immun.* 43:804–810 (1984), Schneewind, O., et al., *Infect. and Immun.* 56:2174–2179 (1988)). Several of the 35 clones isolated in the preliminary studies show a small colony morphology. In addition, some of these clones are unstable and have been found to delete part of the group B Streptococcus DNA insert from the pUX12 polylinker. There are several techniques that can be used to stabilize these clones including: cloning into a low copy number vector or behind a promoter that can be down-regulated, growing the clones at 30° C. instead of 37° C., cloning into a vector that has been adapted to accumulate membrane proteins. In addition, it is possible to transform the plasmids into an *E. coli* host, pcnB, that restricts the copy number of pBR322 derived plasmids like pUX12 (Lopilato J., et al., *Mol. Gen. Genet.* 205:285–290 (1986) which reference is incorporated herein by reference).

A failure of a clone to express protein which elicits protective antibodies may also indicate that the expressed protein lacks an epitope which is important for protection. This could be the case if the entire gene was not cloned or could not be expressed in *E. coli*. It might also be problem if there is post-transcriptional processing of the C proteins in group B Streptococcus but not for the cloned C protein genes in *E. coli*. It might be necessary either to subclone out the complete gene and/or transfer it into an alternate host background where it can be expressed.

A failure of a clone to express protein which elicits protective antibodies may also indicate that antibodies elicited from antigens produced in *Escheflchia coli* may differ from those elicited from an Streptococche native C proteins on group B Streptococcus. In addition, the lysed bacterial extracts used to immunize the rabbits contain a number of *E. coli* protein antigens. Therefore, it may be necessary to obtain antisera for testing in the animal model from partially purified gene products instead of from the entire organism.

Any cloned group B Streptococcus proteins that are able to elicit protective antibodies can be called C proteins. The antisera prepared for this group of experiments will also be used for localizing these protein.

EXAMPLE 8

Mapping, Characterization and Sequencing of the C Protein Genes

In order to further characterize the C protein genes, a fine structure genetic map of C protein gene clones described above may be prepared and their DNA sequence(s) determined. Such mapping is preferably accomplished utilizing genomic Southern blots. By determining the DNA sequences of the C protein genes, one can determine the structure of the genes including their ribosomal binding sites, potential promoters, signal sequences, and any unusual repetitive sequences. The DNA sequences are preferably compared to a library of known DNA sequences to see if there is homology with other genes that have been characterized. In addition, the protein sequences of the C proteins can be determined from DNA sequences of their genes. It is often possible to make predictions about the structure, function and cellular location of a protein from the analysis of its protein sequence.

Genomic Southern blots are, thus, preferably used to determine if any of the genes are linked. For this technique, group B Streptococcus chromosomal DNA is digested individually with several different restriction endonucleases that identify sequences containing six or more base pairs. The purpose is to obtain larger segments of chromosomal DNA that may carry more than one gene. The individual endonuclease digestions are then run out on an agarose gel and transferred onto nitrocellulose. The Southern blots are then probed with the labelled inserts derived from the above-described library. If two clones that did not appear related by the colony blots or endonuclease mapping bind to similar chromosomal bands, this would indicate that either they are part of the same gene, or that they are two genes that are closely linked on the chromosome. In either case, there are several ways to clone out these larger gene segments for further study. One technique is to prepare a cosmid library of group B Streptococcus and screen for hybridization with one of the probes of interest. When a clone is obtained that contains two or more genes of interest it could be endonuclease mapped and studied for the expression of protective antigens as described for the previously described clones.

The identification of the above-described clones permits their DNA sequences to be determined. If the clones are on the pUX12 plasmid, it is possible to use double stranded DNA sequencing with reverse transcriptase to sequence from oligonucleotide primers prepared to the polylinker. This technique was used earlier in characterizing the pUX12 plasmid and is a rapid way to sequence multiple additional oligonucleotide primers to sequence a gene that is larger than 600 base pairs. Therefore, the DNA sequencing for the C protein genes is preferably performed by subcloning into an M13, single stranded DNA sequencing system (Ausubel, F. M., et al., *Current Topics in Molecular Biology* (1987)).

The elucidation of the DNA sequences of the C proteins provides substantial information regarding the structure, function and regulation of the genes and their protein products. As discussed earlier, the heterogeneity in the sizes of C proteins isolated by many investigators and their apparent antigenic diversity suggests the possibility of either a gene family, or a post-transcriptional mechanism for modifying the protein products of the C protein genes (Ferrieri, P., et al., *Infect. Immun.* 27:1023–1032 (1980)). The M protein of group A Streptococcus was discussed earlier as an example of this phenomenon (Scott, J. R., et al., *Proc. Natl. Acad. Sci. USA* 82:1822–1826 (1985)). Although the DNA sequence of M protein shows no homology with group B Streptococcus chromosomal DNA by hybridization, there may be structural homologies between their DNA sequences (Hollingshead, S. K., et al., *J. Biol. Chem.* 261:1677–1686 (1986), Scott, J. R., et al., *Proc. Natl. Acad. Sci. USA* 82:1822–1826 (1985), Scott, J. R., et al., *Infect. and Immun.* 52:609–612 (1986)). The DNA sequences of the C proteins are preferably compared with a library of known DNA sequences. In addition, the amino acid sequences derived from the DNA sequences are compared with a library of known amino acid sequences.

EXAMPLE 9

Prevalence of the C Protein Genes

To determine the prevalence of the C protein genes, chromosomal DNA from clinical and laboratory isolates of the various serotypes of group B Streptococcus are probed on genomic Southern blots with the C protein genes. In addition, comparison of the phenotypic expression as determined by precipitin techniques with genetic composition as shown by DNA-DNA hybridization is preformed in order to provide information regarding the regulation of expression of the C protein genes. The probes of the C protein genes are used to screen chromosomal DNA from other types of Streptococcus, and other bacterial pathogens.

Probes are prepared and labelled from the C protein genes of isolates of group B Streptococcus which includes most of the original typing strains used by Lancefield (Lancefield, R. C., et al., *J. Exp. Med.* 142:165–179 (1975)). Colony blots of the 24 clinical and laboratory isolates of group B Streptococcus are screened using the microtiter technique described above. The ability of the various strains to hybridize to the C protein genes is then compared with the phenotypic characteristics of these organisms in binding to typing antisera directed against the C proteins. In this manner, it is possible to determine what strains carry any or all of the C protein genes, and whether some strains carry silent or cryptic copies of these genes.

Those strains that hybridize to the C protein gene probes on colony blots are then screened using genomic Southern blots to determine the size, structure and location of their C protein genes. Chromosomal DNA isolated from the strains of group B Streptococcus that show binding on the colony blots is digested with restriction endonucleases, run on an agarose gel and blotted onto nitrocellulose. These Southern blots are probed with probes of the C protein genes. In this manner, it is possible to determine if there are differences in the location and size of these genes in the different serotypes of group B Streptococcus and to compare clinical (i.e. potentially virulent) isolates with laboratory strains (and with those which colonize clinically but are not associated with infection).

The C protein gene probes are also preferably used to screen other streptococcal strains and a variety of pathogenic bacteria. Streptococcal strains are known to share other proteins associated with virulence including the M and G proteins (Fahnestock, S. R., et al., *J. Bact.* 167(3):870–880 (1986), Heath, D. G., et al., *Infec. and Immun.* 55:1233–1238 (1987), Scott, J. R., et al, *Infec. and Immun.* 52:609–612 (1986), Walker, J. A., et al., *Infec. and Immun.* 55:1184–1189 (1987) which references are incorporated herein by reference). The strains to be tested are first screened using colony blots to determine whether they have any homologous sequences with the C protein genes probes. Genomic Southern blots are then prepared with the chromosomal DNA of the bacterial strains that test positive on the colony blots. These blots are then probed with the C protein genes to localize and define the areas of homology, such as a region of a C protein which serves as a membrane anchor, binds to the Fc region of immunoglobulins, or shares regions of homology with other genes with similar functions in other bacteria.

EXAMPLE 10

Modification of the C Protein Genes in Group B STREPTOCOCCUS

A number of potential virulence associated properties have been ascribed to the C proteins including resistance opsonization and inhibition of intracellular killing following phagocytosis (Payne, N. R, et al., *J. Infec. Dis.* 151:672–681 (1985), Payne, N. R., et al., *Infect. and Immun.* 55:1243–1251 (1987)). To better understand the roles of the C proteins in virulence, isogeneic strains are constructed in which the C protein genes are individually mutated. These strains will be tested for virulence in the neonatal rat model (Zeligs, B. J., et al., *Infec. and Immun.* 37:255–263 (1982). Two methods may be utilized to create isogeneic strains to evaluate the role of the C proteins in the virulence of group B Streptococcus. Preferably, tranposon mutagenesis with the self-conjugative transposon tn916 may be employed. Alternatively, site-directed mutagenesis may be used. The lack of efficient methods for genetic manipulation in group B Streptococcus necessitates the development of new genetic techniques to modify genes in group B Streptococcus and create isogeneic strains for studying virulence (Lopilato, J., et al., *Mol. Gen. Genet.* 205:285–290 (1986) which reference is incorporated herein by reference).

Transposon insertional mutagenesis is a commonly used technique for constructing isogeneic strains that differ in the expression of antigens associated with virulence, and its use in group B Streptococcus is well described (Caparon, M. G., et al., *Proc. Natl. Acad. Sci. USA* 84:8677–8681 (1987), Rubens, C. E., et al., *Proc. Natl. Acad. Sci USA* 84:7208–7212 (1987), Wanger, A. R, *Res. Vet. Sci.* 38:202–208 (1985), Weiser, J. N., *Trans Assoc. Amer. Phys.* 98:384–391 (1985) which references are incorporated herein by reference). Rubens, et aL have demonstrated the utility of Tn916 in studies of the group B Streptococcus capsule (Rubens, C. E., *Proc. Natl. Acad. Sci. USA* 84:7208–7212 (1987). The self-conjugating transposon TN916 may be made from *Streptococcus faecalis* into group B Streptococcus as previously described (Wanger, A. R., *Res. Vet. Sci.* 38:202–208 (1985) which reference is incorporated herein by reference). Strains are selected for the acquisition of an antibiotic resistance marker, and screened on colony blots for the absence of expression of the C proteins as detected by the specific antisera prepared as described above. Isolates that do not appear to express the C proteins can be further mapped using genomic Southern blots to localize the insertion within the C protein genes. The original Tn916 strain carried $tet^R$; however, an erythromycin resistance marker has recently been cloned into Tn916 (Rubens, C. E., et al., *Plasmid* 20:137–142 (1988)). It is necessary to show that, following mutagenesis with Tn916, only one copy of the transposon is carried by the mutant strain and that the transposon is localized within the C protein gene.

The application of these techniques to deleting the C protein genes in group B Streptococcus is straightforward, unless a C protein genes is essential to the survival of group B Streptococcus. However, strains of group B Streptococcus have been described that lack any detectable C protein and it is unusual for a bacterial virulence determinant to be an essential gene for survival in vitro. A n additional use of Tn916 that will be explored is the identification of potential regulatory elements of the C protein genes.

In the event that specific defined mutations are desired or if the C protein gene is essential for the viability of group B Streptococcus, techniques of site-directed mutagenesis may be employed (for example to produce conditional mutants). Site-directed mutagenesis may thus be used for the genetic analysis of group B Streptococcus proteins. One problem that has delayed the development of these techniques in group B Streptococcus is the difficulty encountered in transforming group B Streptococcus. Electroporation has proven valuable in introducing DNA into bacteria that are otherwise difficult to transform (Shigekawa, K., et al., *BioTech.* 6:742–751 (1988) which reference is incorporated herein by reference). Conditions for transforming group B Streptococcus utilizing electroporation may be utilized to surmount this obstacle. It is thus possible to do site directed mutagenesis, to evaluate complementation, and to introduce C protein genes into group B Streptococcus strains that do not express the C proteins. Any of several approaches may be utilized to insert native or mutated C protein genes into strains of group B Streptococcus. For example, a drug resistance marker may be inserted within the C protein gene clones in pUX12. A drug resistance marker that can be expressed in group B Streptococcus, but that is not normally present, is preferred. This modified pUX12 protein clone is transformed into group B Streptococcus using electroporation (Shigekawa, K., et al., *BioTech* 6:742–751 (1988) which reference is incorporated herein by reference). Since the pUX12 plasmid cannot replicate in group B Streptococcus, those strains that acquire the drug resistance phenotype would likely do so by homologous recombination between the C protein gene on the host GB chromosome and the mutated C protein carried on the pUX12 plasmid. The mutants are screened as described above. If there are no homologous sequences in the recipient strain, it is possible to construct a vector with the C protein gene inserted within a known streptococcal gene, i.e., a native drug resistance marker gene from group B Streptococcus. Following electroporation, such a plasmid construct would integrate into the chromosome via homologous recombination.

Alternatively, modified C protein genes could be introduced into the group B Streptococcus chromosome by inserting the genes into the self-conjugating transposon Tn916 and introducing the modified transposons via mating from Streptococcusfaecalis. This technique was used to successfully modify Tn916 with an erythromycin gene and insert this gene into the chromosome of group B Streptococcus (Rubens, C. E., et al., *Plasmid* 20:137–142 (1988)). It is necessary to show that, following mutagenesis with Tn916, only one copy of the transposon is carried by the mutant strain and that the transposon is localized within the C protein gene.

EXAMPLE 11

Evaluation of the Role of the C Proteins in Virulence of Group B STREPTOCOCCUS

Previous studies that compared strains of group B Streptococcus that do and do not carry C proteins involved isolates that were not known to be isogeneic (Ferrieri, P., et al., *Rev. Inf. Dis.* 10(2):1004–1071 (1988)). Therefore, it was not possible to determine whether the differences in virulence observed are related to the C proteins or to some other virulence determinant. The construction of isogeneic strains having either intact C protein genes or C protein gene deletions permit a characterization of the role of the C protein in virulence. The strains are preferably tested in the neonatal rat model for virulence and in the mouse protection model for their immunological properties. A second important test of virulence is the ability of a gene to restore virulence through reversion of allelic replacement in a mutant strain. By inserting the C protein genes into group B Streptococcus strains that either do not carry the gene or which carry inactivated C protein genes, it is possible to determine the effect of the C protein by examining the virulence of the resulting construct in the above animal models.

Isogeneic strains of group B Streptococcus in which the C protein genes are individually mutated may be created using either transposon mutagenesis or site-directed mutagenesis. Such strains are preferably characterized on genomic Southern blots to determine that only a single insertion is present on the chromosome. The location of these insertions may be ascertained using the fine structure genetic mapping techniques discussed above. The isogeneic strains are then tested for virulence in the neonatal rat model (Zeligs, B. J., et al., *Infec. and Immun.* 37:255–263 (1982)).

Transposon mutagenesis permits the identification of genes involved in regulating the expression of the C proteins. For example, strains carrying the wild type C protein genes which are found to no longer express C proteins following transposon mutagenesis and in which transposon is not located within the C protein structural gene, carry mutations in sequences involved in the regulation of expression of the C protein genes. This approach was used successfully in characterizing the mry locus in group A Streptococcus that is involved in regulation of the M protein (Caparon, M. G., et al., *Proc. Natl. Acad. Sci. USA* 84:8677–8681 (1987), Robbins, J. C., et al., *J. Bacteiol.* 169:5633–5640 (1987) which references are incorporated herein by reference). Such methods may also be used to produce strains which overexpresses the C proteins, or which produce C proteins of altered virulence or immunity.

EXAMPLE 12

Localization of the C Proteins on Group B Streptococcus and Evaluation of their Ability to Bind to Immunoglobulins Lancefield and others have shown that antibody to the C proteins binds to the outer membrane of group B Streptococcus (Lancefield, R. C., et al., *J. Exp. Med.* 142:165–179 (1975), Wagner, B., et al., *J. Gen. Microbiol.* 118:95–105 (1980)). This suggests that the C protein is an outer membrane protein. C proteins can also be isolated from the supernatants of cultures of group B Streptococcus, indicating that these proteins may be either secreted by group B Streptococcus or lost at a high rate from the cell surface. The DNA and protein sequences derived from the C protein genes are valuable in determining the structure and function of the C proteins. One potential virulence determinant commonly described for the C proteins is the ability to bind to the immunoglobulin, IgA (Ferrieri, P., et al., *Rev. Inf. Dis.* 10(2):1004–1071 (1988), Russell-Jones, G. J., et al., *J. Exp. Med.* 160:1467–1475 (1984)).

Immuno-electron microscopy has been utilized to localize cell surface determinants that are detected by specific antibody. Antisera raised against the C protein clones of group B Streptococcus is incubated with group B Streptococcus strains that carry the C proteins. Ferritin-conjugated goat anti-rabbit IgG is used to detect the antigen on the cell surface as previously described (Rubens, C. E., et al., *Proc. Natl. Acad. Sci. USA* 84:7208–7212 (1987), Wagner B., et al., *J. Gen. Microbiol.* 118:95–105 (1980)).

A simple determination of the ability of C proteins to bind to immunoglobulins can be assessed using Western blots. Cellular extracts of both the *E. coli* clones containing the C protein genes and of group B Streptococcus strains that carry the C proteins can be run on SDS-PAGE and blotted onto nitrocellulose. Controls include extracts of *E. coli* carrying the wild type pUX12 plasmid, strains of group B Streptococcus that do not carry the C protein genes, and isogeneic group B Streptococcus strains in which the C protein genes have been inactivated. The Western blots can be probed individually with labelled immunoglobulins, e.g., IgG, IgM, IgA, and their components, e.g., the Fc or F(ab)$_2$ fragments (Heath, D. G., et al., *Infect. and Immun.* 55:1233–1238 (1987), Russell-Jones, G. J., et al., *J. Exp. Med.* 160:1467–1475 (1984)). The immunoglobulins are preferably iodinated using either iodogen or chloramine T.

A more specific way to measure the ability of the C proteins to bind to immunoglobulins and their components involves purifying the C proteins and using them directly in a binding assay (Fahnestock, S. R., et al., *J. Bact.* 167(3):870–880 (1986), Heath, D. G., et al., *Infect. and Immun.* 55:1233–1238 (1987)). Using the protein sequence, one can purify the C protein. In addition, since it is possible to express the C protein genes in *E. coli*, one may construct *E. coli* strains that overproduce the C proteins and thereby obtain larger amounts of C proteins for purification.

EXAMPLE 13

Use of the Cloned C Protein Antigenes of Group B Streptococcus Vaccine

Figure 4:
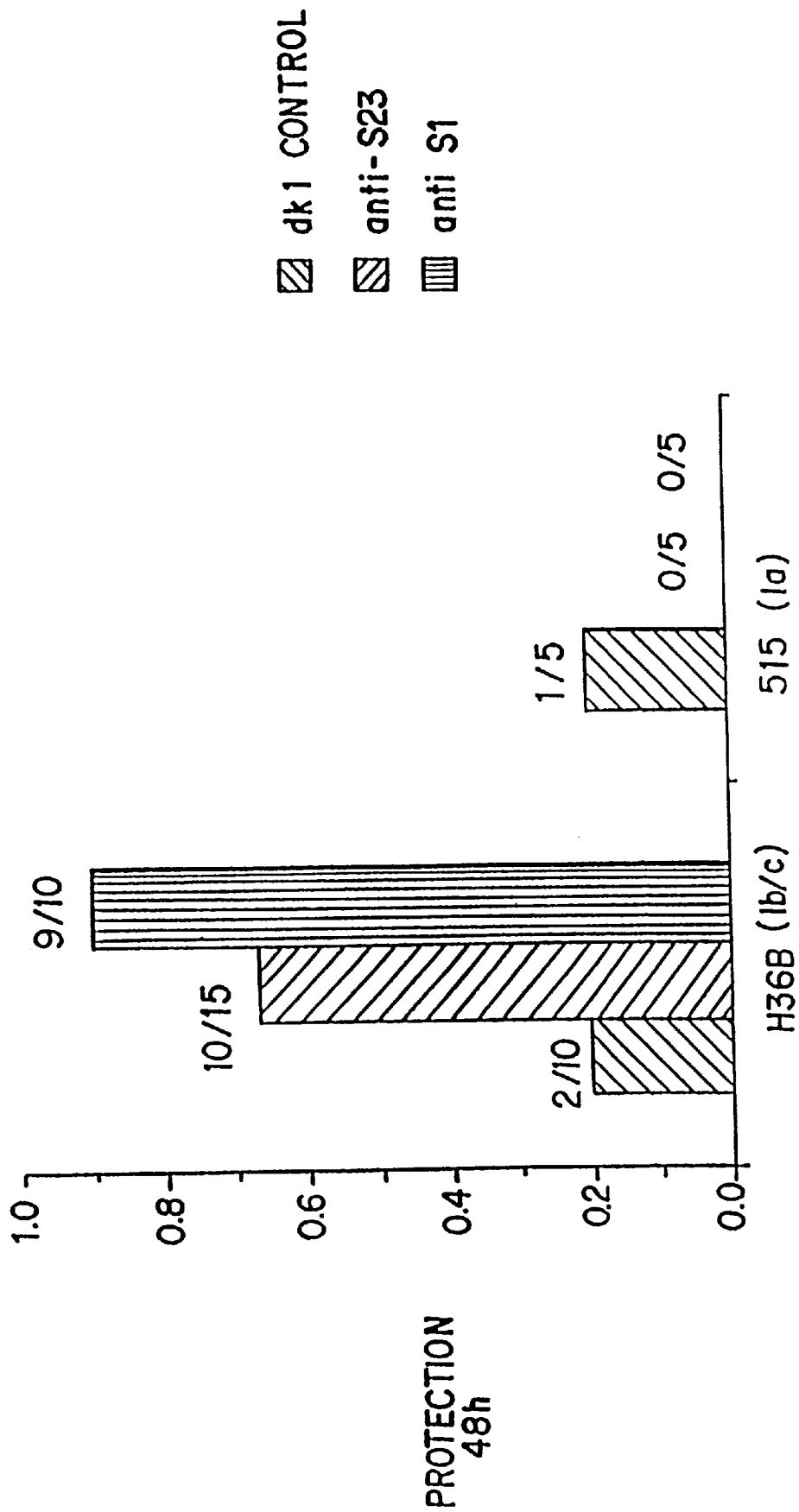
FIG. 4 shows the result of mouse protection studies employing rabbit antisera against S1 and S23. Protection was observed in mice inoculated with anti-S1 antisera (p<0.002) or with anti-S23 antisera (p<0.022). Due to the sample size used, this difference in the observed statistical significance between the S1 and S23 experiments is not significant. In the Figure, the mice surviving per total tested is reported as a fraction above each bar.

The above-described protective C protein antigens of group B Streptococcus were tested for their potential in a conjugate vaccine. To assess this potential, cellular extracts of *E. coli* containing pJMS 1 or pJMS23 were prepared as described above, and used to immunize rabbits. The resulting antisera was tested in the mouse lethality model for its ability to protect mice from infection by the group B Streptococcus strain H36B. Strain H36B carries the C protein of group B Streptococcus. As a control, the ability of the antisera to protect the mice against infection by Streptococcus strain 515 (which does not carry the C protein) was determined. The results of this experiment are shown in FIG. 4.

EXAMPLE 14

The Sequence of the C Protein Alpha Antigen and its Repeating Units

As stated above, *Streptococcus agalactine* [group B Streptococcus (GBS)] is an important pathogen in neonatal sepsis and meningitis, postpartum endometritis, and infections in adults, in particular in diabetics and immunocompromised hosts (Baker, C. J., et al., in *Infectious Diseases of the Fetus and Newborn Infant*, Remington, J. S. et al. Saunders, Philadelphia, (1990) pp. 742–811)). The best-studied GBS virulence determinants are the type-specific capsular polysaccharides that are essential for pathogenesis (Rubens, C. E., et al., *Proc. Natl. Acad. Sci. USA*

84:7208–7212 (1987); Wessels, M. R., et al., *Proc. Natl. Acad. Sci. USA* 86:8983–8987 (1989)). The roles of GBS surface proteins in infection are less well understood (Ferrieri, P. *Rev. Infect. Dis.* S363–S366 (1988); Michel, J. L., et al. in *Genetics and Molecular Biology of Streptococci, Lactococci, and Enterococci*, Dunny, G. M. et al. eds., Am. Soc. Microbiol., Washington (1991), pp. 214–218). The C proteins are surface-associated antigens expressed by most clinical isolates of capsular types. Ia, Ib, and II and are thought to play a role in both virulence and immunity (Johnson, D. R., et al., *J. Clin. Microbiol.* 19:506–510 (1984); Madoff, L. C., et al. *Infect. Immun.* 59:2638–2644 (1991)). Two C protein antigens, alpha and beta, have been described biochemically and immunologically (Michel, J. L., et al. in *Genetics and Molecular Biology of Streptococci, Lactococci, and Enterococci*, Dunny, G. M. et al. eds., Am. Soc. Microbiol., Washington (1991), pp. 214–218).

In 1975, Lancefield et al. (Lancefield, R. C., et al., *J. Exp. Med.* 142:165–179 (1975)) showed that antibodies raised to the C proteins in rabbits protected mice challenged with GBS bearing the C proteins. A monoclonal antibody to the alpha antigen (4G8) that induces opsonic killing of GBS and protects mice from lethal challenge with GBS has been described (Madoff, L. C., et al., *Infect. Immun.* 59:204–210 (1991), incorporated herein by reference). As shown above, the gene encoding the encoding alpha and beta antigens were cloned and expressed in *Eschefichia coli*. It was shown that antibodies raised to the clones of both alpha and beta encode different C proteins that define unique protective epitopes (Michel, J. L., et al., *Infect. Immnun.* 59:2023–2028 (1991)). The alpha and beta antigens are independently expressed and antigenically distinct proteins.

The C protein beta antigen that specifically binds to human serum IgA has been cloned (Michel, J. L., et al., *Infect. Immun.* 59:2023–2028 (1991); Cleat, P. H., et al., *Infect. Immun.* 55:1151–1155 (1987)) and sequenced (Heden, L.-O., et al., *Eur. J. Inununol.* 21:1481–1490 (1991); Jerlstrom, P. G., et al., *Mol. Microbiol.* 5:843–849 (1991)). However, the role of the beta antigen and IgA binding in virulence is not known. Studies by Ferrieri et al. (Payne, N. R., et al., *J. Infect. Dis.* 151:672–681 (1985); Payne, N. R., et al., *Infect. Immnun.* 55:1243–1251 (1987)) showed that C protein-bearing strains of GBS resist phagocytosis and inhibit intracellular killing. Opsonophagocytic killing in the presence of alpha antigen-specific monoclonal antibody (4G8) correlated directly with increasing molecular mass of the alpha antigen and with the quantity of alpha antigen expressed on the bacterial cell surface (Madoff, L. C., et al., *Infect. Immun.* 59:2638–2644 (1991)). GBS strains expressing the alpha antigen Were resistant to killing by polymorphonuclear leukocytes in the absence of specific antibody; however, this resistance was not dependent on the size of the alpha antigen.

The completed nucleotide sequence of bca and flanking regions reported here provides information regarding the size, structure, and composition of the alpha antigen gene. An interesting feature of both the native and cloned gene products of the alpha antigen is that they exhibit protein heterogeneity by expressing a regularly repeating ladder of proteins differing by approximately 8000 Da (Madoff, L. C., et al., *Infect. Immun.* 59:204–210 (1991); Michel, J. L., et al., *Infect. Immun.* 59:2023–2028 (1991)). Since the protective monoclonal antibody 4G8 binds to the repeat region, this region defines a protective epitope (Madoff, L. C., *Infect. Immun.* 59:2023–2028 (1991)). Smaller tandemly repeated sequences encoding immunodominant epitopes have been reported in a number of pathogens but have not been associated with the protein heterogeneity seen in the alpha antigen (Enes, V., et al., *Science* 225:628–630 (1984); Fischetti, V. A., et al., *Rev. Infect. Dis.* S356–S359 (1988); Pereira, M. E., et al., *J. Exp. Med.* 174:179–191 (1991); Fischetti, V. A., et al., in *Genetics and Molecular Biology of Streptococci, Lactococci, and Enterococci*, Dunny et aL eds. Am. Soc. Microbiol., Washington (1991), pp. 290–294; Dailey, D. C., et al., *Infect. Immnun.* 59:2083–2088 (1991); vonEichel-Streiber, C., et al., *Gene* 96:107–113 (1990)). Though the maximum molecular size of the alpha antigen differs among strains of GBS, this protein heterogeneity is a constant feature (Madoff, L. C., et al. *Infect. Immun.* 59:2638–2644 (1991)).

The nucleotide sequence of bca contains nine identical 246-nucleotide tandem repeating units. The estimated size of the peptide encoded by each of these repeats is 8665 Da and correlates with the intervals found in the heterogeneous laddering of the alpha antigen. The amino acid sequence derived from the DNA sequence revealed both significant homologies and important differences between the alpha antigen and other streptococcal proteins (Heden, L. O., et al., *Eur. J. Immunol.* 21:1481–1490 (1991); Jerlstrom, P. G., et al., *Mol. Microbiol.* 5:843–849 (1991); Fischetti, V. A., et al., in *Genetics and Molecular Biology of Streptococci, Lactococci, and Enterococci*, Dunny et al. eds. Am. Soc. Microbiol., Washington (1991), pp. 290–294). The repeating units of the alpha antigen suggest possible mechanisms for phenotypic and genotypic variability and provide natural sites for gene rearrangements that could generate antigen diversity.

Materials and Methods

Bacterial Strains, Plasmids, Transposons, and Media.

GBS strain A909 (type $1a/C_{\alpha,\beta}$) (Lancefield, R. C., et al., *J. Exp. Med.* 142:165–179 (1975)), *E. coli* strains MC1061 and DK1 (Ausubel, F. M., et al., *Current Protocols in Molecular Biology*, Wiley, New York (1990)), pCNB (Lopilato, J. et al., *Mol. Gen. Genet.* 205:285–290 (1986)), DH5α (a derivative of DH1; GIBCO/BRL), and NK-8032; *E. coli* plasmids and clones pUC12, pUX12, and pJMS23; and the transposon Tn5seq1 have been described (Michel, J. L., et al., *Infect. Immun.* 59:2023–2028 (1991)). The plasmid pGEM-7Zf(-) was purchased from Promega, Madison, Wis., USA. Additional subclones of pJMS23 (pJMS23-1, -7, -9, and -10) are described below. Growth media for GBS and *E. coli* and antibiotics for selection have been described (Michel, J. L., et al., *Infect. Immun.* 59:2023–2028 (1991)).

DNA Procedures and Nucleotide Sequencing Strategy.

Standard procedures for the preparation of plasmid DNA, synthesis and purification of oligonucleotides, restriction endonuclease mapping, agarose gel electrophoresis, and Southern blot hybridization are from Ausubel et al. (Ausubel, F. M., et al., *Current Protocols in Molecular Biology*, Wiley, New York (1990)). Restriction endonucleases and other enzymes for manipulation of DNA (e.g., DNase, RNase, and ligase) were obtained from New England Biolabs and Boehringer Manneheim. Transposon mutagenesis utilized lambda-Tn5seq1 (Nag, D. K., et al., *Gene* 64:135–145 (1988)).

Nucleotide sequencing of double-stranded DNA used plasmids containing transposon Tn5seq1 insertions using primers of Sp6 or T7 promoters for bidirectional sequencing, synthetic oligonucleotide primers, and nested deletions using Erase-a-Base (Promega, Madison Wis., USA; Henikoff, S., *Gene* 28:351 (1984)). A total of 12 primers were prepared to obtain the sequence in both directions for the areas of the gene flanking the repeat region. Sequencing of the region of repetitive DNA was completed with exonuclease III-generated nested deletions. All sequencing employed Sequenase kit, version 2, used according to manufacturer's specifications for double-stranded sequencing (United States Biochemical). Adenosine 5'-[α-[$^{35}$S]thio] triphosphate was obtained from Amersham. GenAmp PCR kit with AmpliTaq polymerase was used according to manufacturer's instructions (Perkin-Elmer/Cetus).

Subclones pJMS23-1, pJMS23-7, and pJMS23-10 were prepared for transposon mutagenesis to target smaller regions within bca (Michel, J. L. et al., *Infect. Immun.* 59:2023–2028 (1991)). Subclone pJMS23-1 contains a 5.9-kilobase HindIII fragment in pUX12; pJMS23-7 contains 2.8-kilobase Alu I fragment from pJMS23-1 ligated into the HincII site in the polylinker of pUC12; and pJMS23-10 is a BsaB1/Sma I double restriction endonuclease digestion of pJMS23-7 that yielded a 2.3 kilobase insert containing the repeat region. For nested deletions the Alu I fragment from pJMS23-1 was ligated into the Sma I site on pGEM-7Zf(−) to create pJMS23-9. Nested deletions were constructed in the forward direction from the HindIII and Nsi I sites and in the reverse direction from EcoRI and Sph I sites. The sizes of the subclones, mutants, and deletions used for sequencing were confirmed by restriction endonuclease mapping and/or PCR with primers to the pUC12 polylinker and to Tn5seq1 (Sp6 and T7).

Data analysis used the Department of Molecular Biology computer at Massachusetts General Hospital (Boston) with Genetics Computer Group (Madison, Wis.) version 7 software and the BLAST network of the National Center for Biotechnology Information of the National Institutes of Health (Bethesda, Md.).

Monoclonal Antibodies, SDS/PAGE, and Western Immunoblots.

Extracts of GBS and *E. coli* proteins, SDS/PAGE, immunoblotting, and probing with the alpha antigen monoclonal antibody 4G8 were performed as described in Madoff, L. C., et al. *Infect. Immun.* 59:2638–2644 (1991), in Madoff, L. C., et al., *Infect. Immun.* 59:204–210 (1991), and in Michel, J. L., et al., *Infect. Immun.* 59:2023–2028 (1991).

Results

Nucleotide Sequence of bca.

Subdlones of pJMS23, which encodes the bca locus from GBS strain A909 (type Ia/C) and expresses the alpha antigen in *E. coli*, were used for determining the sequence of bca (Michel, J. L., et al., *Infect. Immun.* 59:2023–2028 (1991)). As is often the case with Gram-positive genes cloned into *E. coli*, many of the subclones were unstable (Schneewind, O., et al., *Infect. Immun.* 56:2174–2179 (1988)). This problem is compounded in bca by a large region of repetitive DNA that provides multiple, fixed sites for homologous recombination.

Homologous recombination such as this may be purposely taken advantage of to generate a population of recombinant hosts that express a variety of alpha antigen functional derivatives. Such a population would be a mixtures of the alpha antigens and their functional derivatives and may be utilized in the vaccines of the invention to provide a wide range of alpha antigen sequences against which the host may direct the immune response.

Figure 5:
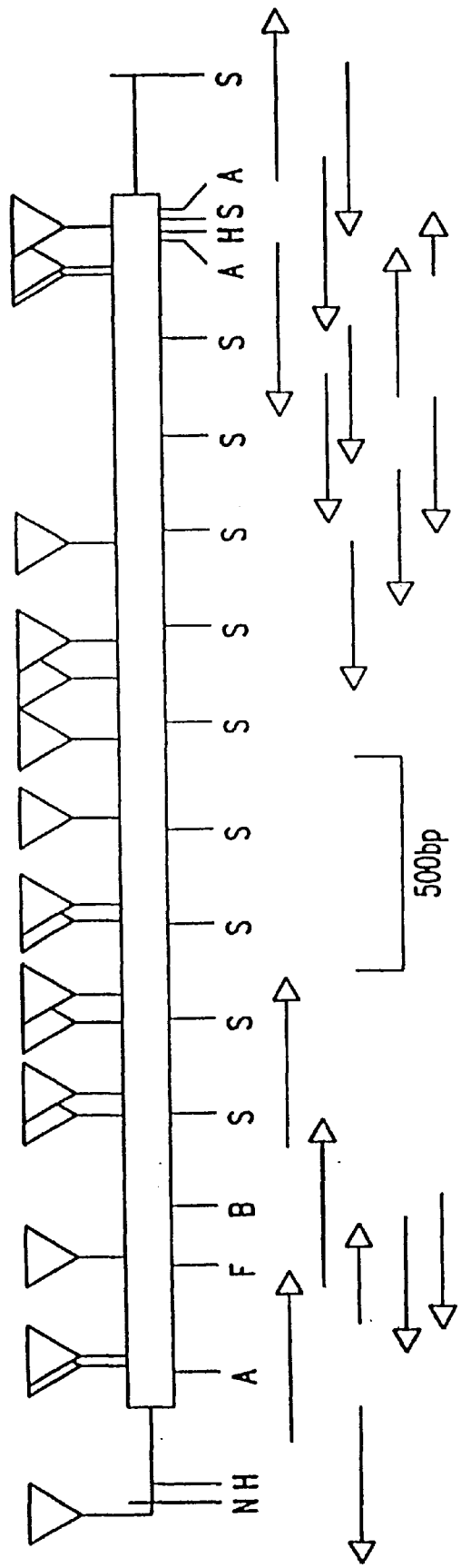
FIG. 5 shows the sequencing strategy and restriction endonuclease map of bca. The partial restriction endonuclease map encompasses the region of pJMS23 from an Nde I site to a Sty I site located at nucleotide 3594 for which the nucleotide sequence of bca and flanking region was determined. The open reading frame is illustrated by an open box. Transposon Tn5seq1 mutations (triangles) serve to prime nucleotide sequencing in both directions from each of the insertions. The regions of sequence obtained from oligonucleotide primers (open arrows) and the nested deletions (closed arrows) are also shown. Restriction endonuclease cleavage sites are abbreviated as follows: A, Alu I; B, Bsm I; F, Fok I; H, HincII; N, Nde I; S, Sty I. bp, base pairs.

To verify that pJMS23 encodes the complete native gene without deletions, Southern blots of genomic DNA from A909 were probed with gene fragments from the clone. There were no differences found in the restriction maps of bca between A909 and pJMS23. The complete nucleotide sequence of bca was obtained independently on both stands using three strategies: transposon mutagenesis with Tn5seq1, synthetic oligonucleotide primers, and exonuclease III nested deletions (FIG. 5).

The complete nucleotide sequence of the bca locus and derived amino acid sequence for a single, large open reading frame are shown in FIG. 6A–6C. The structural gene consists of 3063 nucleotides, encodes 1020 amino acids, and has a calculated molecular mass of 108,705 Da. There is a procaryotic promoter consensus sequence (TATAAT) upstream (at −10) from the initiating codon (Doi, R. H., et al., *Microbiol. Rev.* 50:227–243 (1986)). There are no clear homologies in the −35 region assuming a spacing of 5–19 bases upstream from the −10 region (Hawley, D. K., et al., *Nucleic Acids Res.* 11:2377–2355 (1983)). The probable ribosomal binding site flanking the 5' end of bca is AGGAGA (Shine, J., et al., *Proc. Natl. Acad. Sci. USA* 71:1342–1346 (1974); Gold, L., et al., *Annu. Rev. Microbiol.* 38:365403 (1981)). Downstream of the TAA termination codon are two regions with dyad symmetry that could function as transcription terminators (Brendel, V., et al., *Nucleic Acids Res.* 12:4411–4127 (1984)).

The derived amino acid sequence of the mature peptide of bca predicts a $PK_a$ of 4.49, which is close to the experimentally measured values for both the native and the cloned C protein alpha antigen. The alpha antigen contains no cysteine and only a single methionine at the initiation codon. The alpha antigen is rich in proline (11% in the mature protein) but does not show the XPZ motif identified in the C protein beta antigen of GBS (Heden, L. -O., et al., *Eur. J. Immunol.* 21:1481–1490 (1991); Jerlstrom, P. G. et al., *Mol. MicrobioL* 5:843–849 (1991)) or the proline repeat motifs described in M protein of group A streptococci (Fischetti, V. A., et al., *Mol. Microbiol.* 4:1603–1605 (1990)).

Deduced Signal Sequence of bca and Homologies.

Figure 8:
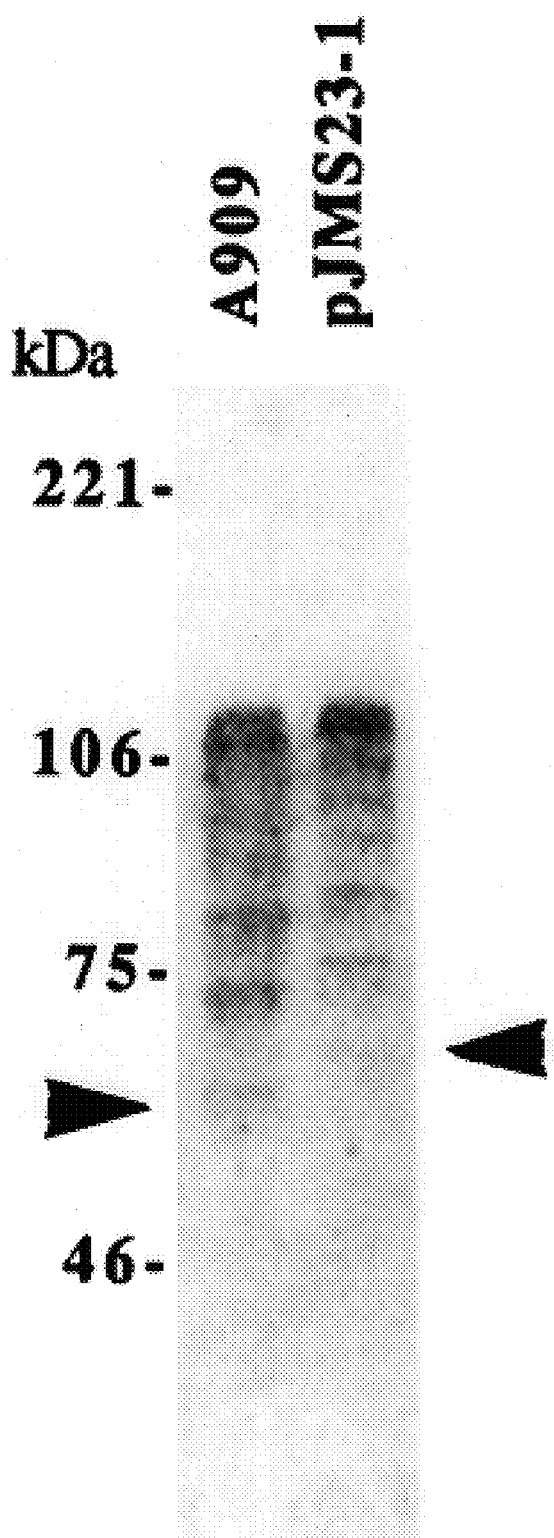
FIG. 8 shows a comparison of the cloned and native gene products of bca. Surface proteins of the A909 strain of group B Streptococcus (type 1a/C) and C protein alpha antigen clone pJMS23-1 were analyzed by SDS/PAGE and Western blotting and were probed with the alpha antigen-specific monoclonal antibody 4G8. Arrowheads illustrate an example of the difference between proteins. Molecular mass markers (in kDa) are shown on the right.

As a cell surface-associated protein, alpha antigen may use a signal sequence to be exported from the cytoplasm. A BLAST search identified five Gram-positive surface proteins with homology to the first 41 amino acids of the alpha antigen (FIG. 7A). Based on the pattern described for other Gram-positive signal sequences, it is likely that the first 41 amino acids of alpha antigen comprise a signal sequence (vonHeijne, G., *Eur. J. Biochem.* 133:17–21 (1983); vonHeijne, G. et al., *FEBS Lett.* 244:439–446 (1989)). There is a high proportion of arginine and lysine residues near the N terminal, followed by a hydrophobic region, a serine at position 36, and a valine at position 41. Other possibilities are cleavages after valine at position 54 or either of the alanine residues at positions 55 and 56 that follow a serine at position 52. Assuming that the signal sequence is cleaved following amino acid 41, the mature protein would contain 979 amino acids with a molecular mass of 104,106 Da. This suggests that the signal sequence is encoded by 123 nucleotides, making up 4% of the gene, and has a molecular mass of 4616 Da. Further support for a signal sequence of this size comes from Western blots comparing the sizes of the native and cloned alpha antigens probed with the monoclonal antibody 4G8. As shown in FIG. 8, each of the steps of the alpha antigen protein ladder from clone pJMS23 is slightly larger than that of the native protein from GBS A909, which suggests that the signal sequence may not be processed in *E. coli* as it would be in the GBS. The size difference is about 4 kDa, which would correspond to a shorter (41 amino acids) rather than a larger (53–55 amino acids) signal sequence in bca.

Analysis of the N Terminus of bca.

Following the putative signal sequence, there is a region of 185 amino acids before the repeated sequences. The N-terminal region contains 555 nucleotides, accounts for 18% of the gene, and encodes a polypeptide with a predicted molecular mass of 20,417 Da. A computer search comparing the primary nucleotide sequence and the derived amino acid sequence in all six reading frames of the N terminus of bca with sequences in GenBank and Swiss-Prot using the BLAST network of programs found no homologies, thus suggesting that this region of the gene is unlike any previously sequenced or described nucleic acid or amino acid sequence.

Repeating Unit Region of bca.

Figure 9:
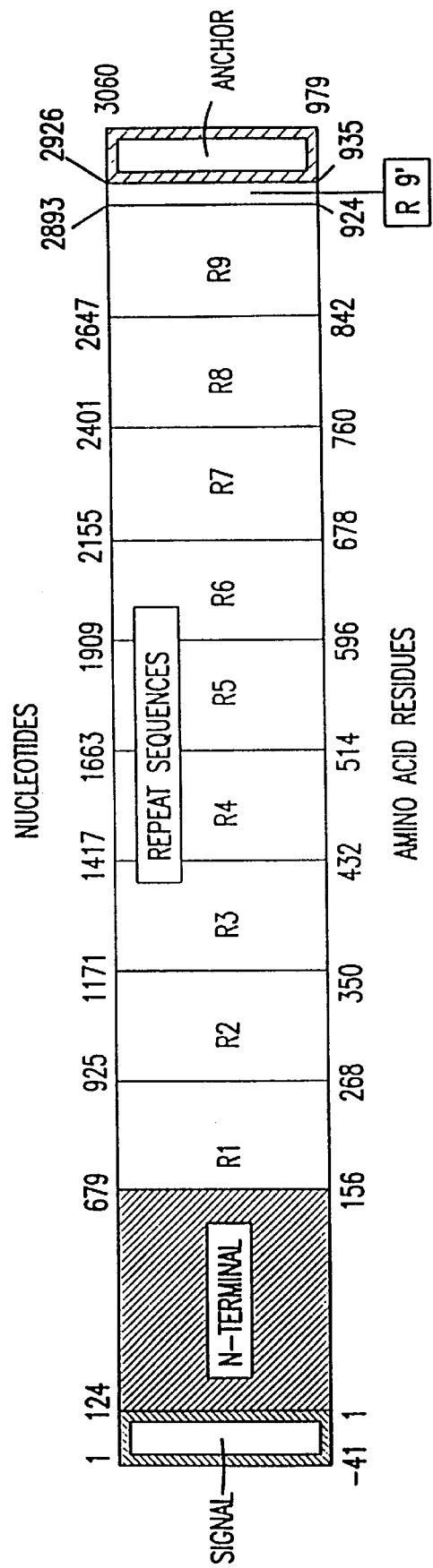
FIG. 9 shows a schematic of the open reading frame of bca. Summary of the structural features of the open reading frame of the C protein alpha antigen based on analysis of the amino acid sequence deduced from the nucleotide sequence of bca. The numbers above the boxes indicate the nucleotide position, and the numbers below are the amino acid residues of the mature protein within the open reading frame.

Beginning at amino acid 679 of the DNA sequence, there are nine large tandem repeating units with identical nucleic acid and amino acid structures that encompass 74% of the gene. The size and repetitive nature of this region of bca are illustrated in FIG. 9. Each repeating unit consists of 246 nucleotides encoding 82 amino acids with a calculated molecular mass of 8665 Da. The entire repeat region contains 749 amino acids and consists of the nine identical repeating units and a partial repeating unit designated 9'. The calculated molecular mass of this region is 79,053 Da.

The determination of the beginning and end of the repeat is somewhat arbitrary. Here, the determination starts from the N terminus, beginning with the first codon that was in the open reading frame. If desired, the repeating units could also be defined as beginning out of frame or starting at the C-terminal side. BLAST computer searches for nucleic acid and derived amino acid homologies showed to significant matches for the repeat units. Therefore, these repeating units appear to be unique to the alpha antigen and are different in size and structure from those described for other streptococcal proteins (Heden, L. -O., et al. *Eur. J. Immunol.* 21:1481–1490 (1991); Jerlstrom, P. G., et al., *Mol. Microbiol.* 5:843–849 (1991); Fischetti, V. A., et al., in *Genetics and Molecular Biology of Streptococci, Lactococci, and Enterococci*, Dunny et al. eds. Am. Soc. Microbiol., Washington (1991), pp. 290–294; Yother, J., et al., *J. Bacteriol.* 174:601–609 (1992)).

C-Terminal Anchor of bca and Homologies.

Following the repeating units is a small C-terminal region containing 148 nucleotides and making up 4.4% of the gene. This region encodes 45 amino acids with a calculated molecular mass of 4672 Da. A BLAST search for amino acid homologies identified a class of Gram-positive surface proteins with a common membrane anchor motif (FIG. 7B), including the M proteins of group A Streptococcus and IgG binding proteins from both group A and group G Streptococcus (Wren, B. W., *Mol. Microbiol.* 5:797–803 (1991)). The amino acid composition at the C terminus is characteristic of the peptide membrane anchor, including a hydrophilic stretch with lysine before the LPXTGE [SEQ ID NO:2] motif (FIG. 7B) (Fischetti, V. A. et al., *Mol. Microbiol.* 4:1603–1605 (1990)). This is followed by a hydrophobic region with the consensus PPFFXXAA [SEQ ID NO:1], where X designates a hydrophobic amino acid. Finally, there is a hydrophilic tail ending in aspartic acid that presumably extends into the cytoplasm of the cell.

Analysis of the Nucleotide Sequence and the Deduced Alpha Antigen Protein

FIG. 9 illustrates four distinct regions within the open reading frame of bca as determined from the nucleotide and derived amino acid sequences. A hydrophobicity plot of the amino acid sequence shows that the putative signal sequence has a short, hydrophilic N terminus, followed by a hydrophobic stretch, and ending in a hydrophilic region, whereas the C-peptide membrane anchor has a hydrophobic wall-spanning domain and a small hydrophilic tail (Engelman, D. M., et al., *Annu. Rev. Biophys. Biophys. Chem.* 15:321–353 (1986); Kyte, J., et al., *J. Mol. Biol.* 157:105–132 (1982)).

The native alpha antigen demonstrates a ladder of polypeptides at regularly repeating intervals that is also seen with the cloned gene product (FIG. 8). The size of the individual repeats in bca could code for a polypeptide of 8665 Da, which corresponds to the size differences in the protein ladder. To look at possible mechanisms generating protein heterogeneity, bca nucleotide and derived RNA and protein sequences were surveyed. Analysis of the nucleotide sequence of bca failed to show codons within the repeat regions that could cause early termination of translation. In addition, the amino acid sequence of the repeat region was screened with the Genetics Computer Group program for potential sites for proteolytic cleavage. A unique site within each repeat was sensitive to pH 2.5, represented by aspartic acid followed by proline. However, these sites were also found in the N terminus. Although the alpha antigen is relatively resistant to trypsin, there were numerous potential trypsin cleavage sites found in the sequence. Finally, modeling of RNA sequence and tertiary structure failed to identify regions within the repeats that might be involved with RNA-mediated self-cleavage.

Discussion

Two biological properties identified for the alpha antigen of GBS are the ability to resist opsomophagocytosis in the absence of specific antibody and the expression of epitopes that elicit protective antibodies (Madoff, L. C., et al., *Infect. Immun.* 59:2638–2644 (1991); Lancefield, R. C., et al., *J. Exp. Med.* 142:165–179 (1975); Payne, N. R., et al., *J. Infect. Dis.* 151:672–681 (1985); Payne, N. R., et al., *Infect. Immun.* 55:1243–1251 (1987)). Analysis of the sequence of the alpha antigen shows four distinct structural domains. The putative N-terminal signal sequence and the C-terminal membrane anchor support the hypothesis that the alpha antigen is a surface-associated membrane protein. These properties, along with the repeating unit motif, are shared by a number of Gram-positive proteins that are thought to be involved in the pathogenesis of bacterial infections (Fischetti, V. A., et al., in *Genetics and Molecular Biology of Streptococci, Lactococci, and Enterococci*, Dunny et al. eds. Am. Soc. Microbiol., Washington (1991), pp. 290–294).

The alpha antigen sequence identified a region of large, identical, tandem repeats composing 74% of the gene and demonstrating no homology to previously described protein or nucleic acids sequences. However, a number of virulence-associated proteins contain multiple repetitive elements. The M protein of group A Streptococcus, which is antiphagocytic, carries protective epitopes and displays variability in antigen size and presentation, contains two extended tandem repeat regions and one nontandem repeat region occupying nearly two-thirds of the gene (Fischetti, V. A., et al., *Rev. Infect. Dis.* S356–S359 (1988); Hollingshead, S. K., et al., *J. Biol. Chem.* 261:1677–1686 (1986); Haanes, E. J., et al., *J. Bacteriol.* 171:6397–6408 (1989)). The individual repeats are smaller in M protein than in the alpha antigen and range from 21 to 81 base pairs. In addition, there is divergence between the repeating units at the ends of the repeat region, while those in the middle are nearly identical. Pneumococcal surface protein A contains a region containing up to 10 repetitive segments of 20 amino acids each (Yother, J. et al., *J. Bacteriol.* 174:601–609 (1992)). Both M protein and pneumococcal surface protein A demonstrate antigenic variability and changes in protein/gene size thought to be mediated by repetitive DNA sequences in their structural genes (Fischetti, V. A., et al., in *Genetics and Molecular Biology of Streptococci, Lactococci, and Enterococci*, Dunny et al. eds. Am. Soc. Microbiol., Washington (1991), pp. 290–294; Yother, J., et al., *J. Bacteriol.* 174:601–609 (1992); Haanes, E. J., et al., *J. Bacteriol.* 171:6397–6408 (1989)). Other Gram-positive genes with repetitive motifs include the glycotransferase genes from *Streptococcus sobrinus* and *Streptococcus mutans* (Ferretti, J. J., et al., *J. Bacteriol.* 169:42714278 (1987); Shiroza, T., et al., *J. Bacteriol.* 170.810–816 (1988)). Immunodominant epitopes associated with repetitive sequences have been identified in a number of other pathogens including *Rickettsia rickettsii*, *Trichomonas vaginalis*, and *Clostridium difficile* (Dailey, D. C., et al., *Infect. Immun.* 59:2083–2088 (1991); Anderson, B. E., et al., *Infect. Immun.* 58:2760–2769 (1990); vonEichel-Streiber, C., et al., *Gene* 96:107–113 (1990)). The repeats found in alpha antigens are unique for three reasons: (i) They are larger than those found for other Gram-positive surface proteins. (ii) They are identical at the nucleic acid level and do not diverge. (iii) The size of protein encoded by the repeating units corresponds to the laddering seen in the native and cloned alpha antigens.

The findings of large tandem repeating units raises many questions about the genotypic and phenotypic variability of the alpha antigen. When probed on Western immunoblots with the 4G8 monoclonal antibody, both the native and the cloned alpha antigen display a regular ladder of proteins varying by about 8 kDa, and the size of the alpha antigen varies between strains (Madoff, L. C., et al. *Infect. Immun.* 59:2638–2644 (1991)). Restriction endonuclease mapping of the original alpha antigen clone pJMS23 showed multiple Sty I fragments of about 270 base pairs (Michel, J. L., et al., Infect. Immun. 59:2023–2028 (1991)). Since strain A909 contains only one copy of bca it was proposed that these fragments may be responsible for the protein heterogeneity. The nucleotide sequence confirms the repetitive nature of the gene but does not identify the mechanism of protein laddering.

Since multiple protein sizes are seen in both native and cloned backgrounds and since there is no evidence for a gene family, we postulate that laddering results from a mechanism common to both *E. coli* and GBS and/or is mediated by a property specific to the alpha antigen. Western blots on Tn5 transposon insertion mutations within the repeat region still show laddering, which demonstrates that the C terminus is not required for heterogeneity, suggesting that either the N-terminal or repeat region determines laddering.

Studies of the alpha antigen among GBS isolates using a monoclonal antibody showed that the maximum molecular size of the alpha antigen is constant for a given isolate but varies widely among different isolates (Madoff, L. C., et al., *Infect. Immun.* 59:2638–2644 (1991)). The tandem repeating units could provide convenient fixed recombination sites for deletion or duplication of the repeat region. Deletion would reduce the size of the gene and might occur during DNA replication by unequal crossover or mispaired template slippage, which would occur in frame (Harayama, S., et al., *J. Bacteriol* 173:7540–7548 (1991)). Duplication of DNA could be a mechanism to amplify mutations within a repeat and create antigenic diversity. However, we have no evidence that the variation in the protein size of the alpha antigen is accompanied by antigenic diversity and the expression of different protective or opsonic epitopes.

The nine complete tandem repeats in the alpha antigen from A909 are identical at the nucleic acid level, which demonstrates a highly conserved structure. This suggests that the duplication causing the repeats is a recent event, that there are properties internal to the repeats that maintain their integrity, or that their structure is essential for the gene. Southern blots of genomic DNA from alpha antigen-bearing strains of GBS probed with alpha antigen-specific DNA show variability in gene size among strains. To look at the mechanism of genotypic diversity among strains, it will be necessary to clone and sequence bca from other phenotypic variants and to determine the phylogenetic relationships among C protein-bearing strains of GBS (Michel, J. L., et al. in *Genetics and Molecular Biology of Streptococci, Lactococci, and Enterococd*, Dunny, G. M., et al. eds., Am. Soc. Microbiol., Washington (1991), pp. 214–218; Michel, J. L., et al., *Infect. Immun.* 59:2023–2028 (1991); Cleat, P. H., et al., *Infect. Immun.* 55:1151–1155 (1987); Heden, L. -O., et al. *Eur. J. Immunol.* 21:1481–1490 (1991); Lindahl, G., et al. *Eur. J. Immunol.* 20:2241–2247 (1990)).

Therefore, in summary, Western blots of both the native alpha antigen and the cloned gene product demonstrate a regularly laddered pattern of heterogeneous polypeptides. The nucleotide sequence of the bca locus reveals an open reading frame of 3060 nucleotides encoding a precursor protein of 108,705 Da. Cleavage of a putative signal sequence of 41 amino acids yields a mature protein of 104,106 Da. The 20,417-Da N-terminal region of the alpha antigen shows no homology to previously described protein sequences and is followed by a series of nine tandem repeating units that make up 74% of the mature protein. Each repeating unit is identical and consists of 82 amino acids with a molecular mass of 8665 Da, which is encoded by 246 nucleotides. The size of the repeating units corresponds to the observed size differences in the heterogeneous ladder of alpha C proteins expressed by GBS. The C-terminal region of the alpha antigen contains a membrane anchor domain motif that is shared by a number of Gram-positive surface proteins. The large region of identical repeating units in bca defines protective epitopes and its structure may be manipulated for the construction of protective vaccines that are directed to the phenotypic and genotypic diversity of the alpha antigen.

EXAMPLE 15

A Vaccine Containing C Protein Alpha Antigen Functional Derivatives Having at Least one of the Native Repeating Units The above-described protective C protein alpha antigen functional derivatives (such as a protein moiety of N, C, N—C, $R_1$, $R_2$, $R_3$, $R_4$, $R_5$, $R_6$, $R_7$, $R_8$, $R_9$, N—$R_1$, N—$R_2$, N—$R_3$, N—$R_4$, N—$R_5$, N—$R_6$, N—$R_7$, N—$R_8$, N—$R_9$, $R_1$—C, $R_2$—C, $R_3$—C, $R_4$—C, $R_5$—C, $R_6$—C, $R_7$—C, $R_8$—C, $R_9$—C, N—$R_1$—C, N—$R_2$—C, N—$R_3$—C, N—$R_4$—C, N—$R_5$—C, N—$R_6$—C, N—$R_7$—C, N—$R_8$—C, or N—$R_9$—C) may be prepared by recombinant means using recombinant methods similar to those described above for cloning and expressing the native group B Streptococcus alpha antigen and beta antigen in hosts such as *E. coli*. Any technique may be utilized to synthesize the desired alpha antigen functional derivative sequence, including those described above for the recombinant production of these proteins, and those described by Williams, J. I., et al., U.S. Pat, No. 5,089,406 ("Method of Producing a Gene Cassette Coding for Polypeptides with Repeating Amino Acid Sequences," incorporated herein by reference) and by McPherson, M. J., ed., *Directed Mutagenesis, A Practical Approach*," IRL Press, New York, 1991.

The recombinantly expressed, above-described protective C protein alpha antigen functional derivatives (such as a protein moiety of N, C, N—C, $R_1$, $R_2$, $R_3$, $R_4$, $R_5$, $R_6$, $R_7$, $R_8$, $R_9$, N—$R_1$, N—$R_2$, N—$R_3$, N—$R_4$, N—$R_5$, N—$R_6$, N—$R_7$, N—$R_8$, N—$R_9$, $R_1$—C, $R_2$—C, $R_3$—C, $R_4$—C, $R_5$—C, $R_6$—C, $R_7$—C, $R_8$—C, $R_9$—C, N—$R_1$—C, N—$R_2$—C, N—$R_3$—C, N—$R_4$—C, N—$R_5$—C, N—$R_6$—C, N—$R_7$—C, N—$R_8$—C, or N—$R_9$—C) may be purified, if necessary, from the recombinant host or medium using techniques known in the art and then tested for their potential in a conjugate vaccine. Each peptide species may be tested alone, or in combination with other peptides. To assess this potential, cellular extracts of *E. coli* containing recombinant plasmids are prepared as described above, and used to immunize rabbits. The resulting antisera are tested in the mouse lethality model for their ability to protect mice from infection by the group B Streptococcus strain H36B. Strain H36B carries the C protein of group B Streptococcus. As a control, the ability of the antisera to protect the mice against infection by Streptococcus strain 515 (which does not carry the C protein) is determined.

A similar assay may be used to assess the conjugated form wherein the peptide is conjugated to a group B Streptococcus polysaccharide using the above described techniques known in the art. Preferably, this is a group B Streptococcus capsid polysaccharide. The conjugates are used to immunize rabbits. The resulting antisera are tested in the mouse lethality model for their ability to protect mice from infection by the group B Streptococcus strain H36B. Strain H36B carries the C protein of group B Streptococcus. As a control, the ability of the antisera to protect the mice against infection by Streptococcus strain 515 (which does not carry the C protein) is determined.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A conjugate vaccine that confers host immunity to an infection in a mammal by group B Streptococcus which comprises (a) a group-specific or type-specific group B Streptococcus polysaccharide conjugated to (b) a functional derivative of the group B Streptococcus C protein alpha antigen, wherein said derivative elicits protective antibodies against said group B Streptococcus.

2. A method for preventing or attenuating an infection in a mammal caused by a group B Streptococcus that comprises administering to an individual, an effective amount of a conjugate vaccine, said conjugate vaccine conferring protective host immunity against an infection by group B Streptococcus wherein said vaccine comprises a therapeutically effective amount of:

(a) a capsular polysaccharide that elicits antibodies to group B Streptococcus; conjugated to (b) a C protein alpha antigen or beta antigen of said group B Streptococcus, wherein said alpha antigen is a group B Streptococcus protein of at least 40,000 daltons that is recognized by antiserum to the C protein encoded by pJMS23, and wherein said beta antigen is a group B Streptococcus protein of at least 50,000 daltons that is recognized by antiserum to the protein encoded by pJMS1;

wherein said vaccine is substantially free of streptococcal proteins other than said C protein alpha antigen or said C protein beta antigen, said conjugate vaccine is in a pharmacologically acceptable composition and wherein both said capsular polysaccharide and said C protein contributes to the development of said protective host immunity to said infection.

3. The method of claim 2, wherein said C protein of the conjugate vaccine is encoded by a plasmid selected from the group consisting of pJMS23 and plasmid pJMS1.

4. The method of claim 2, wherein said C protein of the conjugate vaccine is said alpha antigen.

5. The method of claim 4, wherein said alpha antigen is that encoded by plasmid pJMS23.

6. The method of claim 2, wherein said C protein of the conjugate vaccine is said beta antigen.

7. The method of claim 6, wherein said beta antigen is that encoded by plasmid pJMS1.

8. A method for preventing or attenuating an infection in a mammal caused by a group B Streptococcus that comprises administering to an individual, an effective amount of a conjugate vaccine, said conjugate vaccine conferring protective host immunity against an infection by group B Streptococcus wherein said vaccine comprises a therapeutically effective amount of: (a) a group B Streptococcus capsular polysaccharide that elicits antibodies to group B Streptococcus; conjugated to (b) a functional derivative selected from the group B Streptococcus C proteins consisting of an alpha antigen, a beta antigen, fragments of said alpha antigen, fragments of said beta antigen and combinations thereof, wherein said derivative elicits protective antibodies against said group B Streptococcus.

9. The method of claim 8, wherein said polysaccharide of the conjugate vaccine is a capsular polysaccharide.

10. The method of claim 8, wherein said C protein alpha antigen derivative of said conjugate vaccine is selected from the group consisting of N, C, N—C, $R_1$, $R_2$, $R_3$, $R_4$, $R_5$, $R_6$, $R_7$, $R_8$, $R_9$, $R_{9'}$, $R_x$, N—$R_1$, N—$R_2$, N—$R_3$, N—$R_4$, N—$R_5$, N—$R_6$, N—$R_7$, N—$R_8$, N—$R_9$, N—$R_{9'}$, N—$R_x$, $R_1$—C, $R_2$—C, $R_3$—C, $R_4$—C, $R_5$—C, $R_6$—C, $R_7$—C, $R_8$—C, $R_9$—C, $R_{9'}$—C, $R_x$—C, N—$R_1$—C, N—$R_2$—C, N—$R_3$—C, N—$R_4$—C, N—$R_5$—C, N—$R_6$—C, N—$R_7$—C, N—$R_8$—C, N—$R_9$—C, N—$R_{9'}$—C; N—$R_x$—C and combinations thereof where "X" is 10 or greater, where "N" is the N-terminal sequence that precedes the start of the alpha antigen repeating unit sequence that is found in the sequence shown in FIG. 6 (SEQ ID NO:15), with or without the signal sequence, "C" is the 45 amino acid C-terminal anchor sequence as shown on FIG. 6 (SEQ ID NO:15), "R" is one copy of the 82 amino acids 227–308 of the sequence of FIG. 6 (SEQ ID NO:15), and "$R_x$" is "X" number of tandem copies of this repeat, tandemly joined at the carboxyl end of one R unit to the amino terminal end of the adjoining R unit, and 9' represents the sequence of amino acids 227–975 as shown in FIG. 6 (SEQ ID NO:15).

11. The method of claim 8, wherein said derivative is selected from the group consisting of N, C, $R_1$, $R_2$, $R_3$, $R_4$, $R_5$, $R_6$, $R_7$, $R_8$, $R_9$, $R_{9'}$, $R_x$ where "X" is 10 or greater, and combinations thereof.

12. The method of claim 11, wherein said derivative is selected from the group consisting of N, C, $R_1$, $R_2$, $R_3$, $R_4$, $R_5$, $R_6$, $R_7$, $R_8$, $R_9$, $R_{9'}$, and $R_x$ where "X" is 10 or greater.

13. The method of claim 10, wherein said derivative is selected from the group consisting of N—C, N—$R_1$, N—$R_2$, N—$R_3$, N—$R_4$, N—$R_5$, N—$R_6$, N—$R_7$, N—$R_8$, N—$R_9$, N—$R_{9'}$, N—$R_x$ where "X" is 10 or greater, and combinations thereof.

14. The method of claim 13, wherein said derivative is selected from the group consisting of N—C, N—$R_1$, N—$R_2$, N—$R_3$, N—$R_4$, N—$R_5$, N—$R_6$, N—$R_7$, N—$R_8$, N—$R_9$, N—$R_{9'}$, and N—$R_x$ where "X" is 10 or greater.

15. The method of claim 10, wherein said derivative is selected from the group consisting of $R_1$—C, $R_2$—C, $R_3$—C, $R_4$—C, $R_5$—C, $R_6$—C, $R_7$—C, $R_8$—C, $R_9$—C, $R_{9'}$—C, $R_x$—C where "X" is 10 or greater, and combinations thereof.

16. The method of claim 15 wherein said derivative is selected from the group consisting of $R_1$—C, $R_2$—C, $R_3$—C, $R_4$—C, $R_5$—C, $R_6$—C, $R_7$—C, $R_8$—C, $R_9$—C, $R_{9'}$—C, and $R_x$—C where "X" is 10 or greater.

17. The method of claim 10, wherein said derivative is selected from the group consisting of N—$R_1$—C, N—$R_2$—C, N—$R_3$—C, N—$R_4$—C, N—$R_5$—C, N—$R_6$—C, N—$R_7$—C, N—$R_8$—C, N—$R_9$—C, N—$R_{9'}$—C, N—$R_x$—C where "X" is 10 or greater, and combinations thereof.

18. The method of claim 17, wherein said derivative is selected from the group consisting of N—$R_1$—C, N—$R_2$—C, N—$R_3$—C, N—$R_4$—C, N—$R_5$—C, N—$R_6$—C, N—$R_7$—C, N—$R_8$—C, N—$R_9$—C, N—$R_{9'}$—C, and N—$R_x$—C where "X" is 10 or greater.

19. The method of claim 2, wherein said capsular polysaccharide is type-specific.

20. The method of claim 8, wherein said capsular polysaccharide is type-specific.

21. The method of claim 10, wherein said C protein alpha antigen derivative of said conjugate vaccine is selected from the group consisting of N, C, N—C, $R_1$, $R_2$, $R_3$, $R_4$, $R_5$, $R_6$, $R_7$, $R_8$, $R_9$, $R_{9'}$, $R_x$, N—$R_1$, N—$R_2$, N—$R_3$, N—$R_4$, N—$R_5$, N—$R_6$, N—$R_7$, N—$R_8$, N—$R_9$, N—$R_{9'}$, N—$R_x$, $R_1$—C, $R_2$—C, $R_3$—C, $R_4$—C, $R_5$—C, $R_6$—C, $R_7$—C, $R_8$—C, $R_9$—C, $R_{9'}$—C, $R_x$—C, N—$R_1$—C, N—$R_2$—C, N—$R_3$—C, N—$R_4$—C, N—$R_5$—C, N—$R_6$—C, N—$R_7$—C, N—$R_8$—C, N—$R_9$—C, N—$R_{9'}$—C, and N—$R_x$—C where "X" is 10 or greater.

* * * * *